US012252699B2

(12) United States Patent
Poirot et al.

(10) Patent No.: US 12,252,699 B2
(45) Date of Patent: Mar. 18, 2025

(54) METHOD FOR GENERATING T-CELLS COMPATIBLE FOR ALLOGENIC TRANSPLANTATION

(71) Applicant: CELLECTIS, Paris (FR)

(72) Inventors: Laurent Poirot, Paris (FR); David Sourdive, Levallois-Perret (FR); Philippe Duchateau, Dravell (FR); Jean-Pierre Cabaniols, Saint Lau la Foret (FR)

(73) Assignee: CELLECTIS, Paris (FR)

( * ) Notice: Subject to any disclaimer, the term of this patent is extended or adjusted under 35 U.S.C. 154(b) by 0 days.

(21) Appl. No.: 18/480,890

(22) Filed: Oct. 4, 2023

(65) Prior Publication Data
US 2024/0026376 A1    Jan. 25, 2024

Related U.S. Application Data

(62) Division of application No. 16/138,908, filed on Sep. 21, 2018, now Pat. No. 11,820,996, which is a division of application No. 15/123,974, filed as application No. PCT/EP2015/055097 on Mar. 11, 2015, now abandoned.

(30) Foreign Application Priority Data

Mar. 11, 2014 (DK) .............................. PA201470119

(51) Int. Cl.
| C12N 15/85 | (2006.01) |
| A61K 35/17 | (2015.01) |
| A61K 39/00 | (2006.01) |
| C07K 14/705 | (2006.01) |
| C07K 14/74 | (2006.01) |
| C12N 5/0783 | (2010.01) |
| C12N 15/113 | (2010.01) |
| C12N 15/90 | (2006.01) |

(52) U.S. Cl.
CPC ............. *C12N 15/85* (2013.01); *A61K 35/17* (2013.01); *A61K 39/0011* (2013.01); *C07K 14/70503* (2013.01); *C07K 14/70539* (2013.01); *C12N 5/0636* (2013.01); *C12N 15/1138* (2013.01); *C12N 15/907* (2013.01); *A61K 2039/5156* (2013.01); *A61K 2039/5158* (2013.01); *C07K 2317/24* (2013.01); *C07K 2317/622* (2013.01)

(58) Field of Classification Search
CPC .. C12N 15/85; C12N 5/0636; C12N 15/1138; C12N 15/907; A61K 35/17; A61K 39/0011; A61K 2039/5156; A61K 2039/5158; A61K 35/28; C07K 14/70503; C07K 14/70539; C07K 2317/24; C07K 2317/622; C07K 14/7051; C07K 2319/03; C07K 14/705; A61P 35/00; A61P 35/02; A61P 31/12
See application file for complete search history.

(56) References Cited

U.S. PATENT DOCUMENTS

| 9,587,237 B2 | 3/2017 | Hyde et al. |
| 10,370,452 B2 | 8/2019 | Themeli et al. |
| 11,186,824 B2 | 11/2021 | Duchateau |
| 2006/0222633 A1 | 10/2006 | Shlomchik et al. |
| 2007/0036773 A1 | 2/2007 | Cooper et al. |
| 2014/0349402 A1 | 11/2014 | Cooper et al. |
| 2016/0222633 A1 | 8/2016 | Kang |
| 2018/0141992 A1 | 5/2018 | Cowan et al. |
| 2019/0010514 A1 | 1/2019 | Poirot |

FOREIGN PATENT DOCUMENTS

| WO | 93/02188 A1 | 2/1993 |
| WO | 95/17911 A1 | 7/1995 |
| WO | 2005/097160 A2 | 10/2005 |
| WO | 2008/102274 A2 | 8/2008 |
| WO | 2009/141729 A2 | 11/2009 |
| WO | 2012/138927 A2 | 10/2012 |
| WO | 2012/145384 A1 | 10/2012 |

(Continued)

OTHER PUBLICATIONS

Zijlstra, M., Bix, M., Simister, N.E., Loring, J.M., Raulet, D.H. and Jaenisch, R., 1990. 32-microglobulin deficient mice lack CD4-8+ cytolytic T cells. Nature, 344(6268), pp. 742-746. (Year: 1990).*
Joung, J.K. and Sander, J.D., 2013. TALENs: a widely applicable technology for targeted genome editing. Nature reviews Molecular cell biology, 14(1), pp. 49-55. (Year: 2013).*
Torikai et al. A foundation for univeral T-cell based immunotherapy: T cell engineered to express a CD19-specific chimeric-antigen-receptor and eliminate expression of endogenous TCR. Blood, 2012, 119(24), 5697-5705.
Hirano et al. Blockade of B7-H1 and PD-1 by monoclonal antibodies potentiates cancer therapeutic immunity. Cancer Res, 2005, 65(3), 1089-1096.
Carroll. A CRISPR approach to gene targeting. Molecular Therapy, 2012, 20(9), 1658-1660.

(Continued)

*Primary Examiner* — Jeremy C Flinders
*Assistant Examiner* — Masudur Rahman
(74) *Attorney, Agent, or Firm* — Arrigo, Lee, Guttman & Mouta-Bellum LLP

(57) ABSTRACT

The present invention pertains to engineered T-cells, method for their preparation and their use as medicament, particularly for immunotherapy. The engineered T-cells of the invention are characterized in that the expression of beta 2-microglobulin (B2M) and/or class II major histocompatibility complex transactivator (CIITA) is inhibited, e.g., by using rare-cutting endonucleases able to selectively inactivating by DNA cleavage the gene encoding B2M and/or CIITA, or by using nucleic acid molecules which inhibit the expression of B2M and/or CIITA. In order to further render the T-cell non-alloreactive, at least one gene encoding a component of the T-cell receptor is inactivated, e.g., by using a rare-cutting endonucleases able to selectively inactivating by DNA cleavage the gene encoding said TCR component.

12 Claims, 9 Drawing Sheets
Specification includes a Sequence Listing.

(56) References Cited

FOREIGN PATENT DOCUMENTS

| WO | 2013/049459 A2 | 4/2013 |
| WO | 2013/074916 A1 | 5/2013 |
| WO | 2013/158292 A1 | 10/2013 |
| WO | 2013/176915 A1 | 11/2013 |
| WO | 2014/138315 A1 | 9/2014 |
| WO | 2014/159435 A1 | 10/2014 |
| WO | 2014/165707 A2 | 10/2014 |
| WO | 2015/136001 A1 | 9/2015 |

OTHER PUBLICATIONS

Champsaur et al., Effect of NKG2D ligand expression non host immune responses. Immunological Reviews, 2010, 235, 267-285.

Dammeyer et al., "Vaccination with β2-Microglobulin-Deficient Dendritic Cells Protects Against Growth of β2-Microglobulin-Deficient Tumours," Scandinavin Journal of Immunology, 2009, 701(1), 44-52.

Gaj et al., ZFN, TALEN, and CRISPR/Cas-based methods for genome. Trends in Biotechnology, 2013, 31(7), 397-405.

Höglund et al., "Recognition of β2-microglobulin-negative (β2m) T-cell blasts by natural killer cells from normal but not from β2m mice: Nonresponsiveness controlled by β2m bone marrow in chimeric mice, Proceedings of the National Academy of Sciences," 1991, 88, 22, 10332-10336.

Holling et al., "Epigenetic silencing of MHC2TA transcription in cancer," Biochemical Pharmacology, 2006, 72(11), 1570-1576.

International Search Report and Written Opinion issued in PCT/EP2015/055097 mailed May 15, 2015.

Matsunaga et al., Activation of Antigen-Specific Cytotoxic T Lymphocytes by β2-Microglobulin or TAPI Gene Disruption and the Introduction of Recipient-Matched MHC Class I Gene in Allogeneic Embryonic Stem Cell-Derived Dendritic Cells, The Journal of Immunology, 2008, 181, 9, 6635-6643.

Riolobos et al., "HLA Engineering of Human Pluripotent Stem Cells," Molecular Therapy, 2013, 21(6), 1232-1241.

Soland et al., "Modulation of Human Mesenchymal Stem Cell Immunogenicity through Forced Expression of Human Cytomegalovirus US Proteins," PLoS One, 2012, 7(5), 1-15.

Trichet et al., "Complex Interplay of Activating and Inhibitory Signals Received by V Y9Vö2 T Cells Revealed by Target Cell ß2-Microglobulin Knockdowns" The Journal of Immunology, 2006, 177(9), 6129-6136.

Wieczorek et al., "Genetically Modified T Cells for the Treatment of Malignant Disease," Transfusion Medicine and Hemotherapy, 2013, 40(6), 388-402.

Torikai. Toward eliminating HLA class I expression to generate universalcells from allogeneic donors, Blood Journal, 2013, 122(8), 1341-1349.

Joung et al. TALENs: a widely applicable technology for targeted genome editing. Nat Rev Mol Cell Biol., 2013, 14, 49-55.

Cunningham et al. The complete amino acid sequence of beta 2-microglobulin. Biochemistry, 1973, 12(24), 4811-4822.

Zijstra et al. Beta 2 microglobulin deficient mice lack CD4-8+ cytolytic T cells, Nature, 1990, 344, 742-746.

Richman S. A. et al. High-affinity GD2-specific Car T cells induce fatal encephalitis in a preclinical neuroblastoma model, Cancer immunology research, 2018, 6(1), 36-46.

Teplyakov A. et al., Antibody modeling assessment II. Structures and models, Proteins: Structure, Function, and Bioinformatics, 2014, 82(8), 1563-1582.

Chen X. et al. Fusion protein linkers: property, design and functionality, Advanced drug delivery reviews, 2013, 65(10), 1357-1369.

Maeda Y. et al. Engineering of functional chimeric protein G-VargulaLuciferase, Analytical biochemistry, 1997, 249(2), 147-152.

Dolezal O. et al. ScFv multimers of the anti-neuraminidase antibody NC10: shortening of the linker in single-chain Fv fragment assembled in VL to VH orientation drives the formation of dimers, trimers, tetramers and higher molecular mass multimers, Protein engineering, 2000, 13(8), 565-574.

Long A. H. et al. 4-1BB costimulation ameliorates T cell exhaustion induced by tonic signaling of chimeric antigen receptors, Nature Medicine, 2015, 21(6), 581-590.

Srivastava S. et al. Engineering CAR-T cells: design concepts, Trends in immunology, 2015, 36(8), 494-502.

Hudecek M. et al. The nonsignaling extracellular spacer domain of chimeric antigen receptors is decisive for in vivo antitumor activity, Cancer immunology research, 2015, 3(2), 125-135.

Hege K. M. et al. Safety, tumor trafficking and immunogenicity of chimeric antigen receptor (CAR)-T cells specific for TAG-72 in colorectal cancer, Journal for immunotherapy of cancer, 2017, (5)1, 1-14.

Guedan S. et al. Enhancing Car T cell persistence through ICOS and 4-1BB costimulation, JCI insight, 2018, 3(1), 11-13.

Bix et al. Rejection of class I MHC-deficient haemopoietic cells by irridiated MHC-matched mice, Letters to Nature, 1991, vol. 349, 329-331.

Campoli and Ferrone. Tumor escape mechanisms: potential role of soluble HLA antigens and NK cells activating ligands. Tissue Antigens, 2008, 72(4), 321-334.

Depil et al. 'Off-the-shelf' allogeneic Car T cells: development and challenges. Nature Reviews. vol 19, 2020, 185-199.

Williams et al. Evaluation of engineering strategies allowing efficient adoptive transfer of CAR T-cells in an allogeneic setting, Keystone, 2018, 1-10.

Figueiredo et al. Regulating MHC expression for cellular therapeutics. Transplantation and Cellular Engineering. 2007, 47, 18-27.

Glas et al. Major histocompatibility complex class I-specific and -restricted killing of β2-microglobulin-deficient cells by CD8+ cytotoxic T lymphocytes, Proc Natl Acad Sci, 1992, 89, 11381-11385.

Gonzalez et al. Amplification of RNAi-Trageting HLA mRNAs. Molecular Therapy, 2005, 11(5), 811-818.

Guo et al. Mutant β2M-HLA-E and B2M-HLA-G fusion proteins protects universal chimeric antigen receptor-modified T cells from allogeneic NK cell-mediated lysis, European Journal of Immunology, 2021, 51, 2513-2521.

John et al. Anti-PD-1 antibody therapy potently enhances the eradication of established tumors by gene-modified T cells. Clinical Cancer Research. 2013, 19(20), 5636-5646.

Kim et al. Human cytomegalovirus UL18 utilizes US6 for evading the NK and T-cell responses, PLOS Phatogens, 2008, 4(8), 1-11.

Le et al. CIITA transformation rescues the apoptotic function of MHC class II melanoma cells. Anticancer Research, 2005, 25, 3889-3892.

Liu et al. CRISPR-Cas9-mediated multiplex gene editing in CAR-T cells. Cell Research (2017) 27, 154-157.

Ljungrenn and Karre. In search of the 'missing self': MHC molecules and NK cell recognition. Immunology Today, 11(7), 1990, 237-244.

Lloyd et al. Beyond the antigen receptor: editing the genome of T-cells for cancer adoptive cellular therapies. Frontiers in Immunology, 2013, 4, 1-7.

Lu et al. Generating hypoimmunogenic human embryonic stem cells by the disruption of Beta 2-Microglobulin, Stem Cell Rec and Rep, 2013, 9, 806-813.

Mach et al. MHC Class II-Deficient combined immunodefiency: A disease of gene regulation. Immunological Reviews, 1994, 138, 207-221.

Mandal and Viswanathan. Natural killer cells: in health and disease. Hematl Oncol Stem Cell Ther, 2015, 8(2), 47-55.

Masternak et al. CIITA is a transcriptional coactivator that is recruited to MHC class II promoters by multiple synergistic interactions with an enhanceosome complex. Genes and Development. 2000, 14, 1156-1166.

Valton. Evaluation of engineering strategies allowing efficient allogeneic adoptive transfer of Car T cells in an immunocompetent in vivo model. Keystone Symposia Conference. 2018.

(56) References Cited

OTHER PUBLICATIONS

Provasi et al. Editing T cell specificity towards leukemia by zinc finger nucleases and lentiviral gene transfer. Nature Medicine, 2012, 18(5), 807-815.
Ren et al. Multiplex genome editing to generate universal Car T cells resistant to PD1 inhibition. Clinical Cancer Research, 2016, 23(9), 2255-2266.
Reyburn et al. The class I MHC homologue of human cytomegalovirus inhibits attack by natural killer cells. Nature, 1997, 286, 514-517.
Burns W. R. et al. A high molecular weight melanoma-associated antigen-specific chimeric antigen receptor redirects lymphocytes to target human melanomas, Cancer research, 2010, 70(8), 3027-3033.
Salih et al. Functional expression and release of ligands for the activating immunoreceptor NKG2D in leukemia. Blood, 2003, 102(4), 1389-1396.
Scharenberg et al. Genome engineering with TAL-effector nucleases and alternative modular nuclease technologies. Current Gene Tehrapy, 2013, 13, 291-303.
Turtle C. J. et al. CD19 Car-T cells of defined CD4+: CD8+ composition in adult B cell ALL patients, The Journal of clinical investigation, 2016, 126(6), 2123-2138.
Themeli et al. Generation of tumor-targeted human T lymphocytes from induced pluripotent stem cells for cancer therapy. Nature Biotechnology. 2013, 31(10), 928-933.
Torikai et al. Engineering T cells to target tumor cells. Engineering in Translational Medicine, 2014, vol. 1, 71-101.
Wilkinson et al. Modulation of natural killer cells nby human cytomegalovirus, J Clin VIrol, 2008, 41(3), 206-212.
Poirot al., T-Cell Engineering for "off-The-shelf" Adoptive Immunotherapy, Blood, 2013, 122(21), 1661 (Abstract).
Oberg et al. Loss and mismatch of MHC class I is sifficient to trigger NK cell-mediated rejection of resting lymphocytes in vivo-role of KARAP/DAP12-dependent and -independent pathways. Eur J Immunol, 2004, 34, 1646-1653.
Cellectis. Cellectis bioresearch launches Compact TALEN the next generation of TAL effector nucleases. Cellectis Bioresearch, 2013, 1-2. https://www.cellectis.com/en/press/cellectis-bioresearch-launches-compact-talen-the-next-generation-of-tal-effector-nucleases/.
Williams et al. Evaluation of engineering strategies allowing efficient adoptive transfer of CAR T-cells in an allogeneic setting, Presented at the Keystone Symposia Conference entitled "Emerging Cellular Therapies: T Cells and Beyond," Feb. 11-15, 2018, 3020, 1-10.
Figueiredo et al. MHC Universal cells survive in an allogeneic environment after incompatible transplantation. BioMed Research International, 2013, 796046, 1-12. doi: 10.1155/2013/796046.
John et al. Blockade of PD-1 immunosuppression boosts CAR T-cell therapy. Oncoimmunology, 2013, 19(20), 1-3.
Kayoga et al. Genetic ablation of HLA class I, class II, and the T-cell receptor enables allogeneic T cells to be used for adoptive T cell therapy. American Association for Cancer Research Journals. 2020, 8, 926-936.
Karre et al. Pillars Article: Selective rejection of H-2 deficient lymphoma variants suggests alternative immune defence strategy, Nature, 1986, 319, 675-678.
McCreedy et al. Off the shelf T cell therapies for hematologic malignancies. Best Practices and Research in Clinical Hematology, 2018, 31(2), 166-175.
Meissner et al. Genome editing for human gene therapy. Methods in Enzymology, 2014, 546, ISSN 0076-6879, 273-295.
Cellectis, TALEN Solutions is a comprehensive package of solutions for all gene editing projects from Cellectic bioresearch, cell engineering expert since 1999. 2013, 1-3. http://www.cellectis-bioresearch.com/talen-solutions.
Zhang et al. Chimeric Antigen Receptor (CAR) Treg: A promising approach to inducing immunological tolerance, Frontiers in Immunology, 2018, 9, 2359, 1-8.
Beurdeley et al. Compact designer TALENs for efficient genome engineering. Nature Communications. 2013, 4, 1762, 1-8.
Bix and Raulet. Functionally conformed free class I heavy chains exist on the surface of $\beta 2$ microglobulin negative cells. J Exp Med, 1992, 176, 829-834.
Guha P. et al. Frontline Science: Functionally impaired geriatric CAR-T cells rescued by increased $\alpha 5\beta 1$ integrin expression, Journal of leukocyte biology, 2017, 102(2), 201-208.
Yee J. K. Off-target effects of engineered nucleases, The FEBS Journal, 2016, 283(17), 3239-3248.
Tsai S et al. GUIDE-seq enables genome-wide profiling of off-target cleavage by CRISPR-Cas nucleases, Nature biotechnology, 2015, 33(2), 187-197.
Tilova L. R. et al. Molekulârno genetičeskie narušeniâ v patogeneze opuholej sistemy krovi [Molecular genetic abnormalities in the pathogenesis of hematologic malignancies and corresponding changes in cell signaling systems], Kliničeskaâ onkogematologiâ , 2017, 10(2), 235-249.
Maus M. V. et al. T cells expressing chimeric antigen receptors can cause anaphylaxis in humans, Cancer immunology research, 2013, 1(1), 26-31.

\* cited by examiner

METHOD FOR GENERATING T-CELLS COMPATIBLE FOR ALLOGENIC TRANSPLANTATION

CROSS REFERENCE TO RELATED APPLICATIONS

This application is a divisional of U.S. application Ser. No. 16/138,908 filed on Sep. 21, 2018, which is a divisional of U.S. application Ser. No. 15/123,974 filed on Sep. 6, 2016 now abandoned, which is a U.S. National Stage of PCT/EP2015/055097 filed on Mar. 11, 2015, which claims the benefit of Danish Application PA201470119 filed on Mar. 11, 2014, all of which are herein incorporated by reference in their entirety.

The instant application contains a Sequence Listing which has been submitted electronically in XML format and is hereby incorporated by reference in its entirety. Said XML copy, created on Sep. 28, 2023, is named D12013-25US3_SL.xml and is 155,648 bytes in size.

FIELD OF THE INVENTION

The present invention pertains to engineered T-cells, method for their preparation and their use as medicament, particularly for immunotherapy. The engineered T-cells of the invention are characterized in that the expression of beta 2-microglobulin (B2M) and/or class II major histocompatibility complex transactivator (CIITA) is inhibited, e.g., by using rare-cutting endonucleases able to selectively inactivating by DNA cleavage the gene encoding B2M and/or CIITA, or by using nucleic acid molecules which inhibit the expression of B2M and/or CIITA. In order to further render the T-cell non-alloreactive, at least one gene encoding a component of the T-cell receptor is inactivated, e.g., by using a rare-cutting endonucleases able to selectively inactivating by DNA cleavage the gene encoding said TCR component. In addition, a step of expression of immunosuppressive polypeptide such as viral MHCI homolog or NKG2D ligand can be performed on those modified T-cells in order to prolong the survival of these modified T cells in host organism. Such modified T-cell is particularly suitable for allogeneic transplantations, especially because it reduces both the risk of rejection by the host's immune system and the risk of developing graft versus host disease. The invention opens the way to standard and affordable adoptive immunotherapy strategies using T-Cells for treating cancer, infections and auto-immune diseases.

BACKGROUND OF THE INVENTION

Adoptive immunotherapy, which involves the transfer of autologous antigen-specific T-cells generated ex vivo, is a promising strategy to treat viral infections and cancer. The T-cells used for adoptive immunotherapy can be generated either by expansion of antigen-specific T-cells or redirection of T-cells through genetic engineering (Park, Rosenberg et al. 2011).

Novel specificities in T cells have been successfully generated through the genetic transfer of transgenic T cell receptors or chimeric antigen receptors (CARs) (Jena, Dotti et al. 2010). CARs are synthetic receptors consisting of a targeting moiety that is associated with one or more signaling domains in a single fusion molecule. In general, the binding moiety of a CAR consists of an antigen-binding domain of a single-chain antibody (scFv), comprising the light and variable fragments of a monoclonal antibody joined by a flexible linker. Binding moieties based on receptor or ligand domains have also been used successfully. The signaling domains for first generation CARs are derived from the cytoplasmic region of the CD3zeta or the Fc receptor gamma chains. First generation CARs have been shown to successfully redirect T-cell cytotoxicity, however, they failed to provide prolonged expansion and anti-tumor activity in vivo. Signaling domains from co-stimulatory molecules including CD28, OX-40 (CD134), and 4-1BB (CD137) have been added alone (second generation) or in combination (third generation) to enhance survival and increase proliferation of CAR modified T cells. CARs have successfully allowed T cells to be redirected against antigens expressed at the surface of tumor cells from various malignancies including lymphomas and solid tumors (Jena, Dotti et al. 2010).

The current protocol for treatment of patients using adoptive immunotherapy is based on autologous cell transfer. In this approach, T lymphocytes are recovered from patients, genetically modified or selected ex vivo, cultivated in vitro in order to amplify the number of cells if necessary and finally infused into the patient. In addition to lymphocyte infusion, the host may be manipulated in other ways that support the engraftment of the T cells or their participation in an immune response, for example pre-conditioning (with radiation or chemotherapy) and administration of lymphocyte growth factors (such as IL-2). Each patient receives an individually fabricated treatment, using the patient's own lymphocytes (i.e. an autologous therapy). Autologous therapies face substantial technical and logistic hurdles to practical application, their generation requires expensive dedicated facilities and expert personnel, they must be generated in a short time following a patient's diagnosis, and in many cases, pretreatment of the patient has resulted in degraded immune function, such that the patient's lymphocytes may be poorly functional and present in very low numbers. Because of these hurdles, each patient's autologous cell preparation is effectively a new product, resulting in substantial variations in efficacy and safety.

Ideally, one would like to use a standardized therapy in which allogeneic therapeutic cells could be pre-manufactured, characterized in detail, and available for immediate administration to patients. By allogeneic it is meant that the cells are obtained from individuals belonging to the same species but are genetically dissimilar. However, the use of allogeneic cells presently has many drawbacks. In immune-competent hosts allogeneic cells are rapidly rejected, a process termed host versus graft rejection (HvG), and this substantially limits the efficacy of the transferred cells. In immune-incompetent hosts, allogeneic cells are able to engraft, but their endogenous T-cell receptors (TCR) specificities may recognize the host tissue as foreign, resulting in graft versus host disease (GvHD), which can lead to serious tissue damage and death.

In order to provide allogeneic T-cells, the inventors previously disclosed a method to genetically engineer T-Cells, in which different effector genes, in particular those encoding T-cell receptors, were inactivated by using specific TAL-nucleases, better known under the trade mark TALEN T™ (Cellectis, 8, rue de la Croix Jarry, 75013 PARIS). This method has proven to be highly efficient in primary cells using RNA transfection as part of a platform allowing the mass production of allogeneic T-cells (WO 2013/176915).

Beta-2 microglobulin, also known as B2M, is the light chain of MHC class I molecules, and as such an integral part of the major histocompatibility complex In human, B2M is encoded by the b2m gene which is located on chromosome 15, opposed to the other MHC genes which are located as gene cluster on chromosome 6. The human protein is composed of 119 amino acids (SEQ ID NO: 1) and has a molecular weight of 11.800 Daltons. Mice models deficient for beta-2 microglobulin have shown that B2M is necessary for cell surface expression of MHC class I and stability of the peptide binding groove. It was further shown that hemopoietic transplants from mice that are deficient for normal cell-surface MHC I expression are rejected by NK1.1+ cells in normal mice because of a targeted mutation in the beta-2 microglobulin gene, suggesting that deficient expression of MHC I molecules renders marrow cells susceptible to rejection by the host immune system (Bix et al. 1991).

CIITA protein (SEQ ID NO: 4—NCBI Reference Sequence: NP_000237.2) that acts as a positive regulator of class II major histocompatibility complex gene transcription, including β2m gene transcription, and is often referred to as the "master control factor" for the expression of these genes. CIITA mRNA (SEQ ID NO: 5) can only be detected in human leukocyte antigen (HLA) system class II-positive cell lines and tissues. This highly restricted tissue distribution suggests that expression of HLA class II genes is to a large extent under the control of CIITA (Mach B., et al. 1994).

Adaptive immune response is a complex biological system where numerous cellular components interact. Professional Antigen Presenting Cells (APC) are able to process foreign bodies and expose them to helper T cells in the context of MHC Class II molecules. Activated helper T cells will in turn stimulate B cells response and cytotoxic T (CTL) cells response. CTL recognize foreign peptides presented by MHC Class I molecules but in the case of alloreactivity, recognize and kill cells bearing foreign MHC Class I. MHC Class I molecules are composed of 2 entities: the highly polymorphic, transmembrane heavy chain and a small invariant polypeptide, the beta2-microglobuline (beta2-m) encoded by B2M gene. The expression of the MHC Class I heavy chain at the cell surface requires its association with the beta2-m. Hence, abrogation of beta2-m expression in CART cells will impair MHC Class I expression and make them invisible to host CTL. However, MHC Class I deficient CART cells are susceptible to lysis by host NK cells, which target cells lacking MHC Class I molecules [Ljunggren H G et al. (1990), Immunl Today. 11:237-244].

NK cells exert cytotoxic functions towards the cells they interact with based on the balance between activating and inhibitory signals they received through different monomorphic or polymorphic receptors. One central activating receptor on human NK cells is NKG2D and its ligands include proteins such as MICA, MICB, ULBP1, ULBP2, ULBP3 [Raulet D H, (2003), Nature Reviews Immunology 3 (10): 781-79]. On the other hand, the inhibitory signal is mediated through the interaction between NK receptors like LIR-1/ILT2 and MHC Class I molecules [Ljunggren H G et al. (1990), Immunl Today. 11:237-244]. Some viruses such as cytomegaloviruses have acquired mechanisms to avoid NK cell mediate immune surveillance. HCMV genome encodes proteins that are able to prevent MHC Class I surface expression (i.e. US2, US3, US6 and US11) while expressing a MHC class I homolog protein (UL18) that acts as a decoy to block NK-mediated cell lysis [Kim, Y et al. (2008), PLOS Pathogens. 4: e1000123, and Wilkinson G. et al. (2010). J Clin Virol. 41(3):206-212]. Moreover, HCMV interferes with the NKG2D pathway by secreting a protein able to bind NKG2D ligands and prevent their surface expression [Welte S A et al. (2003), Eur J Immunol 33 (1): 194-203]. In tumor cells, some mechanisms have evolved to evade NKG2D response by secreting NKG2D ligands such as ULBP2, MICB or MICA (Waldhauer I, Steinle A (2003). Proteolytic release of soluble UL16-binding protein 2 from tumor cells. Cancer Res 2006; 66(5): 2520-2526; Salih H R et al. (2006), Hum Immunol. 2006 March; 67(3):188-95; Salih H R et al. (2003) Blood. 2003 Aug. 15; 102(4):1389-96; Salih H R et al. (2002) J Immunol.; 169(8):4098-102].

The present inventor here provides strategies for immunotherapy by which T-cells, especially allogeneic T-cells, are made particular suitable for allogeneic transplantations, reducing the risk for host versus graft rejections and for developing graft versus host disease and to render the T cells "stealthy", in particular with respect to APC cells or NK cells.

SUMMARY OF THE INVENTION

The present invention concerns methods for preparing engineered T-cells, in particular allogeneic T-cells obtained from a donor, to make them suitable for immunotherapy purposes. The methods of the present invention more particularly allow the precise modulation of expression of certain effector molecules important for immune recognition and histocompatibility.

According to one aspect, the present invention provides a method for preparing an engineered T-cell, preferably an allogeneic T-cell obtained from a donor, comprising the steps of:
 a) providing a T-cell, preferably an allogeneic T-cell obtained from a donor; and
 b) inhibiting the expression of beta 2-microglobulin (B2M) and/or class II major histocompatibility complex transactivator (CIITA) in said T-cell.

According to certain embodiments, inhibition of expression of B2M is achieved by a genome modification, more particularly through the expression in the T-cell of a rare-cutting endonuclease able to selectively inactivate by DNA cleavage the gene encoding B2M, such as the human β2m gene set forth in SEQ ID NO: 2 (NCBI Reference Sequence: NG_012920.1), or a gene having at least 70%, such as at least 80%, at least 90% at least 95%, or at least 99%, sequence identify with the human β2m gene set forth in SEQ ID NO: 2 over the entire length of SEQ ID NO: 2. Such rare-cutting endonuclease may be a TAL-nuclease, meganuclease, zing-finger nuclease (ZFN), or RNA guided endonuclease (such as Cas9).

According to certain other embodiments, inhibition of expression of B2M is achieved by using (e.g., introducing into the T-cell) a nucleic acid molecule that specifically hybridizes (e.g. binds) under cellular conditions with the cellular mRNA and/or genomic DNA encoding B2M, thereby inhibiting transcription and/or translation of the gene. In accordance with particular embodiments, the inhibition of expression of B2M is achieved by using ((e.g., introducing into the T-cell) an antisense oligonucleotide, ribozyme or interfering RNA (RNAi) molecule. Preferably, such nucleic acid molecule comprises at least 10 consecutive nucleotides of the complement of SEQ ID NO: 3 (i.e., the mRNA encoding human B2M; NCBI Reference Sequence: NM_004048).

According to certain embodiments, inhibition of expression of CIITA is achieved by a genome modification, more particularly through the expression in the T-cell of a rare-cutting endonuclease able to selectively inactivate by DNA cleavage the gene encoding CIITA, such as the human CIITA gene (NCBI Reference Sequence: NG_009628.1), or a gene having at least 70%, such as at least 80%, at least 90% at least 95%, or at least 99%, sequence identify with the human CIITA gene according to NG_009628.1 over the entire length of the human CIITA gene according to NG_009628.1. Such rare-cutting endonuclease may be a TAL-nuclease, meganuclease, zing-finger nuclease (ZFN), or RNA guided endonuclease (such as Cas9).

According to certain other embodiments, inhibition of expression of CIITA is achieved by using (e.g., introducing into the T-cell) a nucleic acid molecule that specifically hybridizes (e.g. binds) under cellular conditions with the cellular mRNA and/or genomic DNA encoding CIITA, thereby inhibiting transcription and/or translation of the gene. In accordance with particular embodiments, the inhibition of expression of CIITA is achieved by using ((e.g., introducing into the T-cell) an antisense oligonucleotide, ribozyme or interfering RNA (RNAi) molecule. Preferably, such nucleic acid molecule comprises at least 10 consecutive nucleotides of the complement of SEQ ID NO: 5 (i.e., the mRNA encoding human CIITA isoform 2).

According to particular embodiments, the T-cell may be further engineered to make it non-alloreactive, especially by inactivating one or more genes involved in self-recognition, such as those, for instance, encoding components of T-cell receptors (TCR). This can be achieved by a genome modification, more particularly through the expression in the T-cell of a rare-cutting endonuclease able to selectively inactivate by DNA cleavage, preferably double-strand break, at least one gene encoding a component of the T-Cell receptor (TCR), such as the gene encoding TCR alpha or TCR beta. Such rare-cutting endonuclease may be a TAL-nuclease, meganuclease, zing-finger nuclease (ZFN), or RNA guided endonuclease (such as, Cas9). Preferably, the rare-cutting endonuclease is able to selectively inactivate by DNA cleavage the gene coding for TCR alpha.

According to optional embodiments, the T-cell may be further engineered to express a Chimeric Antigen Receptor (CAR) directed against at least one antigen expressed at the surface of a malignant or infected cell, such as the B-lymphocyte antigen CD19.

The present invention thus provides in a further aspect engineered T-cells, in particular engineered isolated T-cells, characterized in that the expression of beta 2-microglobulin (B2M) is inhibited.

According to certain embodiments, a T-cell is provided which expresses a rare-cutting endonuclease able to selectively inactivate by DNA cleavage the gene encoding B2M. More particularly, such T-cell comprises an exogenous nucleic acid molecule comprising a nucleotide sequence encoding said rare-cutting endonuclease, which may be a TAL-nuclease, meganuclease, zing-finger nuclease (ZFN), or RNA guided endonuclease.

According to certain other embodiments, a T-cell is provided which comprises an exogenous nucleic acid molecule that inhibits the expression of B2M. According to particular embodiments, such nucleic acid molecule is an antisense oligonucleotide, ribozyme or interfering RNA (RNAi) molecule. According to preferred embodiments, such nucleic acid molecule comprises at least 10 consecutive nucleotides of the complement of SEQ ID NO: 3.

The present invention further provides engineered T-cells, in particular engineered isolated T-cells, characterized in that the expression of class II major histocompatibility complex transactivator (CIITA) is inhibited.

According to certain embodiments, a T-cell is provided which expresses a rare-cutting endonuclease able to selectively inactivate by DNA cleavage the gene encoding CIITA. More particularly, such T-cell comprises an exogenous nucleic acid molecule comprising a nucleotide sequence encoding said rare-cutting endonuclease, which may be a TAL-nuclease, meganuclease, zing-finger nuclease (ZFN), or RNA guided endonuclease.

According to certain other embodiments, a T-cell is provided which comprises an exogenous nucleic acid molecule that inhibits the expression of CIITA. According to particular embodiments, such nucleic acid molecule is an antisense oligonucleotide, ribozyme or interfering RNA (RNAi) molecule. According to preferred embodiments, such nucleic acid molecule comprises at least 10 consecutive nucleotides of the complement of SEQ ID NO: 5.

According to particular embodiments, the T-cell may further have at least one inactivated gene encoding a component of the TCR receptor. More particularly, such T-cell may express a rare-cutting endonuclease able to selectively inactivate by DNA cleavage, preferably double-strand break, said at least one gene encoding a component of the T-Cell receptor (TCR). Accordingly, said T-cell may comprise an exogenous nucleic acid molecule comprising a nucleotide sequence coding for a rare-cutting endonuclease able to selectively inactivate by DNA cleavage at least one gene coding for one component of the T-Cell receptor (TCR). The disruption of TCR provides a non-alloreactive T-cell that can be used in allogeneic treatment strategies.

According to optional embodiments, the T-cell may be engineered to express a Chimeric Antigen Receptor (CAR) directed against at least one antigen expressed at the surface of a malignant or infected cell, such as the B-lymphocyte antigen CD19. Particularly, the T-cell comprises an exogenous nucleic acid molecule comprising a nucleotide sequence encoding said CAR. The binding of the target antigen by the CAR has the effect of triggering an immune response by the T-cell directed against the pathological cell, which results in degranulation of various cytokine and degradation enzymes in the interspace between the cells.

According to some embodiments, an additional modification of T-cells is performed to render them stealthy by expression of at least one non-endogenous immunosuppressive polypeptide such as a viral MHC homolog, for instance, UL18, or such as a NKG2D ligand.

According to some embodiments, the T-cell of the present invention expresses at least one non-endogenous immune-suppressive polypeptide. According to more particular embodiments, said non-endogenous immune-suppressive polypeptide is a viral MHC homolog, such as UL18. The T-cell may comprise an exogenous nucleic acid molecule comprising a nucleotide sequence cording for a polypeptide sharing at least 80%, preferably at least 90% and more preferably at least 95% of identity with SEQ ID NO: 89. According to other more particular embodiments, said non-endogenous immune-suppressive polypeptide is a NKG2D ligand. The T-cell may comprise an exogenous nucleic acid molecule comprising a nucleotide sequence cording for a polypeptide sharing at least 80%, preferably at least 90% and more preferably at least 95% of identity with any one of SEQ ID NO: 90-97.

As a result of the present invention, engineered T-cells can be used as therapeutic products, ideally as an "off the shelf" product, for use in the treatment or prevention cancer, bacterial or viral infections, or auto-immune diseases.

Thus, the present invention further provides an engineered T-cell or a composition, such as a pharmaceutical composition, comprising same for use as a medicament. According to certain embodiments, the engineered T-cell or composition is for use in the treatment of a cancer, and more particularly for use in the treatment of lymphoma. According to certain other embodiments, the engineered T-cell or composition is for use in the treatment of viral infection. According to certain other embodiments, the engineered T-cell or composition is for use in the treatment of bacterial infection.

It is understood that the details given herein with respect to one aspect of the invention also apply to any of the other aspects of the invention.

DETAILED DESCRIPTION OF THE INVENTION

Figure 1:
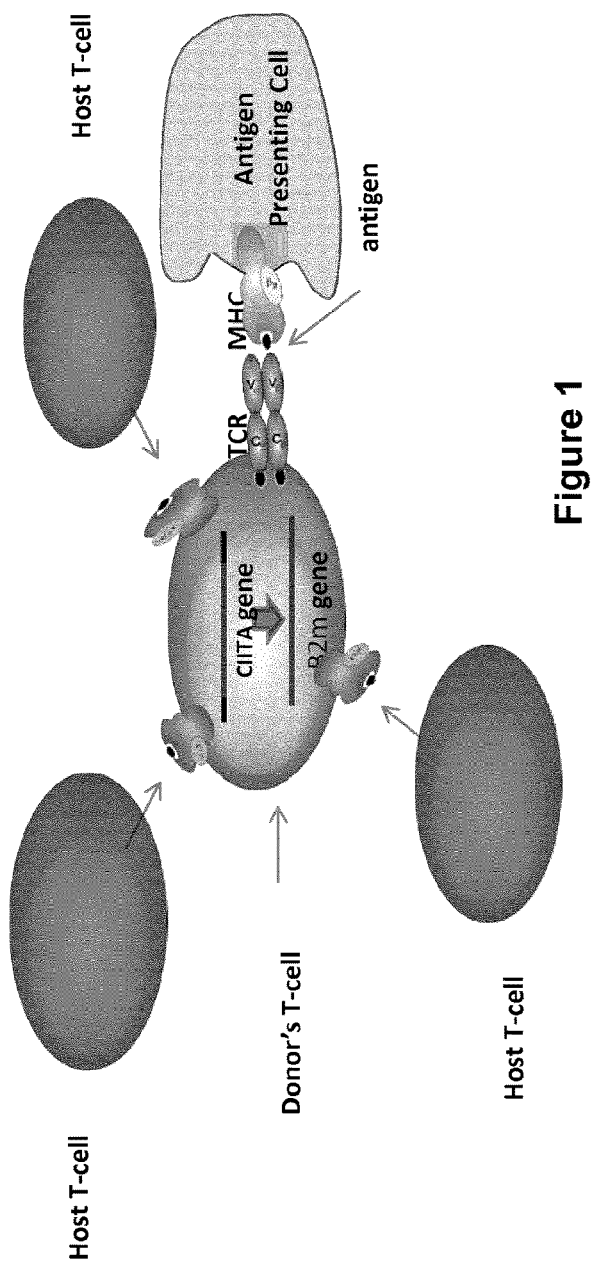
FIG. 1: Schematic representation of the normal relationship between donor's T-cells, host T-cells and antigen presenting cells.
Figure 2:
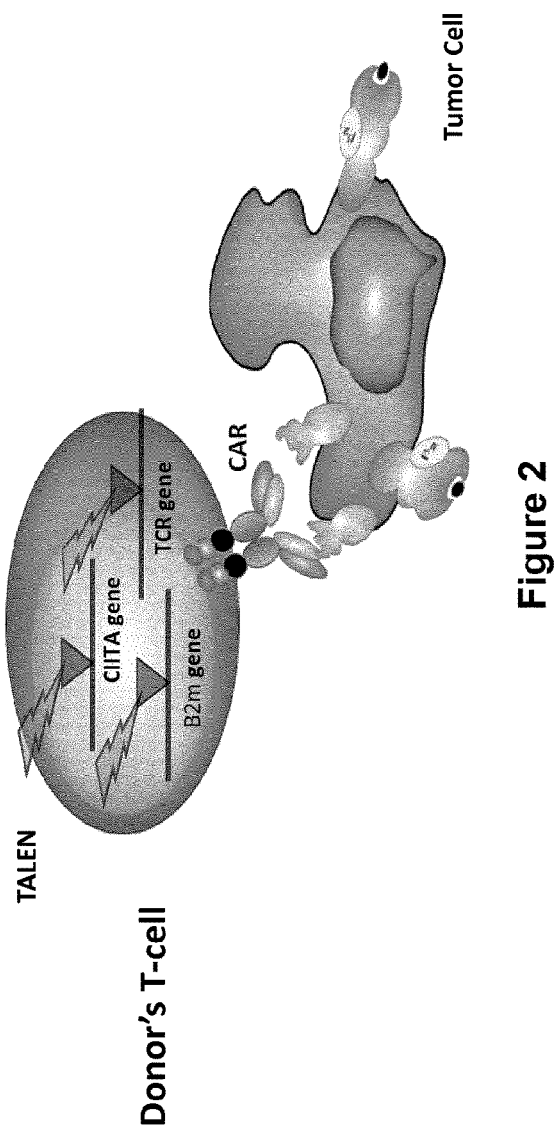
FIG. 2: Schematic representation of the genetically modified therapeutic T-cells according to the invention and the patient's T-cells and tumor cells.

Unless specifically defined herein, all technical and scientific terms used have the same meaning as commonly understood by a skilled artisan in the fields of gene therapy, biochemistry, genetics, and molecular biology.

All methods and materials similar or equivalent to those described herein can be used in the practice or testing of the present invention, with suitable methods and materials being described herein. All publications, patent applications, patents, and other references mentioned herein are incorporated by reference in their entirety. In case of conflict, the present specification, including definitions, will prevail. Further, the materials, methods, and examples are illustrative only and are not intended to be limiting, unless otherwise specified.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Current Protocols in Molecular Biology (Frederick M. AUSUBEL, 2000, Wiley and son Inc, Library of Congress, USA); Molecular Cloning: A Laboratory Manual, Third Edition, (Sambrook et al, 2001, Cold Spring Harbor, New York: Cold Spring Harbor Laboratory Press); Oligonucleotide Synthesis (M. J. Gait ed., 1984); Mullis et al. U.S. Pat. No. 4,683,195; Nucleic Acid Hybridization (B. D. Harries & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the series, Methods In ENZYMOLOGY (J. Abelson and M. Simon, eds.-in-chief, Academic Press, Inc., New York), specifically, Vols. 154 and 155 (Wu et al. eds.) and Vol. 185, "Gene Expression Technology" (D. Goeddel, ed.); Gene Transfer Vectors For Mammalian Cells (J. H. Miller and M. P. Calos eds., 1987, Cold Spring Harbor Laboratory); Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); and Manipulating the Mouse Embryo, (Cold Spring Harbor Laboratory Press, Cold Spring Harbor, N.Y., 1986).

Methods for Preparing Engineered T-Cells

In a general aspect, the present invention pertains to methods for preparing engineered T-cells, in particular allogeneic T-cells obtained from a donor.

Accordingly, the present invention provides a method for preparing an engineered T-cell, preferably an allogeneic T-cell obtained from a donor, said method comprises the steps of:
- a) providing a T-cell, preferably an allogeneic T-cell obtained from a donor; and
- b) inhibiting the expression of beta 2-microglobulin (B2M) and/or class II major histocompatibility complex transactivator (CIITA) in said T-cell.

According to certain embodiments, the method comprises inhibiting the expression of beta 2-microglobulin (B2M). Alternatively, or in addition, the method may comprise inhibiting the expression of class II major histocompatibility complex transactivator (CIITA).

According to certain embodiments, inhibition of expression of B2M is achieved by a genome modification, more particularly through the expression in the T-cell of a rare-cutting endonuclease able to selectively inactivate by DNA cleavage the gene encoding B2M (e.g. the human β2m gene set forth in SEQ ID NO: 2).

According to certain other embodiments, inhibition of expression of CIITA is achieved by a genome modification, more particularly through the expression in the T-cell of a rare-cutting endonuclease able to selectively inactivate by DNA cleavage the gene encoding CIITA (e.g. the human CIITA gene).

By "inactivating" or "inactivation of" a gene it is intended that the gene of interest (e.g. the gene encoding B2M or CIITA) is not expressed in a functional protein form. In particular embodiments, the genetic modification of the method relies on the expression, in provided cells to engineer, of a rare-cutting endonuclease such that same catalyzes cleavage in one targeted gene thereby inactivating said targeted gene. The nucleic acid strand breaks caused by the endonuclease are commonly repaired through the distinct mechanisms of homologous recombination or non-homologous end joining (NHEJ). However, NHEJ is an imperfect repair process that often results in changes to the DNA sequence at the site of the cleavage. Mechanisms involve rejoining of what remains of the two DNA ends through direct re-ligation (Critchlow and Jackson 1998) or via the so-called microhomology-mediated end joining (Betts, Brenchley et al. 2003; Ma, Kim et al. 2003). Repair via non-homologous end joining (NHEJ) often results in small insertions or deletions and can be used for the creation of specific gene knockouts. Said modification may be a substitution, deletion, or addition of at least one nucleotide. Cells in which a cleavage-induced mutagenesis event, i.e. a mutagenesis event consecutive to an NHEJ event, has occurred can be identified and/or selected by well-known method in the art.

A rare-cutting endonuclease to be used in accordance of the present invention to inactivate the β2m gene may, for instance, be a TAL-nuclease, meganuclease, zing-finger nuclease (ZFN), or RNA guided endonuclease (such as Cas9).

According to a particular embodiment, the rare-cutting endonuclease is a TAL-nuclease.

According to another particular embodiment, the rate-cutting endonuclease is a homing endonuclease, also known under the name of meganuclease.

According to another particular embodiment, the rare-cutting endonuclease is a zing-finger nuclease (ZNF).

According to another particular embodiment, the rare-cutting endonuclease is a RNA guided endonuclease. According to a preferred embodiment, the RNA guided endonuclease is the Cas9/CRISPR complex.

According to a specific embodiment, the rare-cutting endonuclease is a TAL-nuclease encoded by a nucleic acid molecule comprising the nucleotide sequence set for in SEQ ID NO: 67. According to another specific embodiment, the rare-cutting endonuclease is a TAL-nuclease encoded by a nucleic acid molecule comprising the nucleotide sequence set for in SEQ ID NO: 68. In yet another specific embodiment, the rare-cutting endonuclease is a combination of a TAL-nuclease encoded by a nucleic acid molecule comprising the nucleotide sequence set for in SEQ ID NO: 67 and a TAL-nuclease encoded by a nucleic acid molecule comprising the nucleotide sequence set for in SEQ ID NO: 68.

In order to be expressed in the T-cell, said rare-cutting endonuclease may be introduced into the cell by way of an exogenous nucleic acid molecule comprising a nucleotide sequence encoding said rare-cutting endonuclease. According to particular embodiments, the method of the invention further comprises introducing into said T-cell an exogenous nucleic acid molecule comprising a nucleotide sequence coding for a rare-cutting endonuclease, preferably a rare-cutting endonuclease able to selectively inactivate by DNA cleavage the gene encoding B2M (e.g. the human β2m gene set forth in SEQ ID NO: 2). For example, the exogenous nucleic acid molecule may comprising the nucleotide sequence set for in SEQ ID NO: 67 or SEQ ID NO: 68.

As a result, an engineered T-cell is obtained which expresses a rare-cutting endonuclease, preferably a rare-cutting endonuclease able to selectively inactivate by DNA cleavage the gene encoding B2M. In consequence, inactivation of the B2M gene by said rare-cutting endonuclease leads to the inhibition of the expression of B2M in the engineered T-cell. Hence, an engineered T-cell is obtained which is characterized in that the expression of B2M is inhibited.

A rare-cutting endonuclease to be used in accordance of the present invention to inactivate the CIITA gene may, for instance, be a TAL-nuclease, meganuclease, zing-finger nuclease (ZFN), or RNA guided endonuclease (such as Cas9).

According to a particular embodiment, the rare-cutting endonuclease is a TAL-nuclease.

According to another particular embodiment, the rate-cutting endonuclease is a homing endonuclease, also known under the name of meganuclease.

According to another particular embodiment, the rare-cutting endonuclease is a zing-finger nuclease (ZNF).

According to another particular embodiment, the rare-cutting endonuclease is a RNA guided endonuclease. According to a preferred embodiment, the RNA guided endonuclease is the Cas9/CRISPR complex.

In order to be expressed in the T-cell, said rare-cutting endonuclease may be introduced into the cell by way of an exogenous nucleic acid molecule comprising a nucleotide sequence encoding said rare-cutting endonuclease. According to particular embodiments, the method of the invention further comprises introducing into said T-cell an exogenous nucleic acid molecule comprising a nucleotide sequence coding for a rare-cutting endonuclease, preferably a rare-cutting endonuclease able to selectively inactivate by DNA cleavage the gene encoding CIITA (e.g. the human CIITA gene).

As a result, an engineered T-cell is obtained which expresses a rare-cutting endonuclease, preferably a rare-cutting endonuclease able to selectively inactivate by DNA cleavage the gene encoding CIITA. In consequence, inactivation of the CIITA gene by said rare-cutting endonuclease leads to the inhibition of the expression of CIITA in the engineered T-cell. Hence, an engineered T-cell is obtained which is characterized in that the expression of CIITA is inhibited. According to certain other embodiments, inhibition of expression of B2M is achieved by using (e.g., introducing into the T-cell) a nucleic acid molecule that specifically hybridizes (e.g. binds) under cellular conditions with the cellular mRNA and/or genomic DNA encoding B2M, thereby inhibiting transcription and/or translation of the gene. In accordance with particular embodiments, the inhibition of expression of B2M is achieved by using (e.g., introducing into the T-cell) an antisense oligonucleotide, ribozyme or interfering RNA (RNAi) molecule.

According to a particular embodiment, the nucleic acid molecule is an antisense oligonucleotide.

According to other particular embodiments, the nucleic acid molecule is a ribozyme, preferably a hammerhead ribozyme.

According to other particular embodiments, the nucleic acid is an interfering RNA (RNAi) molecule, such as a micro RNA (miRNA), small interfering RNA (siRNA) or short hairpin RNA (shRNA). Hence, in accordance with a preferred embodiment, the nucleic acid molecule is a micro RNA. In accordance with another preferred embodiment, the nucleic acid molecule is a small interfering RNA. In accordance with another preferred embodiment, the nucleic acid molecule is a short hairpin RNA.

As a result, an engineered T-cell is obtained which is characterized in that the expression of B2M is inhibited.

Because B2M is an important structural component of the major histocompatibility complex (MHC), inhibition of B2M expression leads to a reduction or elimination of MHC molecules on the surface of the engineered T-cell. In consequence, the engineered T-cell no longer presents antigens on the surface which are recognized by CD8+ cells. Especially in case of an allogeneic T-cell obtained from a donor, reduction or elimination of nonself-antigen presenting MHC molecules on the surface of the T-cell prevents the engineered T-cell, when infused into an allogeneic host, from being recognized by the host CD8+ cells. This makes the engineered T-cell particular suitable for allogeneic transplantations, especially because it reduces the risk of rejection by the host's immune system.

According to certain other embodiments, inhibition of expression of CIITA is achieved by using (e.g., introducing into the T-cell) a nucleic acid molecule that specifically hybridizes (e.g. binds) under cellular conditions with the cellular mRNA and/or genomic DNA encoding CIITA, thereby inhibiting transcription and/or translation of the gene. In accordance with particular embodiments, the inhibition of expression of CIITA is achieved by using (e.g., introducing into the T-cell) an antisense oligonucleotide, ribozyme or interfering RNA (RNAi) molecule.

According to a particular embodiment, the nucleic acid molecule is an antisense oligonucleotide.

According to other particular embodiment, the nucleic acid molecule is a ribozyme, preferably a hammerhead ribozyme.

According to other particular embodiments, the nucleic acid is an interfering RNA (RNAi) molecule, such as a micro RNA (miRNA), small interfering RNA (siRNA) or short hairpin RNA (shRNA). Hence, in accordance with a preferred embodiment, the nucleic acid molecule is a micro RNA. In accordance with another preferred embodiment, the nucleic acid molecule is a small interfering RNA. In accordance with another preferred embodiment, the nucleic acid molecule is a short hairpin RNA.

As a result, an engineered T-cell is obtained which is characterized in that the expression of CIITA is inhibited. It is also contemplated by the present invention that the engineered T-cell of the present invention does not express a functional T-cell receptor (TCR) on its cell surface. T-cell receptors are cell surface receptors that participate in the activation of T cells in response to the presentation of antigen. The TCR is generally made from two chains, alpha and beta, which assemble to form a heterodimer and associates with the CD3-transducing subunits to form the T-cell receptor complex present on the cell surface. Each alpha and beta chain of the TCR consists of an immunoglobulin-like N-terminal variable (V) and constant (C) region, a hydrophobic transmembrane domain, and a short cytoplasmic region. As for immunoglobulin molecules, the variable region of the alpha and beta chains are generated by V(D)J recombination, creating a large diversity of antigen specificities within the population of T cells. However, in contrast to immunoglobulins that recognize intact antigen, T-cells are activated by processed peptide fragments in association with an MHC molecule, introducing an extra dimension to antigen recognition by T cells, known as MHC restriction. Recognition of MHC disparities between the donor and recipient through the T-cell receptor leads to T-cell proliferation and the potential development of graft versus host disease (GVHD). It has been shown that normal surface expression of the TCR depends on the coordinated synthesis and assembly of all seven components of the complex (Ashwell and Klusner 1990). The inactivation of TCR alpha or TCR beta can result in the elimination of the TCR from the surface of T-cells preventing recognition of alloantigen and thus GVHD. The inactivation of at least one gene coding for a TCR component thus renders the engineered T-cell less alloreactive. By "inactivating" or "inactivation of" a gene it is meant that the gene of interest (e.g., at least one gene coding for a TCR component) is not expressed in a functional protein form.

Therefore, the method of the present invention in accordance with particular embodiments further comprises inactivating at least one gene encoding a component of the T-cell receptor. More particularly, the inactivation is achieved by using (e.g., introducing into the T-cell) a rare-cutting endonuclease able to selectively inactivate by DNA cleavage, preferably double-strand break, at least one gene encoding a component of the T-Cell receptor (TCR). According to particular embodiments, the rare-cutting endonuclease is able to selectively inactivate by DNA cleavage the gene coding for TCR alpha or TCR beta. According to a preferred embodiment, the rare-cutting endonuclease is able to selectively inactivate by DNA cleavage the gene coding for TCR alpha. Especially in case of an allogeneic T-cell obtained from a donor, inactivating of at least one gene encoding a component of TCR, notably TCR alpha, leads to engineered T-cells, when infused into an allogeneic host, which are non-alloreactive. This makes the engineered T-cell particular suitable for allogeneic transplantations, especially because it reduces the risk of graft versus host disease.

A rare-cutting endonuclease to be used in accordance of the present invention to inactivate at least one gene encoding a component of the T-cell receptor may, for instance, be a TAL-nuclease, meganuclease, zing-finger nuclease (ZFN), or RNA guided endonuclease (such as Cas9).

According to a particular embodiment, the rare-cutting endonuclease is a TAL-nuclease.

According to another particular embodiment, the rate-cutting endonuclease is a homing endonuclease, also known under the name of meganuclease.

According to another particular embodiment, the rare-cutting endonuclease is a zing-finger nuclease (ZNF).

According to another particular embodiment, the rare-cutting endonuclease is a RNA guided endonuclease. According to a preferred embodiment, the RNA guided endonuclease is the Cas9/CRISPR complex.

In order to be expressed in the T-cell, said rare-cutting endonuclease may be introduced into the cell by way of an exogenous nucleic acid molecule comprising a nucleotide sequence encoding said rare-cutting endonuclease. According to particular embodiments, the method of the invention further comprises introducing into said T-cell an exogenous nucleic acid molecule comprising a nucleotide sequence coding for a rare-cutting endonuclease able to selectively inactivate by DNA cleavage, preferably double-strand break, at least one gene encoding a component of the T-cell receptor (TCR).

As a result, an engineered T-cell is obtained which further expresses a rare-cutting endonuclease able to selectively inactivate by DNA cleavage at least one gene encoding a component of the T-cell receptor (TCR). In consequence, an engineered T-cell is obtained which is characterized in that at least at least one gene encoding a component of the T-cell receptor (TCR) is inactivated.

It is also contemplated by the present invention that the engineered T-cell further expresses a Chimeric Antigen Receptor (CAR) directed against at least one antigen expressed at the surface of a malignant or infected cell. Hence, in accordance with certain embodiments, the method of the invention furthers comprise introducing into said T-cell an exogenous nucleic acid molecule comprising a nucleotide sequence coding for a Chimeric Antigen Receptor (CAR) directed against at least one antigen expressed at the surface of a malignant or infected cell.

The T-cell to be modified according to the present invention may be any suitable T-cell. For example, the T-cell can be an inflammatory T-lymphocyte, cytotoxic T-lymphocyte, regulatory T-cell or helper T-lymphocyte. Particularly, the T-cell is a cytotoxic T-lymphocyte. In certain embodiments, said T-cell is selected from CD4+T-lymphocytes and CD8+ T-lymphoctyes. They can be extracted from blood or derived from stem cells. The stem cells can be adult stem cells, embryonic stem cells, more particularly non-human stem cells, cord blood stem cells, progenitor cells, bone marrow stem cells, induced pluripotent stem cells, totipotent stem cells or hematopoietic stem cells. Representative human cells are CD34+ cells. In particular embodiments, the T-cell to be modified according to the present invention is a human T-cell. Prior to expansion and genetic modification of the cells of the invention, a source of cells can be obtained from a subject, such as a patient, through a variety of non-limiting methods. T-cell can be obtained from a number of non-limiting sources, including peripheral blood mononuclear cells, bone marrow, lymph node tissue, cord blood, thymus tissue, tissue from a site of infection, ascites, pleural effusion, spleen tissue, and tumors. In certain embodiments of the present invention, any number of T cell lines available and known to those skilled in the art, may be used. In another embodiment, said cell can be derived from a healthy donor, from a patient diagnosed with cancer or from a patient diagnosed with an infection. In another embodiment, said cell is part of a mixed population of cells which present different phenotypic characteristics.

Rare-Cutting Endonuclease

In accordance with certain embodiments of the present invention, rare-cutting endonucleases are employed which are able to selectively inactivate by DNA cleavage the gene of interest, such as the gene encoding B2M.

The term "rare-cutting endonuclease" refers to a wild type or variant enzyme capable of catalyzing the hydrolysis (cleavage) of bonds between nucleic acids within a DNA or RNA molecule, preferably a DNA molecule. Particularly, said nuclease can be an endonuclease, more preferably a rare-cutting endonuclease which is highly specific, recognizing nucleic acid target sites ranging from to 45 base pairs (bp) in length, usually ranging from 10 to 35 base pairs in length, more usually from 12 to 20 base pairs. The endonuclease according to the present invention recognizes at specific polynucleotide sequences, further referred to as "target sequence" and cleaves nucleic acid inside these target sequences or into sequences adjacent thereto, depending on the molecular structure of said endonuclease. The rare-cutting endonuclease can recognize and generate a single- or double-strand break at specific polynucleotides sequences.

In particular embodiments, said rare-cutting endonuclease according to the present invention is a RNA-guided endonuclease such as the Cas9/CRISPR complex. RNA guided endonucleases constitute a new generation of genome engineering tool where an endonuclease associates with a RNA molecule. In this system, the RNA molecule nucleotide sequence determines the target specificity and activates the endonuclease (Gasiunas, Barrangou et al. 2012; Jinek, Chylinski et al. 2012; Cong, Ran et al. 2013; Mali, Yang et al. 2013). Cas9, also named Csn1 is a large protein that participates in both crRNA biogenesis and in the destruction of invading DNA. Cas9 has been described in different bacterial species such as S. thermophiles, Listeria innocua (Gasiunas, Barrangou et al. 2012; Jinek, Chylinski et al. 2012) and S. Pyogenes (Deltcheva, Chylinski et al. 2011). The large Cas9 protein (>1200 amino acids) contains two predicted nuclease domains, namely HNH (McrA-like) nuclease domain that is located in the middle of the protein and a splitted RuvC-like nuclease domain (RNase H fold). Cas9 variant can be a Cas9 endonuclease that does not naturally exist in nature and that is obtained by protein engineering or by random mutagenesis. Cas9 variants according to the invention can for example be obtained by mutations i.e. deletions from, or insertions or substitutions of at least one residue in the amino acid sequence of a S. pyogenes Cas9 endonuclease (COG3513).

In other particular embodiments, said rare-cutting endonuclease can also be a homing endonuclease, also known under the name of meganuclease. Such homing endonucleases are well-known to the art (Stoddard 2005). Homing endonucleases are highly specific, recognizing DNA target sites ranging from 12 to 45 base pairs (bp) in length, usually ranging from 14 to 40 bp in length. The homing endonuclease according to the invention may for example correspond to a LAGLIDADG endonuclease, to a HNH endonuclease, or to a GIY-YIG endonuclease. Preferred homing endonuclease according to the present invention can be an I-CreI variant. A "variant" endonuclease, i.e. an endonuclease that does not naturally exist in nature and that is obtained by genetic engineering or by random mutagenesis can bind DNA sequences different from that recognized by wild-type endonucleases (see international application WO2006/097854).

In other particular embodiments, said rare-cutting endonuclease can be a "Zinc Finger Nucleases" (ZFNs), which are generally a fusion between the cleavage domain of the type IIS restriction enzyme, FokI, and a DNA recognition domain containing 3 or more C2H2 zinc finger motifs. The heterodimerization at a particular position in the DNA of two individual ZFNs in precise orientation and spacing leads to a double-strand break (DSB) in the DNA. The use of such chimeric endonucleases have been extensively reported in the art as reviewed by Urnov et al. (Genome editing with engineered zinc finger nucleases (2010) *Nature reviews Genetics* 11:636-646). Standard ZFNs fuse the cleavage domain to the C-terminus of each zinc finger domain. In order to allow the two cleavage domains to dimerize and cleave DNA, the two individual ZFNs bind opposite strands of DNA with their C-termini a certain distance apart. The most commonly used linker sequences between the zinc finger domain and the cleavage domain requires the 5' edge of each binding site to be separated by 5 to 7 bp. The most straightforward method to generate new zinc-finger arrays is to combine smaller zinc-finger "modules" of known specificity. The most common modular assembly process involves combining three separate zinc fingers that can each recognize a 3 base pair DNA sequence to generate a 3-finger array that can recognize a 9 base pair target site. Numerous selection methods have been used to generate zinc-finger arrays capable of targeting desired sequences. Initial selection efforts utilized phage display to select proteins that bound a given DNA target from a large pool of partially randomized zinc-finger arrays. More recent efforts have utilized yeast one-hybrid systems, bacterial one-hybrid and two-hybrid systems, and mammalian cells.

In other particular embodiments, said rare-cutting endonuclease is a "TALE-nuclease" or a "MBBBD-nuclease" resulting from the fusion of a DNA binding domain typically derived from Transcription Activator Like Effector proteins (TALE) or from a Modular Base-per-Base Binding domain (MBBBD), with a catalytic domain having endonuclease activity. Such catalytic domain usually comes from enzymes, such as for instance I-TevI, ColE7, NucA and Fok-I. TALE-nuclease can be formed under monomeric or dimeric forms depending of the selected catalytic domain (WO2012138927). Such engineered TALE-nucleases are commercially available under the trade name TALEN™ (Cellectis, 8 rue de la Croix Jarry, 75013 Paris, France). In general, the DNA binding domain is derived from a Transcription Activator like Effector (TALE), wherein sequence specificity is driven by a series of 33-35 amino acids repeats originating from *Xanthomonas* or *Ralstonia* bacterial proteins AvrBs3, PthXo1, AvrHah1, PthA, Tal1c as non-limiting examples. These repeats differ essentially by two amino acids positions that specify an interaction with a base pair (Boch, Scholze et al. 2009; Moscou and Bogdanove 2009). Each base pair in the DNA target is contacted by a single repeat, with the specificity resulting from the two variant amino acids of the repeat (the so-called repeat variable dipeptide, RVD). TALE binding domains may further comprise an N-terminal translocation domain responsible for the requirement of a first thymine base (T0) of the targeted sequence and a C-terminal domain that containing a nuclear localization signals (NLS). A TALE nucleic acid binding domain generally corresponds to an engineered core TALE scaffold comprising a plurality of TALE repeat sequences, each repeat comprising a RVD specific to each nucleotides base of a TALE recognition site. In the present invention, each TALE repeat sequence of said core scaffold is made of 30 to 42 amino acids, more preferably 33 or 34 wherein two critical amino acids (the so-called repeat variable dipeptide, RVD) located at positions 12 and 13 mediates the recognition of one nucleotide of said TALE binding site sequence; equivalent two critical amino acids can be located at positions other than 12 and 13 specially in TALE repeat sequence taller than 33 or 34 amino acids long. Preferably, RVDs associated with recognition of the different nucleotides are HD for recognizing C, NG for recognizing T, NI for recognizing A, NN for recognizing G or A. In another embodiment, critical amino acids 12 and 13 can be mutated towards other amino acid residues in order to modulate their specificity towards nucleotides A, T, C and G and in particular to enhance this specificity. A TALE nucleic acid binding domain usually comprises between 8 and 30 TALE repeat sequences. More preferably, said core scaffold of the present invention comprises between 8 and 20 TALE repeat sequences; again more preferably 15 TALE repeat sequences. It can also comprise an additional single truncated TALE repeat sequence made of 20 amino acids located at the C-terminus of said set of TALE repeat sequences, i.e. an additional C-terminal half-TALE repeat sequence. Other modular base-per-base specific nucleic acid binding domains (MBBBD) are described in WO 2014/018601. Said MBBBD can be engineered, for instance, from newly identified proteins, namely EAV36_BURRH, E5AW43_BURRH, E5AW45_BURRH and E5AW46_BURRH proteins from the recently sequenced genome of the endosymbiont fungi *Burkholderia rhizoxinica*. These nucleic acid binding polypeptides comprise modules of about 31 to 33 amino acids that are base specific. These modules display less than 40% sequence identity with *Xanthomonas* TALE common repeats and present more polypeptides sequence variability. The different domains from the above proteins (modules, N and C-terminals) from *Burkholderia* and *Xanthomonas* are useful to engineer new proteins or scaffolds having binding properties to specific nucleic acid sequences and may be combined to form chimeric TALE-MBBBD proteins.

Inhibitory Nucleic Acid Molecules

In accordance with certain other embodiments of the present invention, nucleic acid molecules are employed which inhibit the expression of B2M. More particularly, the nucleic acid may be an antisense oligonucleotide, ribozyme or interfering RNA (RNAi) molecule. Preferably, such nucleic acid molecule comprises at least 10 consecutive nucleotides of the complement of SEQ ID NO: 3.

According to particular embodiments, the inhibitory nucleic acid is an antisense oligonucleotide which inhibits the expression of B2M. Such antisense oligonucleotide is an nucleic acid (either DNA or RNA) which specifically hybridizes (e.g. binds) under cellular conditions with the cellular mRNA and/or genomic DNA encoding B2M, thereby inhibiting transcription and/or translation of the gene. The binding may be by conventional base pair complementarity. Alternatively, the binding may be, for example, in case of binding to DNA duplexes, through specific interactions in the major groove of the double helix. Absolute complementarity, although preferred, is not required.

Also contemplated by the present invention is that nucleic acid molecules are employed which inhibit the expression of CIITA. More particularly, the nucleic acid may be an antisense oligonucleotide, ribozyme or interfering RNA (RNAi) molecule. Preferably, such nucleic acid molecule comprises at least consecutive nucleotides of the complement of SEQ ID NO: 5.

Antisense oligonucleotides employed according to the invention may be DNA or RNA or chimeric mixtures or derivatives or modified versions thereof, and may be single-stranded or double stranded. Thus, according to a preferred embodiment, the antisense oligonucleotide is a single-stranded or double-stranded DNA molecule, more preferably a double-stranded DNA molecule. According to another preferred embodiment, the antisense oligonucleotide is a single-stranded or double-stranded RNA molecule, more preferably a single-stranded RNA molecule.

According to preferred embodiments, the antisense oligonucleotide is a modified oligonucleotide which is resistant to endogenous nucleases, e.g., exonucleases and/or endonucleases, and is therefore stable in vivo and in vitro.

The antisense oligonucleotide may be modified at the base moiety, sugar moiety, or phosphate backbone, for example, to improve stability of the molecule. The antisense oligonucleotide may include other appended groups such as peptides (e.g., for targeting host cell receptors), or agents facilitating transport across the cell membrane. Hence, the antisense oligonucleotide may be conjugated to another molecule such as a peptide or transport agent.

According to particular embodiments, the antisense oligonucleotide comprises at least one modified base moiety which is selected from the group including, but not limited to, 5-fluorouracil, 5-bromouracil, 5-chlorouracil, 5-iodouracil, hypoxanthine, xanthine, 4-acetylcytosine, 5-(carboxyhydroxytriethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 3-(3-amino-3-N-2-carboxypropyl) uracil, (acp3)w and 2,6-diaminopurine.

According to other particular embodiments, the antisense oligonucleotide comprise at least one modified sugar moiety selected from the group including, but not limited to, arabinose, 2-fluoroarabinose, xylulose and hexose.

According to other particular embodiments, the antisense oligonucleotide comprises at least one modified phosphate backbone selected from the group including, but not limited to, a phosphorothioate, a phosphorodithioate, a phosphoramidothioate, a phosphoramidate, a phosphordiamidate, a methylphosphonate, an alkyl phosphotriester, and a formacetal or analog thereof.

An antisense oligonucleotide may be delivered into the cell, for example, in form of an expression vector, such as a plasmid or viral vector, which, when transcribed in the cells, produces RNA which is complementary to at least a unique portion of the cellular mRNA for B2M. Alternatively, the antisense oligonucleotide may be generated ex vivo and introduced into the cell by any known means in the art. The antisense oligonucleotide may be synthesise ex vivo by standard method known in the art, e.g., by use of an automated DNA synthesizer (such as automated DNA synthesizer are commercially available from, e.g., Applied Biosystems). A number of methods have been developed for delivering antisense DNA or RNA to cells, e.g. by direct injection or through modification designed to target the desired cell (e.g., using antisense oligonucleotides linked to peptides or antibodies that specifically bind receptors or antigens expressed on the target cell surface.

According to preferred embodiments, a recombinant DNA vector is used in which a nucleotide sequence coding for an antisense oligonucleotide inhibiting the expression of B2M or CIITA is placed under the control of a promoter, such as a strong pol III or pol II promoter. The use of such a construct to transfect a target cell, such as a T-cell, will result in the transcription of a sufficient amount of single-stranded RNA that will form complementary base pairs with the endogenous transcript and thereby prevent translation of the B2M or CIITA mRNA. In accordance with these embodiments, a DNA vector comprising the nucleotide sequence encoding the antisense oligonucleotide is introduced into the cell where the transcription of an antisense RNA occurs. Such vector can remain episomal or be chromosomally integrated, as long as it can be transcribed to produce the antisense RNA. The expression of the sequence encoding the antisense RNA can be by any promoter known in the art to act in mammalian, preferably human cells. Such promoter can be inducible or constitutive. Exemplary promoters include, but are not limited to, the SV40 early promoter region, the promoter containing the 3' long terminal repeat of Rous sarcoma virus, the herpes thymidine promoter, and the regulatory sequences of the methallothionein gene.

Alternatively, antisense cDNA constructs that synthesize antisense RNA constitutively or inducibly, depending on the promoter used, can be introduced into the cell.

According to preferred embodiments, the antisense oligonucleotide comprises at least 10 consecutive nucleotides of the complement of SEQ ID NO: 3. In case of a double stranded molecule, such double-stranded antisense oligonucleotide comprises a first strand comprising at least 10 consecutive nucleotide of SEQ ID NO: 3, and a second strand complementary to said first strand. In case of a single-stranded molecule, such single-stranded oligonucleotide comprises at least 10 consecutive nucleotides of the complement of SEQ ID NO: 3.

According to other preferred embodiments, the antisense oligonucleotide comprises at least 10 consecutive nucleotides of the complement of SEQ ID NO: 5. In case of a double stranded molecule, such double-stranded antisense oligonucleotide comprises a first strand comprising at least 10 consecutive nucleotide of SEQ ID NO: 5, and a second strand complementary to said first strand. In case of a single-stranded molecule, such single-stranded oligonucleotide comprises at least 10 consecutive nucleotides of the complement of SEQ ID NO: 5.

The antisense oligonucleotide may comprise a nucleotide sequence complementary to a non-coding or a coding region of the B2M or CIITA mRNA. According to preferred embodiments, the antisense oligonucleotide comprises a nucleotide sequence complementary to the 5' end of the B2M or CIITA mRNA, e.g., the 5' untranslated sequence up to and including the AUG initiation codon. According to other preferred embodiments, the antisense oligonucleotide comprises a nucleotide sequence complementary to the 3' untranslated sequence of the B2M or CIITA mRNA. According to other preferred embodiments, the antisense oligonucleotide comprises a nucleotide sequence complementary to the coding region of the B2M or CIITA mRNA. Whether designed to hybridize to the 3' or coding region of the B2M or CIITA mRNA, an antisense oligonucleotide should be at least six nucleotides in length, preferably at least 10 nucleotide in length, and is preferably less than about 100, and more preferably less than about 50, 25, 20, 15 or 10 nucleotides in length. According to preferred embodiments, the antisense oligonucleotide is 6 to 25, such as 10 to 25 nucleotides in length.

In accordance with other particular embodiments, a ribozyme molecule designed to catalytically cleave the B2M or CIITA mRNA transcript is used to prevent translation and expression of B2M or CIITA in the T-cell, respectively (see, e.g., WO 90/11364 and U.S. Pat. No. 5,093,246 for general guidance). According to preferred embodiments, the ribozyme is a hammerhead ribozyme. Hammerhead ribozymes cleave mRNAs at locations dictated by flanking regions that form complementary base pairs with the target mRNA, e.g. the B2M mRNA, such as the human B2M mRNA set forth in SEQ ID NO: 3. The sole requirement is that the target mRNA has the following sequence of two bases: 5'-UG-3'. The constructions and production of hammerhead ribozymes is well known in the art and is described in more detail in Haseloff and Gerlach (1988). In accordance with preferred embodiments, the ribozyme is engineered such that the cleavage recognition site is located near the 5' end of the B2M mRNA. In accordance with preferred other embodiments, the ribozyme is engineered such that the cleavage recognition site is located near the 5' end of the CIITA mRNA. This increases the efficiency and minimizes the intracellular accumulation of non-functional mRNA transcripts.

Like with antisense oligonucleotides, a ribozyme used in accordance with the invention may be composed of modified oligonucleotides to, e.g., improve stability. The ribozyme may be delivered to the cell by any means known in the art. The ribozyme may be delivered to the T-cell in form of an expression vector, such as a plasmid or viral vector, which, when transcribed in the cells, produces the ribozyme. According to preferred embodiments, a recombinant DNA vector is used in which a nucleotide sequence coding for the ribozyme is placed under the control of a promoter, such as a strong pol III or pol II promoter, so that a transfected cell will produce sufficient amounts of the ribozyme to destroy endogenous mRNA and inhibit translation. Because ribozymes, unlike antisense oligonucleotides, are catalytic, a lower intracellular concentration is required for efficiency.

In accordance with other particular embodiments, the inhibitory nucleic acid is an interfering RNA (RNAi) molecule. RNA interference is a biological process in which RNA molecules inhibit gene expression, typically causing the destruction of specific mRNA. Exemplary types of RNAi molecules include microRNA (miRNA), small interfering RNA (siRNA) and short hairpin RNA (shRNA). According to a preferred embodiment, the RNAi molecule is a miRNA. According to another preferred embodiment, the RNAi molecule is a siRNA. According to yet another preferred embodiment, the RNAi molecule is a shRNA. The production of RNAi molecules in vivo and in vitro and their methods of use are described in, e.g., U.S. Pat. No. 6,506,559, WO 01/36646, WO 00/44895, US2002/01621126, US2002/0086356, US2003/0108923, WO 02/44321, WO 02/055693, WO 02/055692 and WO 03/006477.

In accordance with a preferred embodiment, the RNAi molecule is an interfering RNA complementary to SEQ ID NO: 3. In accordance to another preferred embodiment, the RNAi molecule is a ribonucleic acid molecule comprising at least 10 consecutive nucleotides of the complement of SEQ ID NO: 3. In accordance with another preferred embodiment, the RNAi molecule is a double-stranded ribonucleic acid molecule comprising a first strand identical to 20 to 25, such as 21 to 23, consecutive nucleotides of SEQ ID NO: 3, and a second strand complementary to said first strand.

In accordance with a preferred embodiment, the RNAi molecule is an interfering RNA complementary to SEQ ID NO: 5. In accordance to another preferred embodiment, the RNAi molecule is a ribonucleic acid molecule comprising at least 10 consecutive nucleotides of the complement of SEQ ID NO: 5. In accordance with another preferred embodiment, the RNAi molecule is a double-stranded ribonucleic acid molecule comprising a first strand identical to 20 to 25, such as 21 to 23, consecutive nucleotides of SEQ ID NO: 5, and a second strand complementary to said first strand.

Engineering of the PD1/PDL1 Pathway of T-Cell Regulation

The present invention aims at facilitating the engraftment of T-cells, especially allogeneic T-cells, preferably by inhibiting the expression of B2M and/or CIITA in combination with inactivation of TCR.

As an alternative to or in combination with this approach, the inventors have found that T-cells can be disrupted for PD1 (Programmed cell death protein 1, also known as PD1; PD-1; CD279; SLEB2; hPD-1; hPD-1 or hSLE1), which is a 288 amino acid cell surface protein molecule encoded by the PDCD1 gene (NCBI—NC_000002.12). This protein is expressed on T cells and pro-B cells and has been found to negatively regulate T-cell responses (Carter L., et al., 2002). The formation of PD-1 receptor/PD-L1 ligand complex transmits an inhibitory signal, which reduces the proliferation of T-cells.

Programmed death ligand 1 (PD-L1) is a 40 kDa type 1 transmembrane protein that is deemed to play a major role in suppressing the immune system during particular events such as pregnancy, tissue allografts, autoimmune disease and other disease states such as hepatitis. PDL-1 (also called CD274 or B7H1) is encoded by CD274 gene (NCBI—NM_014143).

According to a particular aspect, the expression of both PD-1 and TCR are inhibited in the engineered T-cells of the invention, which has the dual effect of activating the T-cells as part of an allogeneic transplantation. However, the inactivation or inhibition of PD-1 can be also implemented as part of an autologous transplantation of T-cells, where the inhibition or disruption of TCR would not be required.

According to a further aspect of the invention, the inhibition or disruption of PD1 is combined with the over-expression of its ligand PDL-1 in the transplanted T-cells. This over-expression can be obtained, for instance, upon lentiviral or retroviral transformation in T-cells, in which PD-1 is inhibited or disrupted, or by any other means reported in the art. Accordingly, PDL1 that is over-expressed by the T-cells will not affect the [PD1⁻] transplanted cells, but only the [PD1⁺] T-cells from the patient. As a result, the T-cells from the patient are inhibited and do not activate against the transplanted cells, which facilitates their engraftment and persistence into the host.

According to a preferred embodiment, the invention provides engineered T-cells which are [PD1⁻][TCR⁻], while overexpressing PDL1 to facilitate their transplantation into a patient, in particular as part of an immunotherapy.

Expression of at Least One Non-Endogenous Immunosuppressive Polypeptide

According to some preferred embodiments, the inhibition of the expression of the beta-2m and/or the CIITA is carried out with an additional step of expression in said T-cell of at least one non-endogenous immunosuppressive polypeptide.

By "non-endogenous" polypeptide is meant a polypeptide not normally expressed by a donor's immune cell, preferably a polypeptide expressed by an exogenous polynucleotide that has been imported into the immune's cell genome. For instance, IL12 is not considered hereby as being a non-endogenous polypeptide because it is expressed from a preexisting gene from the donor's immune cell.

By "immunosuppressive" is meant that the expression of said non-endogenous polypeptide has the effect of alleviating the immune response of the patient host against the donor's immune cells.

The method of the present invention may thus comprise introducing into said T-cell an exogenous nucleic acid molecule comprising a nucleotide sequence coding for at least one non-endogenous immunosuppressive polypeptide, such as a viral MHC homolog or an NKG2D ligand.

Expression of Viral MHC Homolog

According to particularly preferred embodiments, said non-endogenous immunosuppressive polypeptide expressed in said T-cell is a viral MHC homolog, such as for instance UL18 (referred to as NP_044619 in the NCBI protein database).

According to these embodiments, the method of the present invention may thus comprise introducing into said T-cell an exogenous nucleic acid molecule comprising a nucleotide sequence coding for a viral MHC homolog, such as UL18. The exogenous nucleic acid molecule may comprise a nucleotide sequence coding for a polypeptide sharing at least 80%, preferably at least 90% and more preferably at least 95% of identity with SEQ ID NO: 89.

Figure 7:
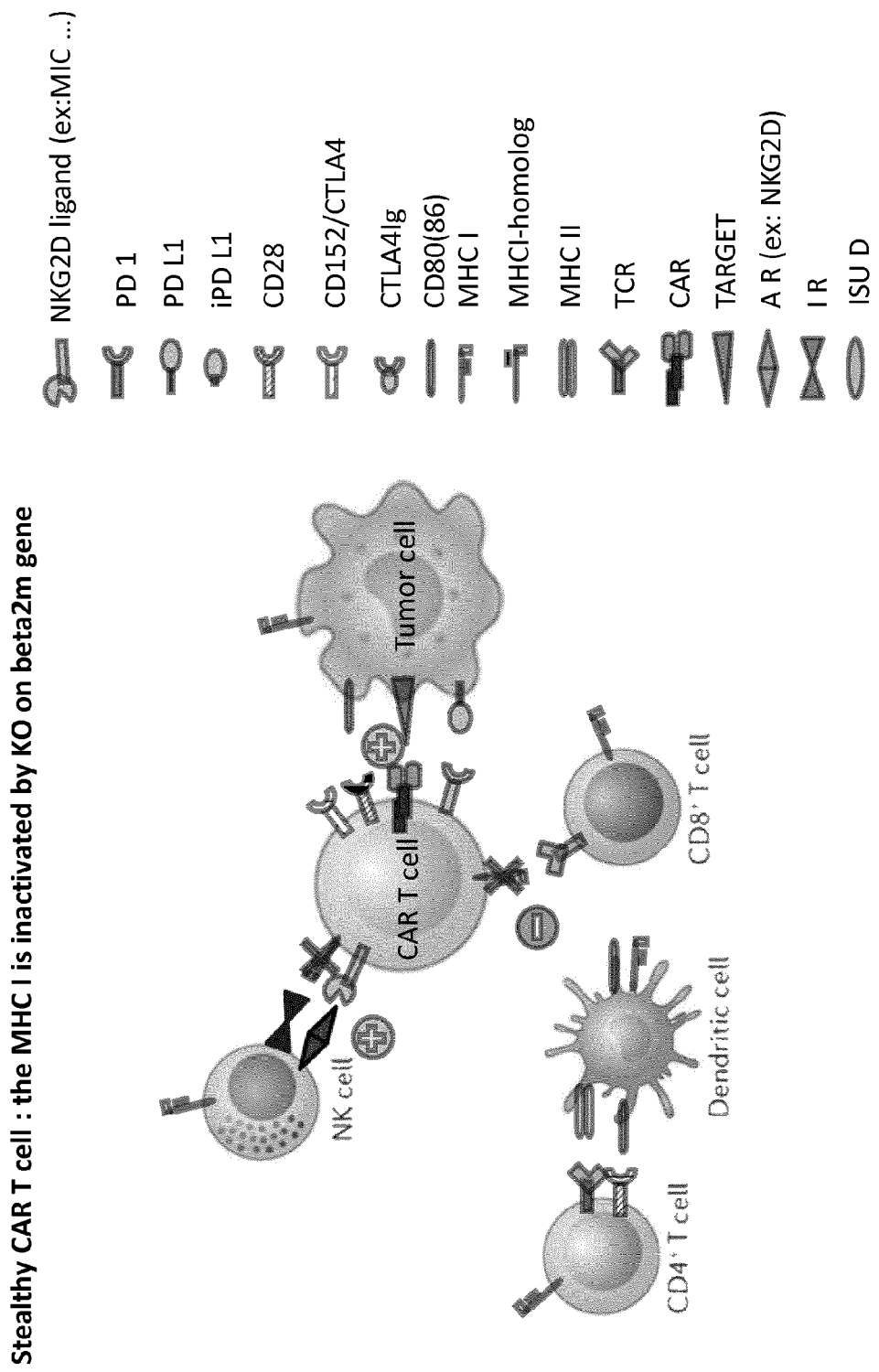
FIG. 7: Schematic representation of the potential interactions between an allogeneic CAR T cell with diverse host immune cells (CD8+ and CD4+ T cell, APC such as dendritic cell and NK cell), the CAR T cell having its B2M gene inactivated by KO. Sign (+) represents activation and sign (−) inhibition. The potential interaction between CAR T cell with the tumor cell remains unchanged. The inactivation of B2M gene which is one component of the MCHI, renders the latter non-functional in regards to the interactions with host cytotoxic T cell (CD8+) and with NK cell. Then, NK cell can exert its activation on allogeneic CAR T cell via activator pathway such NKG2D/NKG2D ligand.
Figure 8:
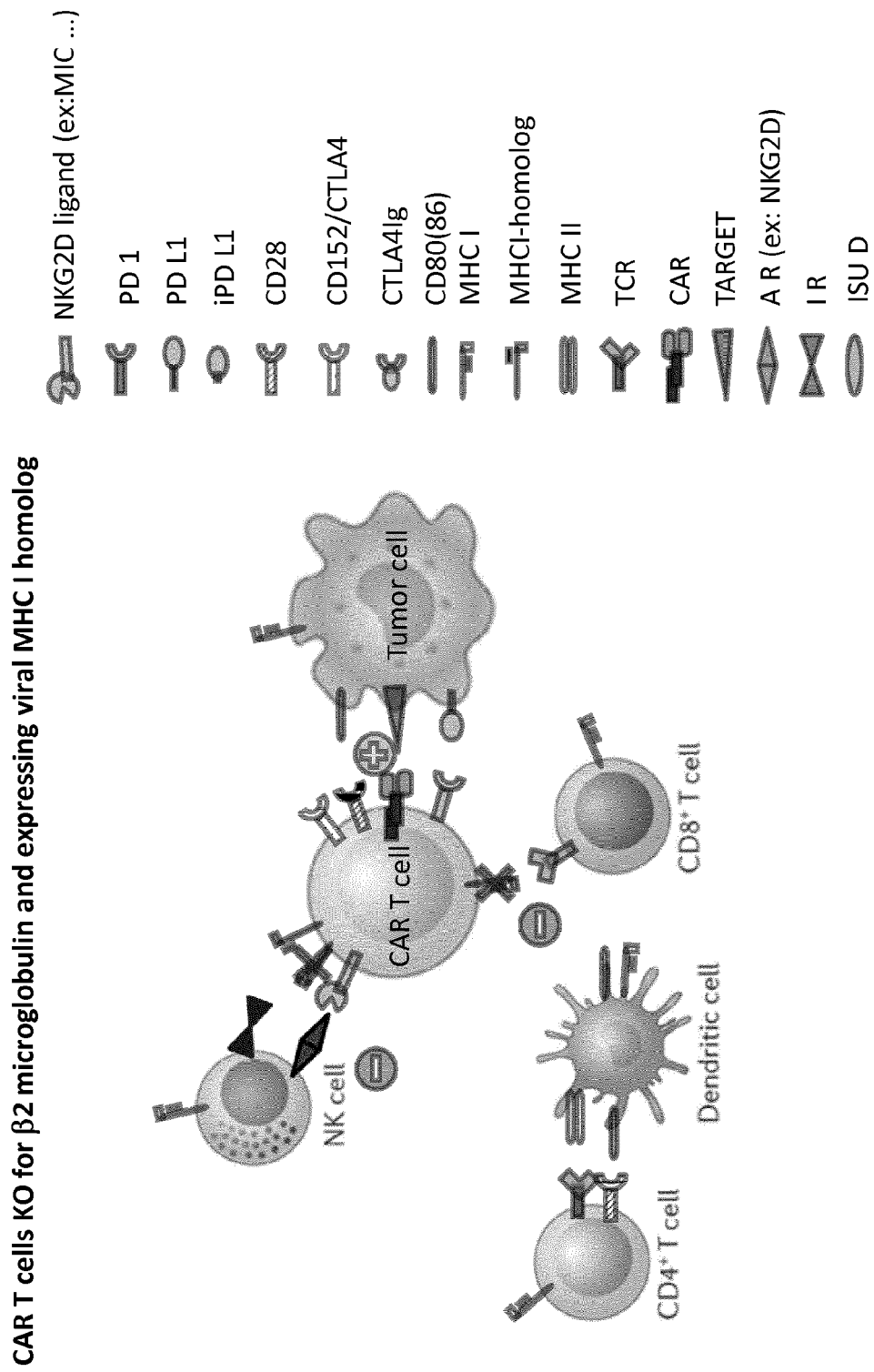
FIG. 8: Schematic representation of the potential interactions between an allogeneic CAR T cell with diverse host immune cells (CD8+ and CD4+ T cell, APC such as dendritic cell and NK cell), the CAR T cell having its B2M gene inactivated by KO and expressing viral MHCI homolog. Sign (+) represents activation and sign (−) inhibition. The potential interaction between CAR T cell with the tumor cell remains unchanged. As for the preceding figure (only B2M KO), the interaction between CART cell and host CD8+ T cell is alleviated. In this case, the expression of viral MHCI homolog renders the interaction with NK cell inoperative via MHCI/inhibitor receptor. The double genetic modification of allogeneic CAR T cells by KO of B2M combined with the expression of viral MHCI homolog strengthens their immunosuppressive protection.

The interaction between the allogeneic T cell and host immune cells is schematically represented in FIG. 8 (expression of viral MHC homolog) in regard to the situation to FIG. 7 (no expression). In both figures, the MHC class I is preferably inactivated by disrupting (KO) the beta2M gene.

Expression of NKG2D Hound

Some viruses such as cytomegaloviruses have acquired mechanisms to avoid NK cell mediate immune surveillance and interfere with the NKG2D pathway by secreting a protein able to bind NKG2D ligands and prevent their surface expression (Welte, S. A.; Sinzger, C.; Lutz, S. Z.; Singh-Jasuja, H.; Sampaio, K. L.; Eknigk, U.; Rammensee, H. G.; Steinle, A. 2003 "Selective intracellular retention of virally induced NKG2D ligands by the human cytomegalovirus UL16 glycoprotein". Eur. J. Immunol., 33, 194-203). In tumors cells, some mechanisms have evolved to evade NKG2D response by secreting NKG2D ligands such as ULBP2, MICB or MICA (Salih H R, Antropius H, Gieseke F, Lutz S Z, Kanz L, et al. (2003) Functional expression and release of ligands for the activating immunoreceptor NKG2D in leukemia. Blood 102: 1389-1396)

According to other particularly preferred embodiments, the non-endogenous immunosuppressive polypeptide to be expressed in said T-cell is an NKG2D ligand.

According to these embodiments, the method of the present invention may thus comprise introducing into said T-cell an exogenous nucleic acid molecule comprising a nucleotide sequence coding for an NKG2D ligand. The nucleic acid molecule may comprise a nucleotide sequence coding for a polypeptide sharing at least 80%, preferably at least 90% and more preferably at least 95% of identity with any one of SEQ ID NO: 90-97.

Figure 9:
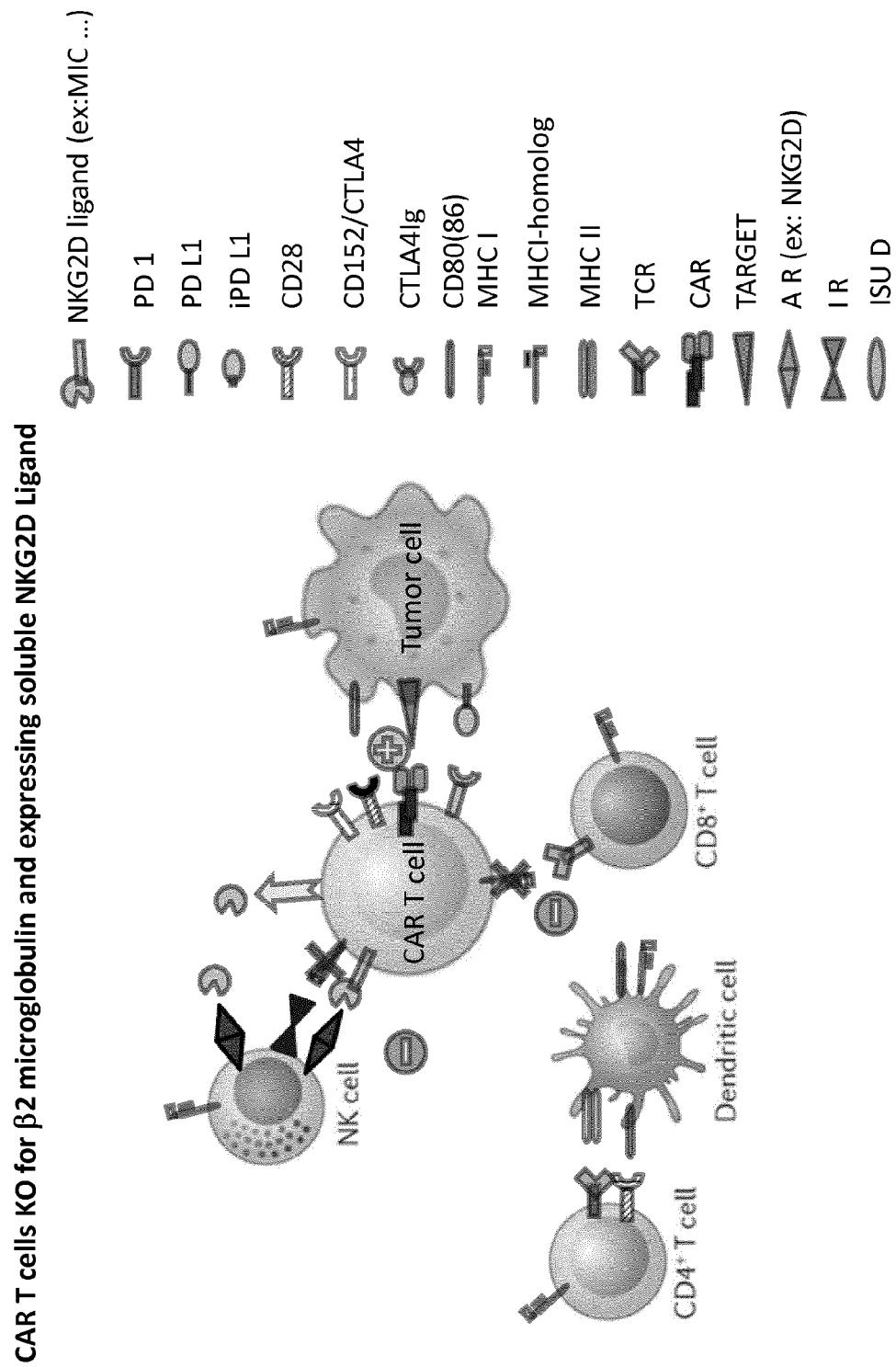
FIG. 9: Schematic representation of the potential interactions between an allogeneic CAR T cell with diverse host immune cells (CD8+ and CD4+ T cell, APC such as dendritic cell and NK cell), the CAR T cell having its B2M gene inactivated by KO and expressing a soluble NKG2D ligand. Sign (+) represents activation and sign (−) inhibition. The potential interaction between CAR T cell with the tumor cell remains unchanged. As for the preceding figure (only B2M KO), the interaction between CART cell and host CD8+ T cell is alleviated. The expression of soluble NKG2D ligand is another way to inactivation the interaction with NK cell. In this case, the soluble NKG2D ligand can bind to NKG2D receptor on NK cell but exerts no action, in contrast to the NKG2D ligand of CAR T cell with which it exerts an inhibitory competition. The double genetic modification of allogeneic CAR T cells by KO of B2M combined with the expression of soluble NKG2D ligand strengthens their immunosuppressive protection.

The interaction between the allogeneic T cell and host immune cells is schematically represented in FIG. 9 (expression of soluble NKG2D ligand) in regard to the situation to FIG. 7 (no expression). In both figures, the MHC class I is inactivated by disrupting (KO) the beta2M gene.

The Table 10 presented further in the text represents a viral MHC homolog (UL18) and a panel of NKG2D ligands and their polypeptide sequence to be expressed according to the present invention.

Chimeric Antigen Receptors (CARs)

Adoptive immunotherapy, which involves the transfer of autologous antigen-specific T-cells generated ex vivo, is a promising strategy to treat cancer or viral infections. The T-cells used for adoptive immunotherapy can be generated either by expansion of antigen-specific T cells or redirection of T cells through genetic engineering (Park, Rosenberg et al. 2011). Transfer of viral antigen specific T-cells is a well-established procedure used for the treatment of transplant associated viral infections and rare viral-related malignancies. Similarly, isolation and transfer of tumor specific T cells has been shown to be successful in treating melanoma.

Novel specificities in T-cells have been successfully generated through the genetic transfer of transgenic T-cell receptors or chimeric antigen receptors (CARs) (Jena, Dotti et al. 2010). CARs are synthetic receptors consisting of a targeting moiety that is associated with one or more signaling domains in a single fusion molecule. In general, the binding moiety of a CAR consists of an antigen-binding domain of a single-chain antibody (scFv), comprising the light and variable fragments of a monoclonal antibody joined by a flexible linker. Binding moieties based on receptor or ligand domains have also been used successfully. The signaling domains for first generation CARs are derived from the cytoplasmic region of the CD3zeta or the Fc receptor gamma chains. First generation CARs have been shown to successfully redirect T cell cytotoxicity, however, they failed to provide prolonged expansion and anti-tumor activity in vivo. Signaling domains from co-stimulatory molecules including CD28, OX-40 (CD134), and 4-1BB (CD137) have been added alone (second generation) or in combination (third generation) to enhance survival and increase proliferation of CAR modified T-cells. CARs have successfully allowed T-cells to be redirected against antigens expressed at the surface of tumor cells from various malignancies including lymphomas and solid tumors (Jena, Dotti et al. 2010).

CD19 is an attractive target for immunotherapy because the vast majority of B-acute lymphoblastic leukemia (B-ALL) uniformly express CD19, whereas expression is absent on non hematopoietic cells, as well as myeloid, erythroid, and T cells, and bone marrow stem cells. Clinical trials targeting CD19 on B-cell malignancies are underway with encouraging anti-tumor responses. Most infuse T cells genetically modified to express a chimeric antigen receptor (CAR) with specificity derived from the scFv region of a CD19-specific mouse monoclonal antibody FMC63 (WO2013/126712).

Therefore, in accordance with certain embodiments, the Chimeric Antigen Receptor expressed by the engineered T-cell is directed against the B-lymphocyte antigen CD19.

In accordance with certain embodiments, the Chimeric Antigen Receptor is a single chain Chimeric Antigen Receptor. As an example of single-chain Chimeric Antigen Receptor to be expressed in the engineered T-cells according to the present invention is a single polypeptide that comprises at least one extracellular ligand binding domain, a transmembrane domain and at least one signal transducing domain, wherein said extracellular ligand binding domain comprises a scFV derived from the specific anti-CD19 monoclonal antibody 4G7. Once transduced into the T-cell, for instance by using retroviral or lentiviral transduction, this CAR contributes to the recognition of CD19 antigen present at the surface of malignant B-cells involved in lymphoma or leukemia.

In accordance with particular embodiments, the Chimeric Antigen Receptor is a polypeptide comprising the amino acid sequence forth in SEQ ID NO: 6 or a variant thereof comprising an amino acid sequence that has at least 70%, such as at least 80%, at least 90%, at least 95%, or at least 99%, sequence identity with the amino acid sequence set forth in SEQ ID NO: 6 over the entire length of SEQ ID NO: 6. Preferably, the variant is capable of binding CD19.

A particularly preferred Chimeric Antigen Receptor is a polypeptide comprising the amino acid sequence set forth in SEQ ID NO: 7 or a variant thereof comprising an amino acid sequence that has at least 80%, such as at least 90%, at least 95%, or at least 99%, sequence identity with the amino acid sequence set forth in SEQ ID NO: 7 over the entire length of SEQ ID NO: 7. Such variant may differ from the polypeptide set forth in SEQ ID NO: 7 in the substitution of at least one, at least two or at least three amino acid residue(s). Preferably, said variant is capable of binding CD19.

In accordance with other certain embodiments, the Chimeric Antigen Receptor may be directed against another antigen expressed at the surface of a malignant or infected cell, such as a cluster of differentiation molecule, such as CD16, CD64, CD78, CD96, CLL1, CD116, CD117, CD71, CD45, CD71, CD123 and CD138, a tumor-associated surface antigen, such as ErbB2 (HER2/neu), carcinoembryonic antigen (CEA), epithelial cell adhesion molecule (EpCAM), epidermal growth factor receptor (EGFR), EGFR variant III (EGFRvIII), CD19, CD20, CD30, CD40, disialoganglioside GD2, ductal-epithelial mucine, gp36, TAG-72, glycosphingolipids, glioma-associated antigen, (3-human chorionic gonadotropin, alphafetoprotein (AFP), lectin-reactive AFP, thyroglobulin, RAGE-1, MN-CA IX, human telomerase reverse transcriptase, RU1, RU2 (AS), intestinal carboxyl esterase, mut hsp70-2, M-CSF, prostase, prostase specific antigen (PSA), PAP, NY-ESO-1, LAGA-la, p53, prostein, PSMA, surviving and telomerase, prostate-carcinoma tumor antigen-1 (PCTA-1), MAGE, ELF2M, neutrophil elastase, ephrin B2, CD22, insulin growth factor (IGF1)-I, IGF-II, IGFI receptor, mesothelin, a major histocompatibility complex (MHC) molecule presenting a tumor-specific peptide epitope, 5T4, ROR1, Nkp30, NKG2D, tumor stromal antigens, the extra domain A (EDA) and extra domain B (EDB) of fibronectin and the A1 domain of tenascin-C(TnC A1) and fibroblast associated protein (fap); a lineage-specific or tissue specific antigen such as CD3, CD4, CD8, CD24, CD25, CD33, CD34, CD133, CD138, CTLA-4, B7-1 (CD80), B7-2 (CD86), GM-CSF, cytokine receptors, endoglin, a major histocompatibility complex (MHC) molecule, BCMA (CD269, TNFRSF 17), multiple myeloma or lymphoblastic leukaemia antigen, such as one selected from TNFRSF17 (UNIPROT Q02223), SLAMF7 (UNIPROT Q9NQ25), GPRCSD (UNIPROT Q9NZD1), FKBP11 (UNIPROT Q9NYL4), KAMP3, ITGA8 (UNIPROT P53708), and FCRL5 (UNIPROT Q68SN8). a virus-specific surface antigen such as an HIV-specific antigen (such as HIV gp120); an EBV-specific antigen, a CMV-specific antigen, a HPV-specific antigen, a Lasse Virus-specific antigen, an Influenza Virus-specific antigen as well as any derivate or variant of these surface antigens.

In other certain embodiments, the Chimeric Antigen Receptor is a multi-chain Chimeric Antigen Receptor. Chimeric Antigen Receptors from the prior art introduced in T-cells have been formed of single chain polypeptides that necessitate serial appending of signaling domains. However, by moving signaling domains from their natural juxtamembrane position may interfere with their function. To overcome this drawback, the applicant recently designed a multi-chain CAR derived from FcɛRI to allow normal juxtamembrane position of all relevant signaling domains. In this new architecture, the high affinity IgE binding domain of FcɛRI alpha chain is replaced by an extracellular ligand-binding domain such as scFv to redirect T-cell specificity against cell targets and the N and/or C-termini tails of FcɛRI beta chain are used to place costimulatory signals in normal juxtamembrane positions as described in WO 2013/176916.

Accordingly, a CAR expressed by the engineered T-cell according to the invention can be a multi-chain chimeric antigen receptor particularly adapted to the production and expansion of engineered T-cells of the present invention. Such multi-chain CARs comprise at least two of the following components:
a) one polypeptide comprising the transmembrane domain of FcɛRI alpha chain and an extracellular ligand-binding domain,
b) one polypeptide comprising a part of N- and C-terminal cytoplasmic tail and the transmembrane domain of FcɛRI beta chain and/or
c) at least two polypeptides comprising each a part of intracytoplasmic tail and the transmembrane domain of FcɛRI gamma chain, whereby different polypeptides multimerize together spontaneously to form dimeric, trimeric or tetrameric CAR.

According to such architectures, ligands binding domains and signaling domains are born on separate polypeptides. The different polypeptides are anchored into the membrane in a close proximity allowing interactions with each other. In such architectures, the signaling and co-stimulatory domains can be in juxtamembrane positions (i.e. adjacent to the cell membrane on the internal side of it), which is deemed to allow improved function of co-stimulatory domains. The multi-subunit architecture also offers more flexibility and possibilities of designing CARs with more control on T-cell activation. For instance, it is possible to include several extracellular antigen recognition domains having different specificity to obtain a multi-specific CAR architecture. It is also possible to control the relative ratio between the different subunits into the multi-chain CAR. This type of architecture has been recently detailed by the applicant in PCT/US2013/058005.

The assembly of the different chains as part of a single multi-chain CAR is made possible, for instance, by using the different alpha, beta and gamma chains of the high affinity receptor for IgE (FcɛRI) (Metzger, Alcaraz et al. 1986) to which are fused the signaling and co-stimulatory domains. The gamma chain comprises a transmembrane region and cytoplasmic tail containing one immunoreceptor tyrosine-based activation motif (ITAM) (Cambier 1995).

The multi-chain CAR can comprise several extracellular ligand-binding domains, to simultaneously bind different elements in target thereby augmenting immune cell activation and function. In one embodiment, the extracellular ligand-binding domains can be placed in tandem on the same transmembrane polypeptide, and optionally can be separated by a linker. In another embodiment, said different extracellular ligand-binding domains can be placed on different transmembrane polypeptides composing the multi-chain CAR.

The signal transducing domain or intracellular signaling domain of the multi-chain CAR(s) of the invention is responsible for intracellular signaling following the binding of extracellular ligand binding domain to the target resulting in the activation of the immune cell and immune response. In other words, the signal transducing domain is responsible for the activation of at least one of the normal effector functions of the immune cell in which the multi-chain CAR is expressed. For example, the effector function of a T cell can be a cytolytic activity or helper activity including the secretion of cytokines.

In the present application, the term "signal transducing domain" refers to the portion of a protein which transduces the effector signal function signal and directs the cell to perform a specialized function.

Preferred examples of signal transducing domain for use in single or multi-chain CAR can be the cytoplasmic sequences of the Fc receptor or T cell receptor and co-receptors that act in concert to initiate signal transduction following antigen receptor engagement, as well as any derivate or variant of these sequences and any synthetic sequence that as the same functional capability. Signal transduction domain comprises two distinct classes of cytoplasmic signaling sequence, those that initiate antigen-dependent primary activation, and those that act in an antigen-independent manner to provide a secondary or co-stimulatory signal. Primary cytoplasmic signaling sequence can comprise signaling motifs which are known as immunoreceptor tyrosine-based activation motifs of ITAMs. ITAMs are well defined signaling motifs found in the intracytoplasmic tail of a variety of receptors that serve as binding sites for syk/zap70 class tyrosine kinases. Examples of ITAM used in the invention can include as non-limiting examples those derived from TCRzeta, FcRgamma, FcRbeta, FcRepsilon, CD3gamma, CD3delta, CD3epsilon, CD5, CD22, CD79a, CD79b and CD66d. According to particular embodiments, the signaling transducing domain of the multi-chain CAR can comprise the CD3zeta signaling domain, or the intracytoplasmic domain of the FcεRI beta or gamma chains.

According to particular embodiments, the signal transduction domain of multi-chain CARs of the present invention comprises a co-stimulatory signal molecule. A co-stimulatory molecule is a cell surface molecule other than an antigen receptor or their ligands that is required for an efficient immune response.

Ligand binding-domains can be any antigen receptor previously used, and referred to, with respect to single-chain CAR referred to in the literature, in particular scFv from monoclonal antibodies.

Engineered T-Cells

As a result of the present invention, engineered T-cells can be obtained having improved characteristics. In particular, the present invention provides an engineered, preferably isolated, T-cell which is characterized in that the expression of B2M and/or CIITA is inhibited.

According to certain embodiments, the present invention provides an engineered, preferably isolated, T-cell which expresses a rare-cutting endonuclease able to selectively inactivate by DNA cleavage, preferably double-strand break, the gene encoding B2M. According to particular embodiments, said T-cell comprises an exogenous nucleic acid molecule comprising a nucleotide sequence encoding said rare-cutting endonuclease. According to more particular embodiments, said rare-cutting endonuclease is a TAL-nuclease, meganuclease, zinc-finger nuclease (ZFN), or RNA guided endonuclease. Hence, in accordance with a specific embodiment, the rare-cutting endonuclease is a TAL-nuclease. In accordance with another specific embodiment, the rare-cutting endonuclease is a meganuclease. In accordance with another specific embodiment, the rare-cutting endonuclease is a zinc-finger nuclease. In accordance with yet another specific embodiment, the rare-cutting endonuclease is a RNA guided endonuclease, such as Cas9.

According to certain other embodiments, the present invention provides an engineered, preferably isolated, T-cell which comprises an exogenous nucleic acid molecule that inhibits the expression of B2M. According to particular embodiments, said T-cell comprises an exogenous nucleic acid molecule comprising a nucleotide sequence encoding a nucleic acid molecule that inhibits the expression of B2M. According to more particular embodiments, the nucleic acid molecule that inhibits the expression of B2M is an antisense oligonucleotide, ribozyme or interfering RNA (RNAi) molecule. Hence, in accordance with a specific embodiment, nucleic acid molecule that inhibits the expression of B2M is an antisense oligonucleotide. In accordance with another specific embodiment, nucleic acid molecule that inhibits the expression of B2M is a ribozyme, and preferably a hammerhead ribozyme. In accordance with another specific embodiment, nucleic acid molecule that inhibits the expression of B2M is an interfering RNA molecule.

According to certain embodiments, the present invention provides an engineered, preferably isolated, T-cell which expresses a rare-cutting endonuclease able to selectively inactivate by DNA cleavage, preferably double-strand break, the gene encoding CIITA. According to particular embodiments, said T-cell comprises an exogenous nucleic acid molecule comprising a nucleotide sequence encoding said rare-cutting endonuclease. According to more particular embodiments, said rare-cutting endonuclease is a TAL-nuclease, meganuclease, zinc-finger nuclease (ZFN), or RNA guided endonuclease. Hence, in accordance with a specific embodiment, the rare-cutting endonuclease is a TAL-nuclease. In accordance with another specific embodiment, the rare-cutting endonuclease is a meganuclease. In accordance with another specific embodiment, the rare-cutting endonuclease is a zinc-finger nuclease. In accordance with yet another specific embodiment, the rare-cutting endonuclease is a RNA or DNA guided endonuclease, such as Cas9 or Argonaute.

According to certain other embodiments, the present invention provides an engineered, preferably isolated, T-cell which comprises an exogenous nucleic acid molecule that inhibits the expression of CIITA. According to particular embodiments, said T-cell comprises an exogenous nucleic acid molecule comprising a nucleotide sequence encoding a nucleic acid molecule that inhibits the expression of CIITA. According to more particular embodiments, the nucleic acid molecule that inhibits the expression of CIITA is an antisense oligonucleotide, ribozyme or interfering RNA (RNAi) molecule. Hence, in accordance with a specific embodiment, nucleic acid molecule that inhibits the expression of CIITA is an antisense oligonucleotide. In accordance with another specific embodiment, nucleic acid molecule that inhibits the expression of CIITA is a ribozyme, and preferably a hammerhead ribozyme. In accordance with another specific embodiment, nucleic acid molecule that inhibits the expression of CIITA is an interfering RNA molecule.

According to certain embodiments, the engineered T-cell further expresses a rare-cutting endonuclease able to selectively inactivate by DNA cleavage, preferably double-strand break, at least one gene coding for a component of the T-cell receptor (TCR), such as TCR alpha. According to particular embodiments, said T-cell comprises an exogenous nucleic acid molecule comprising a nucleotide sequence encoding said rare-cutting endonuclease.

According to certain embodiments, the engineered T-cell further comprises expresses a Chimeric Antigen Receptor (CAR) directed against at least one antigen expressed at the surface of a malignant or infected cell. According to particular embodiments, said T-cell comprises an exogenous nucleic acid molecule comprising a nucleotide sequence encoding said CAR.

According to some embodiments, the present invention provides an engineered, preferably isolated, T-cell which expresses at least one non-endogenous immune-suppressive polypeptide. According to particular embodiments, said non-endogenous immune-suppressive polypeptide is a viral MHC homolog, such as UL18. The T-cell may thus comprise an exogenous nucleic acid molecule comprising a nucleotide sequence coding for a polypeptide sharing at least 80%, preferably at least 90% and more preferably at least 95% of identity with SEQ ID NO: 89. According to other particular embodiments, said non-endogenous immune-suppressive polypeptide is a NKG2D ligand. The T-cell may thus comprise an exogenous nucleic acid molecule comprising a nucleotide sequence coding for a polypeptide sharing at least 80%, preferably at least 90% and more preferably at least 95% of identity with any one of SEQ ID NO: 90-97.

It is understood that the details given herein in particularly with respect to the rare-cutting endonuclease able to selectively inactivate by DNA cleavage the gene encoding B2M, the nucleic acid molecule that inhibits the expression of B2M, the rare-cutting endonuclease able to selectively inactivate by DNA cleavage at least one gene coding for a component of the T-cell receptor (TCR), and the Chimeric Antigen Receptor also apply to this aspect of the invention.

Further, in the scope of the present invention is also encompassed a cell or cell line obtained from an engineered T-cell according to the invention, preferably displaying one of these phenotypes:

[b2m]⁻[TCR]⁻
[TCR]⁻[PD1]⁻[PDL-1]⁺
[b2m]⁻[TCR]⁻[PD1]⁻
[b2m]⁻[TCR]⁻[PD1]⁻[PDL-1]⁺
[b2m]⁻[viral MHC homolog]⁺
[b2m]⁻[TCR]⁻[viral MHC homolog]⁺
[b2m]⁻[NKG2D ligand]⁺
[b2m]⁻[TCR]⁻[NKG2D ligand]⁺

The T cells according to the present invention are preferably [CAR]⁺—i.e. armed with a chimeric antigen receptor to direct the specific recognition of tumor cells.

Delivery Methods

The inventors have considered any means known in the art to allow delivery inside cells or subcellular compartments of said cells the nucleic acid molecules employed in accordance with the invention. These means include viral transduction, electroporation and also liposomal delivery means, polymeric carriers, chemical carriers, lipoplexes, polyplexes, dendrimers, nanoparticles, emulsion, natural endocytosis or phagocytose pathway as non-limiting examples.

In accordance with the present invention, the nucleic acid molecules detailed herein may be introduced in the T-cell by any suitable methods known in the art. Suitable, non-limiting methods for introducing a nucleic acid molecule into a T-cell according include stable transformation methods, wherein the nucleic acid molecule is integrated into the genome of the cell, transient transformation methods wherein the nucleic acid molecule is not integrated into the genome of the cell and virus mediated methods. Said nucleic acid molecule may be introduced into a cell by, for example, a recombinant viral vector (e.g., retroviruses, adenoviruses), liposome and the like. Transient transformation methods include, for example, microinjection, electroporation or particle bombardment. In certain embodiments, the nucleic acid molecule is a vector, such as a viral vector or plasmid. Suitably, said vector is an expression vector enabling the expression of the respective polypeptide(s) or protein(s) detailed herein by the T-cell.

A nucleic acid molecule introduced into the T-cell may be DNA or RNA. In certain embodiments, a nucleic acid molecule introduced into the T-cell is DNA. In certain embodiments, a nucleic acid molecule introduced into the T-cell is RNA, and in particular an mRNA encoding a polypeptide or protein detailed herein, which mRNA is introduced directly into the T-cell, for example by electroporation. A suitable electroporation technique is described, for example, in International Publication WO2013/176915 (in particular the section titled "Electroporation" bridging pages 29 to 30). A particular nucleic acid molecule which may be an mRNA is the nucleic acid molecule comprising a nucleotide sequence coding for a rare-cutting endonuclease able to selectively inactivate by DNA cleavage the gene encoding B2M. Another particular nucleic acid molecule which may be an mRNA is the nucleic acid molecule comprising a nucleotide sequence coding for a rare-cutting endonuclease able to selectively inactivate by DNA cleavage the gene encoding CIITA. A yet other particular nucleic acid molecule which may be an mRNA is the nucleic acid molecule comprising a nucleotide sequence coding for a rare-cutting endonuclease able to selectively inactivate by DNA cleavage at least one gene coding for one component of the T-Cell Receptor (TCR).

As a preferred embodiment of the invention, nucleic acid molecules encoding the endonucleases of the present invention are transfected under mRNA form in order to obtain transient expression and avoid chromosomal integration of foreign DNA, for example by electroporation. The inventors have determined different optimal conditions for mRNA electroporation in T-cell displayed in Table 1. The inventor used the cytoPulse technology which allows, by the use of pulsed electric fields, to transiently permeabilize living cells for delivery of material into the cells (U.S. Pat. No. 6,010, 613 and WO 2004/083379). Pulse duration, intensity as well as the interval between pulses can be modified in order to reach the best conditions for high transfection efficiency with minimal mortality. Basically, the first high electric field pulses allow pore formation, while subsequent lower electric field pulses allow to moving the polynucleotide into the cell. In one aspect of the present invention, the inventor describe the steps that led to achievement of >95% transfection efficiency of mRNA in T cells, and the use of the electroporation protocol to transiently express different kind of proteins in T cells. In particular the invention relates to a method of transforming T cell comprising contacting said T cell with RNA and applying to T cell an agile pulse sequence consisting of:

(a) one electrical pulse with a voltage range from 2250 to 3000 V per centimeter, a pulse width of 0.1 ms and a pulse interval of 0.2 to 10 ms between the electrical pulses of step (a) and (b);

(b) one electrical pulse with a voltage range from 2250 to 3000 V with a pulse width of 100 ms and a pulse interval of 100 ms between the electrical pulse of step (b) and the first electrical pulse of step (c); and (c) 4 electrical pulses with a voltage of 325 V with a pulse width of 0.2 ms and a pulse interval of 2 ms between each of 4 electrical pulses.

In particular embodiment, the method of transforming T cell comprising contacting said T cell with RNA and applying to T cell an agile pulse sequence consisting of:

(a) one electrical pulse with a voltage of 2250, 2300, 2350, 2400, 2450, 2500, 2550, 2400, 2450, 2500, 2600, 2700, 2800, 2900 or 3000V per centimeter, a pulse width of 0.1 ms and a pulse interval of 0.2, 0.5, 1, 2, 3, 4, 5, 6, 7, 8, 9 or 10 ms between the electrical pulses of step (a) and (b);

(b) one electrical pulse with a voltage range from 2250, of 2250, 2300, 2350, 2400, 2450, 2500, 2550, 2400, 2450, 2500, 2600, 2700, 2800, 2900 or 3000V with a pulse width of 100 ms and a pulse interval of 100 ms between the electrical pulse of step (b) and the first electrical pulse of step (c); and (c) 4 electrical pulses with a voltage of 325 V with a pulse width of 0.2 ms and a pulse interval of 2 ms between each of 4 electrical pulses.

Any values included in the value range described above are disclosed in the present application. Electroporation medium can be any suitable medium known in the art. Preferably, the electroporation medium has conductivity in a range spanning 0.01 to 1.0 milliSiemens.

TABLE 1

Different cytopulse programs used to determine the minimal voltage required for electroporation in PBMC derived T-cells.

| Cytopulse program | Group 1 | | | | Group 2 | | | | Group 3 | | | |
|---|---|---|---|---|---|---|---|---|---|---|---|---|
| | Pulses | V | duration (ms) | Interval (ms) | Pulses | V | duration (ms) | Interval (ms) | Pulses | V | duration (ms) | Interval (ms) |
| 1 | 1 | 600 | 0.1 | 0.2 | 1 | 600 | 0.1 | 100 | 4 | 130 | 0.2 | 2 |
| 2 | 1 | 900 | 0.1 | 0.2 | 1 | 900 | 0.1 | 100 | 4 | 130 | 0.2 | 2 |
| 3 | 1 | 1200 | 0.1 | 0.2 | 1 | 1200 | 0.1 | 100 | 4 | 130 | 0.2 | 2 |
| 4 | 1 | 1200 | 0.1 | 10 | 1 | 900 | 0.1 | 100 | 4 | 130 | 0.2 | 2 |
| 5 | 1 | 900 | 0.1 | 20 | 1 | 600 | 0.1 | 100 | 4 | 130 | 0.2 | 2 |

Non Alloreactive T-Cells:

Although the method of the invention could be carried out in-vivo as part of a gene therapy, for instance, by using viral vectors targeting T-cells in blood circulation, which would include genetic sequences expressing a specific rare-cutting endonuclease along with other genetic sequences expressing, e.g., a CAR, the method of the invention is more generally intended to be practiced ex-vivo on cultured T-cells obtainable from patients or donors. The engineered T-cells engineered ex-vivo can be either re-implanted into a patient from where they originate, as part of an autologous treatment, or to be used as part of an allogeneic treatment. In this later case, it is preferable to further engineer the cells to make them non-alloreactive to ensure their proper engraftment. Accordingly, the method of the invention may include additional steps of procuring the T-cells from a donor and to inactivate genes thereof involved in MHC recognition and or being targets of immunosuppressive drugs such as described for instance in WO 2013/176915.

T-cell receptors (TCR) are cell surface receptors that participate in the activation of T-cells in response to the presentation of antigen. The TCR is generally made from two chains, alpha and beta, which assemble to form a heterodimer and associates with the CD3-transducing subunits to form the T-cell receptor complex present on the cell surface. Each alpha and beta chain of the TCR consists of an immunoglobulin-like N-terminal variable (V) and constant (C) region, a hydrophobic transmembrane domain, and a short cytoplasmic region. As for immunoglobulin molecules, the variable region of the alpha and beta chains are generated by V(D)J recombination, creating a large diversity of antigen specificities within the population of T cells. However, in contrast to immunoglobulins that recognize intact antigen, T cells are activated by processed peptide fragments in association with an MHC molecule, introducing an extra dimension to antigen recognition by T cells, known as MHC restriction. Recognition of MHC disparities between the donor and recipient through the T cell receptor leads to T cell proliferation and the potential development of GVHD. It has been shown that normal surface expression of the TCR depends on the coordinated synthesis and assembly of all seven components of the complex (Ashwell and Klusner 1990). The inactivation of TCR alpha or TCR beta can result in the elimination of the TCR from the surface of T cells preventing recognition of alloantigen and thus GVHD.

Thus, still according to the invention, engraftment of the T-cells may be improved by inactivating at least one gene encoding a TCR component. TCR is rendered not functional in the cells by inactivating TCR alpha gene and/or TCR beta gene(s).

With respect to the use of Cas9/CRISPR system, the inventors have determined appropriate target sequences within the 3 exons encoding TCR, allowing a significant reduction of toxicity in living cells, while retaining cleavage efficiency. The preferred target sequences are noted in Table 2 (+ for lower ratio of TCR negative cells, ++ for intermediate ratio, +++ for higher ratio).

TABLE 2 appropriate target sequences for the guide RNA using Cas9 in T-cells

| Exon TCR | Position | Strand | Target genomic sequence | SEQ ID | efficiency |
|---|---|---|---|---|---|
| Ex1 | 78 | −1 | GAGAATCAAAATCGGTGAATAGG | 8 | +++ |
| Ex3 | 26 | 1 | TTCAAAACCTGTCAGTGATTGGG | 9 | +++ |
| Ex1 | 153 | 1 | TGTGCTAGACATGAGGTCTATGG | 10 | +++ |
| Ex3 | 74 | −1 | CGTCATGAGCAGATTAAACCCGG | 11 | +++ |
| Ex1 | 4 | −1 | TCAGGGTTCTGGATATCTGTGGG | 12 | +++ |
| Ex1 | 5 | −1 | GTCAGGGTTCTGGATATCTGTGG | 13 | +++ |
| Ex3 | 33 | −1 | TTCGGAACCCAATCACTGACAGG | 14 | +++ |
| Ex3 | 60 | −1 | TAAACCCGGCCACTTTCAGGAGG | 15 | +++ |
| Ex1 | 200 | −1 | AAAGTCAGATTTGTTGCTCCAGG | 16 | ++ |
| Ex1 | 102 | 1 | AACAAATGTGTCACAAAGTAAGG | 17 | ++ |

TABLE 2-continued appropriate target sequences for the guide RNA using Cas9 in T-cells

| Exon TCR | Position | Strand | Target genomic sequence | SEQ ID | efficiency |
|---|---|---|---|---|---|
| Ex1 | 39 | -1 | TGGATTTAGAGTCTCTCAGCTGG | 18 | ++ |
| Ex1 | 59 | -1 | TAGGCAGACAGACTTGTCACTGG | 19 | ++ |
| Ex1 | 22 | -1 | AGCTGGTACACGGCAGGGTCAGG | 20 | ++ |
| Ex1 | 21 | -1 | GCTGGTACACGGCAGGGTCAGGG | 21 | ++ |
| Ex1 | 28 | -1 | TCTCTCAGCTGGTACACGGCAGG | 22 | ++ |
| Ex3 | 25 | 1 | TTTCAAAACCTGTCAGTGATTGG | 23 | ++ |
| Ex3 | 63 | -1 | GATTAAACCCGGCCACTTTCAGG | 24 | ++ |
| Ex2 | 17 | -1 | CTCGACCAGCTTGACATCACAGG | 25 | ++ |
| Ex1 | 32 | -1 | AGAGTCTCTCAGCTGGTACACGG | 26 | ++ |
| Ex1 | 27 | -1 | CTCTCAGCTGGTACACGGCAGGG | 27 | ++ |
| Ex2 | 12 | 1 | AAGTTCCTGTGATGTCAAGCTGG | 28 | ++ |
| Ex3 | 55 | 1 | ATCCTCCTCCTGAAAGTGGCCGG | 29 | ++ |
| Ex3 | 86 | 1 | TGCTCATGACGCTGCGGCTGTGG | 30 | ++ |
| Ex1 | 146 | 1 | ACAAAACTGTGCTAGACATGAGG | 31 | + |
| Ex1 | 86 | -1 | ATTTGTTTGAGAATCAAAATCGG | 32 | + |
| Ex2 | 3 | -1 | CATCACAGGAACTTTCTAAAAGG | 33 | + |
| Ex2 | 34 | 1 | GTCGAGAAAAGCTTTGAAACAGG | 34 | + |
| Ex3 | 51 | -1 | CCACTTTCAGGAGGAGGATTCGG | 35 | + |
| Ex3 | 18 | -1 | CTGACAGGTTTTGAAAGTTTAGG | 36 | + |
| Ex2 | 43 | 1 | AGCTTTGAAACAGGTAAGACAGG | 37 | + |
| Ex1 | 236 | -1 | TGGAATAATGCTGTTGTTGAAGG | 38 | + |
| Ex1 | 182 | 1 | AGAGCAACAGTGCTGTGGCCTGG | 39 | + |
| Ex3 | 103 | 1 | CTGTGGTCCAGCTGAGGTGAGGG | 40 | + |
| Ex3 | 97 | 1 | CTGCGGCTGTGGTCCAGCTGAGG | 41 | + |
| Ex3 | 104 | 1 | TGTGGTCCAGCTGAGGTGAGGGG | 42 | + |
| Ex1 | 267 | 1 | CTTCTTCCCCAGCCCAGGTAAGG | 43 | + |
| Ex1 | 15 | -1 | ACACGGCAGGGTCAGGGTTCTGG | 44 | + |
| Ex1 | 177 | 1 | CTTCAAGAGCAACAGTGCTGTGG | 45 | + |
| Ex1 | 256 | -1 | CTGGGGAAGAAGGTGTCTTCTGG | 46 | + |
| Ex3 | 56 | 1 | TCCTCCTCCTGAAAGTGGCCGGG | 47 | + |
| Ex3 | 80 | 1 | TTAATCTGCTCATGACGCTGCGG | 48 | + |
| Ex3 | 57 | -1 | ACCCGGCCACTTTCAGGAGGAGG | 49 | + |
| Ex1 | 268 | 1 | TTCTTCCCCAGCCCAGGTAAGGG | 50 | + |
| Ex1 | 266 | -1 | CTTACCTGGGCTGGGGAAGAAGG | 51 | + |
| Ex1 | 262 | 1 | GACACCTTCTTCCCCAGCCCAGG | 52 | + |
| Ex3 | 102 | 1 | GCTGTGGTCCAGCTGAGGTGAGG | 53 | + |
| Ex3 | 51 | 1 | CCGAATCCTCCTCCTGAAAGTGG | 54 | + |

MHC antigens are also proteins that played a major role in transplantation reactions. Rejection is mediated by T cells reacting to the histocompatibility antigens on the surface of implanted tissues, and the largest group of these antigens is the major histocompatibility antigens (MHC). These proteins are expressed on the surface of all higher vertebrates and are called HLA antigens (for human leukocyte antigens) in human cells. Like TCR, the MHC proteins serve a vital role in T cell stimulation. Antigen presenting cells (often dendritic cells) display peptides that are the degradation products of foreign proteins on the cell surface on the MHC. In the presence of a co-stimulatory signal, the T cell becomes activated, and will act on a target cell that also displays that same peptide/MHC complex. For example, a stimulated T helper cell will target a macrophage displaying an antigen in conjunction with its MHC, or a cytotoxic T cell (CTL) will act on a virally infected cell displaying foreign viral peptides.

Thus, in order to provide less alloreactive T-cells, the method of the invention can further comprise the step of inactivating or mutating one HLA gene.

The class I HLA gene cluster in humans comprises three major loci, B, C and A, as well as several minor loci. The class II HLA cluster also comprises three major loci, DP, DQ and DR, and both the class I and class II gene clusters are polymorphic, in that there are several different alleles of both the class I and II genes within the population. There are also several accessory proteins that play a role in HLA functioning as well. The TapI and Tap2 subunits are parts of the TAP transporter complex that is essential in loading peptide antigens on to the class I HLA complexes, and the LMP2 and LMP7 proteosome subunits play roles in the proteolytic degradation of antigens into peptides for display on the HLA. Reduction in LMP7 has been shown to reduce the amount of MHC class I at the cell surface, perhaps through a lack of stabilization (Fehling et al. (1999) Science 265:1234-1237). In addition to TAP and LMP, there is the tapasin gene, whose product forms a bridge between the TAP complex and the HLA class I chains and enhances peptide loading. Reduction in tapasin results in cells with impaired MHC class I assembly, reduced cell surface expression of the MHC class I and impaired immune responses (Grandea et al. (2000) Immunity 13:213-222 and Garbi et al. (2000) Nat. Immunol. 1:234-238). Any of the above genes may be inactivated as part of the present invention as disclosed, for instance in WO 2012/012667.

Hence, in accordance with certain embodiments, the method of the invention further comprises inactivating at least one gene selected from the group consisting of RFXANK, RFX5, RFXAP, TAP1, TAP2, ZXDA, ZXDB and ZXDC. Inactivation may, for instance, be achieved by using a genome modification, more particularly through the expression in the T-cell of a rare-cutting endonuclease able to selectively inactivate by DNA cleavage a gene selected from the group consisting of RFXANK, RFX5, RFXAP, TAP1, TAP2, ZXDA, ZXDB and ZXDC.

Activation and Expansion of T Cells

The method according to the invention may include a further step of activating and/or expanding the T-cell(s). This can be done prior to or after genetic modification of the T-cell(s), using the methods as described, for example, in U.S. Pat. Nos. 6,352,694; 6,534,055; 6,905,680; 6,692,964; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005. According to these methods, the T cells of the invention can be expanded by contact with a surface having attached thereto an agent that stimulates a CD3 TCR complex associated signal and a ligand that stimulates a co-stimulatory molecule on the surface of the T cells.

In particular, T cell populations may be stimulated in vitro such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either CD4+ T cells or CD8+ T cells, an anti-CD3 antibody and an anti-CD28 antibody. For example, the agents providing each signal may be in solution or coupled to a surface. As those of ordinary skill in the art can readily appreciate, the ratio of particles to cells may depend on particle size relative to the target cell. In further embodiments of the present invention, the cells, such as T cells, are combined with agent-coated beads, the beads and the cells are subsequently separated, and then the cells are cultured. In an alternative embodiment, prior to culture, the agent-coated beads and cells are not separated but are cultured together. Cell surface proteins may be ligated by allowing paramagnetic beads to which anti-CD3 and anti-CD28 are attached (3×28 beads) to contact the T cells. In one embodiment the cells (for example, 4 to 10 T cells) and beads (for example, DYNABEADS® M-450 CD3/CD28 T paramagnetic beads at a ratio of 1:1) are combined in a buffer, preferably PBS (without divalent cations such as, calcium and magnesium). Again, those of ordinary skill in the art can readily appreciate any cell concentration may be used. The mixture may be cultured for several hours (about 3 hours) to about 14 days or any hourly integer value in between. In another embodiment, the mixture may be cultured for 21 days. Conditions appropriate for T cell culture include an appropriate media (e.g., Minimal Essential Media or RPMI Media 1640 or, X-vivo 5, (Lonza)) that may contain factors necessary for proliferation and viability, including serum (e.g., fetal bovine or human serum), interleukin-2 (IL-2), insulin, IFN-g, 1L-4, 1L-7, GM-CSF, -10, -2, 1L-TGFp, and TNF– or any other additives for the growth of cells known to the skilled artisan. Other additives for the growth of cells include, but are not limited to, surfactant, plasmanate, and reducing agents such as N-acetyl-cysteine and 2-mercaptoethanoi. Media can include RPMI 1640, A1M-V, DMEM, MEM, a-MEM, F-12, X-Vivo 1, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% CO2). T cells that have been exposed to varied stimulation times may exhibit different characteristics In another particular embodiment, said cells can be expanded by co-culturing with tissue or cells. Said cells can also be expanded in vivo, for example in the subject's blood after administrating said cell into the subject.

Therapeutic Applications

The T-cells obtainable in accordance with the present invention are intended to be used as a medicament, and in particular for treating, among others, cancer, infections (such viral infections) or immune diseases in a patient in need thereof. Accordingly, the present invention provides engineered T-cells for use as a medicament. Particularly, the present invention provides engineered T-cells for use in the treatment of a cancer, such as lymphoma, or viral infection. Also provided are compositions, particularly pharmaceutical compositions, which comprise at least one engineered T-cell of the present invention. In certain embodiments, a composition may comprise a population of engineered T-cell of the present invention.

The treatment can be ameliorating, curative or prophylactic. It may be either part of an autologous immunotherapy or part of an allogenic immunotherapy treatment. By autologous, it is meant that cells, cell line or population of cells used for treating patients are originating from said patient or from a Human Leucocyte Antigen (HLA) compatible donor. By allogeneic is meant that the cells or population of cells used for treating patients are not originating from said patient but from a donor.

The invention is particularly suited for allogenic immunotherapy, insofar as it enables the transformation of T-cells, typically obtained from donors, into non-alloreactive cells. This may be done under standard protocols and reproduced as many times as needed. The resulted modified T-cells may be pooled and administrated to one or several patients, being made available as an "off the shelf" therapeutic product.

The treatments are primarily to treat patients diagnosed with cancer. Cancers are preferably leukemias and lymphomas, which have liquid tumors, but may also concern solid tumors. Types of cancers to be treated with the genetically engineered T-cells of the invention include, but are not limited to, carcinoma, blastoma, and sarcoma, and certain leukemia or lymphoid malignancies, benign and malignant tumors, and malignancies e.g., sarcomas, carcinomas, and melanomas. Adult tumors/cancers and pediatric tumors/cancers are also included.

The treatment can take place in combination with one or more therapies selected from the group of antibodies therapy, chemotherapy, cytokines therapy, dendritic cell therapy, gene therapy, hormone therapy, laser light therapy and radiation therapy.

According to certain embodiments, T-cells of the invention can undergo robust in vivo T-cell expansion upon administration to a patient, and can persist in the body fluids for an extended amount of time, preferably for a week, more preferably for 2 weeks, even more preferably for at least one month. Although the T-cells according to the invention are expected to persist during these periods, their life span into the patient's body are intended not to exceed a year, preferably 6 months, more preferably 2 months, and even more preferably one month.

The administration of the cells or population of cells according to the present invention may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous or intralymphatic injection, or intraperitoneally. In one embodiment, the cell compositions of the present invention are preferably administered by intravenous injection.

The administration of the cells or population of cells can consist of the administration of 104-109 cells per kg body weight, preferably 105 to 106 cells/kg body weight including all integer values of cell numbers within those ranges. The cells or population of cells can be administrated in one or more doses. In another embodiment, said effective amount of cells are administrated as a single dose. In another embodiment, said effective amount of cells are administrated as more than one dose over a period time. Timing of administration is within the judgment of managing physician and depends on the clinical condition of the patient. The cells or population of cells may be obtained from any source, such as a blood bank or a donor. While individual needs vary, determination of optimal ranges of effective amounts of a given cell type for a particular disease or conditions within the skill of the art. An effective amount means an amount which provides a therapeutic or prophylactic benefit. The dosage administrated will be dependent upon the age, health and weight of the recipient, kind of concurrent treatment, if any, frequency of treatment and the nature of the effect desired.

In other embodiments, said effective amount of cells or composition comprising those cells are administrated parenterally. Said administration can be an intravenous administration. Said administration can be directly done by injection within a tumor.

In certain embodiments, cells are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or nataliziimab treatment for MS patients or efaliztimab treatment for psoriasis patients or other treatments for PML patients. In further embodiments, the T cells of the invention may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludaribine, cyclosporin, FK506, rapamycin, mycoplienolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin) (Liu et al., Cell 66:807-815, 11; Henderson et al., Immun. 73:316-321, 1991; Bierer et al., Citrr. Opin. mm n. 5:763-773, 93). In a further embodiment, the cell compositions of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH, In another embodiment, the cell compositions of the present invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded genetically engineered T-cells of the present invention. In an additional embodiment, expanded cells are administered before or following surgery.

Also encompassed within this aspect of the invention are methods for treating a patient in need thereof, comprising a) providing at least one engineered T-cell of the present invention, preferably a population of said T-cell; and b) administering said T-cell or population to said patient.

Also encompassed within this aspect of the invention are methods for preparing a medicament using at least one engineered T-cell of the present invention, and preferably a population of said T-cell. Accordingly, the present invention provides the use of at least one engineered T-cell of the present invention, and preferably a population of said T-cell, in the manufacture of a medicament. Preferably, such medicament is for use in the treatment of a cancer, such as lymphoma, or viral infection.

Other Definitions

Amino acid residues in a polypeptide sequence are designated herein according to the one-letter code, in which, for example, Q means Gln or Glutamine residue, R means Arg or Arginine residue and D means Asp or Aspartic acid residue.

Amino acid substitution means the replacement of one amino acid residue with another, for instance the replacement of an Arginine residue with a Glutamine residue in a peptide sequence is an amino acid substitution.

Nucleotides are designated as follows: one-letter code is used for designating the base of a nucleoside: a is adenine, t is thymine, c is cytosine, and g is guanine. For the degenerated nucleotides, r represents g or a (purine nucleotides), k represents g or t, s represents g or c, w represents a or t, m represents a or c, y represents t or c (pyrimidine nucleotides), d represents g, a or t, v represents g, a or c, b represents g, t or c, h represents a, t or c, and n represents g, a, t or c.

"As used herein, "nucleic acid" or "polynucleotides" refers to nucleotides and/or polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Nucleic acids can be either single stranded or double stranded.

by "polynucleotide successively comprising a first region of homology to sequences upstream of said double-stranded break, a sequence to be inserted in the genome of said cell and a second region of homology to sequences downstream of said double-stranded break" it is intended to mean a DNA construct or a matrix comprising a first and second portion that are homologous to regions 5' and 3' of a DNA target in situ. The DNA construct also comprises a third portion positioned between the first and second portion which comprise some homology with the corresponding DNA sequence in situ or alternatively comprise no homology with the regions 5' and 3' of the DNA target in situ. Following cleavage of the DNA target, a homologous recombination event is stimulated between the genome containing the targeted gene comprised in the locus of interest and this matrix, wherein the genomic sequence containing the DNA target is replaced by the third portion of the matrix and a variable part of the first and second portions of said matrix.

by "DNA target", "DNA target sequence", "target DNA sequence", "nucleic acid target sequence", "target sequence", or "processing site" is intended a polynucleotide sequence that can be targeted and processed by a rare-cutting endonuclease according to the present invention. These terms refer to a specific DNA location, preferably a genomic location in a cell, but also a portion of genetic material that can exist independently to the main body of genetic material such as plasmids, episomes, virus, transposons or in organelles such as mitochondria as non-limiting example. As non-limiting examples of RNA guided target sequences, are those genome sequences that can hybridize the guide RNA which directs the RNA guided endonuclease to a desired locus.

By "delivery vector" or "delivery vectors" is intended any delivery vector which can be used in the present invention to put into cell contact (i.e "contacting") or deliver inside cells or subcellular compartments (i.e "introducing") agents/chemicals and molecules (proteins or nucleic acids) needed in the present invention. It includes, but is not limited to liposomal delivery vectors, viral delivery vectors, drug delivery vectors, chemical carriers, polymeric carriers, lipoplexes, polyplexes, dendrimers, microbubbles (ultrasound contrast agents), nanoparticles, emulsions or other appropriate transfer vectors. These delivery vectors allow delivery of molecules, chemicals, macromolecules (genes, proteins), or other vectors such as plasmids, or penetrating peptides. In these later cases, delivery vectors are molecule carriers.

The terms "vector" or "vectors" refer to a nucleic acid molecule capable of transporting another nucleic acid to which it has been linked. A "vector" in the present invention includes, but is not limited to, a viral vector, a plasmid, a RNA vector or a linear or circular DNA or RNA molecule which may consists of a chromosomal, non-chromosomal, semi-synthetic or synthetic nucleic acids. Preferred vectors are those capable of autonomous replication (episomal vector) and/or expression of nucleic acids to which they are linked (expression vectors). Large numbers of suitable vectors are known to those of skill in the art and commercially available.

Viral vectors include retrovirus, adenovirus, parvovirus (e.g. adenoassociated viruses), coronavirus, negative strand RNA viruses such as orthomyxovirus (e.g., influenza virus), rhabdovirus (e.g., rabies and vesicular stomatitis virus), paramyxovirus (e.g. measles and Sendai), positive strand RNA viruses such as picornavirus and alphavirus, and double-stranded DNA viruses including adenovirus, herpesvirus (e.g., Herpes Simplex virus types 1 and 2, Epstein-Barr virus, cytomegalovirus), and poxvirus (e.g., vaccinia, fowlpox and canarypox). Other viruses include Norwalk virus, togavirus, flavivirus, reoviruses, papovavirus, hepadnavirus, and hepatitis virus, for example. Examples of retroviruses include: avian leukosis-sarcoma, mammalian C-type, B-type viruses, D type viruses, HTLV-BLV group, lentivirus, spumavirus (Coffin, J. M., Retroviridae: The viruses and their replication, In Fundamental Virology, Third Edition, B. N. Fields, et al., Eds., Lippincott-Raven Publishers, Philadelphia, 1996).

By "lentiviral vector" is meant HIV-Based lentiviral vectors that are very promising for gene delivery because of their relatively large packaging capacity, reduced immunogenicity and their ability to stably transduce with high efficiency a large range of different cell types. Lentiviral vectors are usually generated following transient transfection of three (packaging, envelope and transfer) or more plasmids into producer cells. Like HIV, lentiviral vectors enter the target cell through the interaction of viral surface glycoproteins with receptors on the cell surface. On entry, the viral RNA undergoes reverse transcription, which is mediated by the viral reverse transcriptase complex. The product of reverse transcription is a double-stranded linear viral DNA, which is the substrate for viral integration in the DNA of infected cells. By "integrative lentiviral vectors (or LV)", is meant such vectors as non limiting example, that are able to integrate the genome of a target cell. At the opposite by "non integrative lentiviral vectors (or NILV)" is meant efficient gene delivery vectors that do not integrate the genome of a target cell through the action of the virus integrase.

Delivery vectors and vectors can be associated or combined with any cellular permeabilization techniques such as sonoporation or electroporation or derivatives of these techniques.

By "cell" or "cells" is intended any eukaryotic living cells, primary cells and cell lines derived from these organisms for in vitro cultures.

By "primary cell" or "primary cells" are intended cells taken directly from living tissue (i.e. biopsy material) and established for growth in vitro, that have undergone very few population doublings and are therefore more representative of the main functional components and characteristics of tissues from which they are derived from, in comparison to continuous tumorigenic or artificially immortalized cell lines.

As non-limiting examples cell lines can be selected from the group consisting of CHO-K1 cells; HEK293 cells; Caco2 cells; U2-OS cells; NIH 3T3 cells; NSO cells; SP2 cells; CHO-S cells; DG44 cells; K-562 cells, U-937 cells; MRCS cells; IMR90 cells; Jurkat cells; HepG2 cells; HeLa cells; HT-1080 cells; HCT-116 cells; Hu-h7 cells; Huvec cells; Molt 4 cells.

All these cell lines can be modified by the method of the present invention to provide cell line models to produce, express, quantify, detect, study a gene or a protein of interest; these models can also be used to screen biologically active molecules of interest in research and production and various fields such as chemical, biofuels, therapeutics and agronomy as non-limiting examples.

by "mutation" is intended the substitution, deletion, insertion of up to one, two, three, four, five, six, seven, eight, nine, ten, eleven, twelve, thirteen, fourteen, fifteen, twenty, twenty five, thirty, forty, fifty, or more nucleotides/amino acids in a polynucleotide (cDNA, gene) or a polypeptide sequence. The mutation can affect the coding sequence of a gene or its regulatory sequence. It may also affect the structure of the genomic sequence or the structure/stability of the encoded mRNA.

by "variant(s)", it is intended a repeat variant, a variant, a DNA binding variant, a TALE-nuclease variant, a polypeptide variant obtained by mutation or replacement of at least one residue in the amino acid sequence of the parent molecule.

by "functional variant" is intended a catalytically active mutant of a protein or a protein domain; such mutant may have the same activity compared to its parent protein or protein domain or additional properties, or higher or lower activity.

By "gene" is meant the basic unit of heredity, consisting of a segment of DNA arranged in a linear manner along a chromosome, which codes for a specific protein or segment of protein. A gene typically includes a promoter, a 5' untranslated region, one or more coding sequences (exons), optionally introns, a 3' untranslated region. The gene may further comprise a terminator, enhancers and/or silencers.

As used herein, the term "locus" is the specific physical location of a DNA sequence (e.g. of a gene) on a chromosome. The term "locus" can refer to the specific physical location of a rare-cutting endonuclease target sequence on a chromosome. Such a locus can comprise a target sequence that is recognized and/or cleaved by a rare-cutting endonuclease according to the invention. It is understood that the locus of interest of the present invention can not only qualify a nucleic acid sequence that exists in the main body of genetic material (i.e. in a chromosome) of a cell but also a portion of genetic material that can exist independently to said main body of genetic material such as plasmids, episomes, virus, transposons or in organelles such as mitochondria as non-limiting examples.

The term "cleavage" refers to the breakage of the covalent backbone of a polynucleotide. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. Double stranded DNA, RNA, or DNA/RNA hybrid cleavage can result in the production of either blunt ends or staggered ends.

By "fusion protein" is intended the result of a well-known process in the art consisting in the joining of two or more genes which originally encode for separate proteins or part of them, the translation of said "fusion gene" resulting in a single polypeptide with functional properties derived from each of the original proteins.

"identity" refers to sequence identity between two nucleic acid molecules or polypeptides. Identity can be determined by comparing a position in each sequence which may be aligned for purposes of comparison. When a position in the compared sequence is occupied by the same base or amino acid, then the molecules are identical at that position. A degree of similarity or identity between nucleic acid or amino acid sequences is a function of the number of identical or matching nucleotides or amino acids at positions shared by the nucleic acid or amino acid sequences, respectively. Various alignment algorithms and/or programs may be used to calculate the identity between two sequences, including FASTA, or BLAST which are available as a part of the GCG sequence analysis package (University of Wisconsin, Madison, Wis.), and can be used with, e.g., default setting. For example, polypeptides having at least 70%, 85%, 90%, 95%, 98% or 99% identity to specific polypeptides described herein and preferably exhibiting substantially the same functions, as well as polynucleotide encoding such polypeptides, are contemplated.

"inhibiting" or "inhibit" expression of B2M means that the expression of B2M in the cell is reduced by at least 1%, at least 5%, at least 10%, at least 20%, at least 30%, at least 40%, at least 50% at least 60%, at least 70%, at least 80%, at least 90%, at least 95%, at least 99% or 100%. More particularly, "inhibiting" or "inhibit" expression of B2M means that the amount of B2M in the cell is reduced by at least 1%, at least 5%, at least 10%, at least 20%, at least 30%, at least 40%, at least 50% at least 60%, at least 70%, at least 80%, at least 90%, at least 95%, at least 99% or 100%. The expression or amount of protein in a cell can be determined by any suitable means know in the art, such as ELISA, Immunohistochemistry, Western Blotting or Flow Cytometry using B2M specific antibodies. Such antibodies are commercially available from various sources, such from Merck Millipore, Billerica, MA, USA; or Abcam plc, Cambridge, UK.

"inhibiting" or "inhibit" expression of CIITA means that the expression of CIITA in the cell is reduced by at least 1%, at least 5%, at least 10%, at least 20%, at least 30%, at least 40%, at least 50% at least 60%, at least 70%, at least 80%, at least 90%, at least 95%, at least 99% or 100%. More particularly, "inhibiting" or "inhibit" expression of CIITA means that the amount of CIITA in the cell is reduced by at least 1%, at least 5%, at least 10%, at least 20%, at least 30%, at least 40%, at least 50% at least 60%, at least 70%, at least 80%, at least 90%, at least 95%, at least 99% or 100%. The expression or amount of protein in a cell can be determined by any suitable means know in the art, such as ELISA, Immunohistochemistry, Western Blotting or Flow Cytometry using CIITA specific antibodies. Such antibodies are commercially available from various sources, such from Abcam plc, Cambridge, UK; or Santa Cruz Biotechnology, Inc., Santa Cruz, CA, USA.

"signal-transducing domain" or "co-stimulatory ligand" refers to a molecule on an antigen presenting cell that specifically binds a cognate co-stimulatory molecule on a T-cell, thereby providing a signal which, in addition to the primary signal provided by, for instance, binding of a TCR/CD3 complex with an MHC molecule loaded with peptide, mediates a T cell response, including, but not limited to, proliferation activation, differentiation and the like. A co-stimulatory ligand can include but is not limited to CD7, B7-1 (CD80), B7-2 (CD86), PD-L1, PD-L2, 4-1BBL, OX40L, inducible costimulatory igand (ICOS-L), intercellular adhesion molecule (ICAM, CD30L, CD40, CD70, CD83, HLA-G, MICA, M1CB, HVEM, lymphotoxin beta receptor, 3/TR6, ILT3, ILT4, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as but not limited to, CD27, CD28, 4-IBB, OX40, CD30, CD40, PD-1, ICOS, lymphocyte function-associated antigen-1 (LFA-1), CD2, CD7, LTGHT, NKG2C, B7-H3, a ligand that specifically binds with CD83.

A "co-stimulatory molecule" refers to the cognate binding partner on a Tcell that specifically binds with a co-stimulatory ligand, thereby mediating a co-stimulatory response by the cell, such as, but not limited to proliferation. Co-stimulatory molecules include, but are not limited to an MHC class I molecule, BTLA and Toll ligand receptor.

A "co-stimulatory signal" as used herein refers to a signal, which in combination with primary signal, such as TCR/CD3 ligation, leads to T cell proliferation and/or upregulation or downregulation of key molecules.

"bispecific antibody" refers to an antibody that has binding sites for two different antigens within a single antibody molecule. It will be appreciated by those skilled in the art that other molecules in addition to the canonical antibody structure may be constructed with two binding specificities. It will further be appreciated that antigen binding by bispecific antibodies may be simultaneous or sequential. Bispecific antibodies can be produced by chemical techniques (see e.g., Kranz et al. (1981) Proc. Natl. Acad. Sci. USA 78, 5807), by "polydoma" techniques (See U.S. Pat. No. 4,474,893) or by recombinant DNA techniques, which all are known per se. As a non-limiting example, each binding domain comprises at least one variable region from an antibody heavy chain ("VH or H region"), wherein the VH region of the first binding domain specifically binds to the lymphocyte marker such as CD3, and the VH region of the second binding domain specifically binds to tumor antigen.

The term "extracellular ligand-binding domain" as used herein is defined as an oligo- or polypeptide that is capable of binding a ligand. Preferably, the domain will be capable of interacting with a cell surface molecule. For example, the extracellular ligand-binding domain may be chosen to recognize a ligand that acts as a cell surface marker on target cells associated with a particular disease state. Thus examples of cell surface markers that may act as ligands include those associated with viral, bacterial and parasitic infections, autoimmune disease and cancer cells.

The term "subject" or "patient" as used herein includes all members of the animal kingdom including non-human primates and humans.

The above written description of the invention provides a manner and process of making and using it such that any person skilled in this art is enabled to make and use the same, this enablement being provided in particular for the subject matter of the appended claims, which make up a part of the original description.

Where a numerical limit or range is stated herein, the endpoints are included. Also, all values and subranges within a numerical limit or range are specifically included as if explicitly written out.

Having generally described this invention, a further understanding can be obtained by reference to certain specific examples, which are provided herein for purposes of illustration only, and are not intended to be limiting unless otherwise specified.

EXAMPLES

TALE-Nucleases Cleaving Human CIITA mRNA encoding the TALE-nucleases targeting exons of the human CIITA gene were ordered from Cellectis Bioresearch (8, rue de la Croix Jarry, 75013 PARIS). Table 3 below indicates the target sequences cleaved by each of the two independent entities (called half TALE-nucleases) each containing a repeat sequence engineered to bind and cleave between target sequences consisting of two 17-bp long sequences (called half targets) separated by a 15-bp spacer. Because Exon 2 and 3 are shared by all transcript variants of CIITA, two TALEN pairs were designed for Exon 2 and 3. No obvious offsite targeting in the human genome have been predicted using TALE-Nucleases targeting these sequences.

TABLE 3

Description of the CIITA TALE-nucleases and related target sequences

| Target name | Target sequence |
|---|---|
| TALEN 1_Exon 2_CMH-II-TA | TTCCCTCCCAGGCAGCTC acagtgtgccaccaTGGA GTTGGGGCCCCTA (SEQ ID NO: 55) |
| TALEN 2_Exon 2_CMH-II-TA | TGCCTCTACCACTTCTAT gaccagatggacctGGCT GGAGAAGAAGAGA (SEQ ID NO: 56) |
| TALEN 1_Exon3_CMH-II-TA | 5'TCTTCATCCAAGGGAC TTttcctcccagaaccCG ACACAGACACCATCA (SEQ ID NO: 57) |
| TALEN 2_Exon3_CMH-II-TA | TGTTGTGTGACATGGAAG gtgatgaagagaccAGGG AGGCTTATGCCAA (SEQ ID NO: 58) |

TALE-Nucleases Cleaving Human β2m mRNA encoding the TALE-nucleases targeting exons of the human β2m gene were ordered from Cellectis Bioresearch (8, rue de la Croix Jarry, 75013 PARIS). Table 4 below indicates the target sequences cleaved by each of the two independent entities (called half TALE-nucleases) each containing a repeat sequence engineered to bind and cleave between target sequences consisting of two 17-bp long sequences (called half targets) separated by a 15-bp spacer.

TABLE 4

Description of the β2m TALE-nucleases and related target sequences

| Target name | Target sequence | Half TALE-nuclease sequence |
|---|---|---|
| B2M_T03 | 5'-CCAAAGATTCAGGTTT actcacgtcatccagc (spacer) AGAGAATGGAAAGTC-3' (SEQ ID NO: 59) | Repeat B2M_T03-L (pCLS24605) SEQ ID NO: 67 B2M_T03-R (pCLS24606) SEQ ID NO: 68 |

TALE-Nucleases Cleaving Human TCR Genes (TRAC and TRBC)

The human genome contains two functional T-cell receptor beta chains (TRBC1 and TRBC2). During the development of alpha/beta T lymphocytes, one of these two constant chains is selected in each cell to be spliced to the variable region of TCR-beta and form a functional full length beta chain. Table 5 below presents a TRAC and 2 TRBC target sequences and their corresponding TALEN sequences. The 2 TRBC targets were chosen in sequences conserved between TRBC1 and TRBC2 so that the corresponding TALE-nuclease would cleave both TRBC1 and TRBC2 at the same time.

TABLE 5

Description of the TRAC and TRBC TALE-nucleases and sequences of the TALE-nucleases target sites in the human corresponding genes.

| Target | Target sequence | Half TALE-nuclease |
|---|---|---|
| TRAC_T01 | TTGTCCCACAGATATCC Agaaccctgaccctg CCGTGTACCAGCTGAGA (SEQ ID NO: 60) | TRAC_T01-L TALEN (SEQ ID NO: 69) TRAC_T01-R TALEN (SEQ ID NO: 70) |
| TRBC_T01 | TGTGTTTGAGCCATCAG aagcagagatctccc ACACCCAAAAGGCCACA (SEQ ID NO: 61) | TRBC_T01-L TALEN (SEQ ID NO: 71) TRBC_T01-R TALEN (SEQ ID NO: 72) |
| TRBC_T02 | TTCCCACCCGAGGTCGC tgtgtttgagccatca GAAGCAGAGATCTCCCA (SEQ ID NO: 62) | TRBC_T02-L TALEN (SEQ ID NO: 73) TRBC_T02-R TALEN (SEQ ID NO: 74) |

Other target sequences in TRAC and CD52 genes have been designed, which are displayed in Table 6.

TABLE 6

Additional target sequences for TRAC TALE-nucleases.

| Target | Target sequence |
|---|---|
| TRAC_T02 | TTTAGAAAGTTCCTGTG atgtcaagctggtcg AGAAAAGCTTTGAAACA (SEQ ID NO: 63) |
| TRAC_T03 | TCCAGTGACAAGTCTGT ctgcctattcaccga TTTTGATTCTCAAACAA (SEQ ID NO: 64) |
| TRAC_T04 | TATATCACAGACAAAAC tgtgctagacatgag GTCTATGGACTTCAAGA (SEQ ID NO: 65) |
| TRAC_T05 | TGAGGTCTATGGACTTC aagagcaacagtgct GTGGCCTGGAGCAACAA (SEQ ID NO: 66) |

Electroporation of mRNA of Purified Tcells Activated Using Cytopulse Technology

After determining the best cytopulse program that allows an efficient DNA electroporation of T cells, we tested whether this method was applicable to the mRNA electroporation.

5×106 purified T cells preactivated 6 days with PHA/IL2 were resuspended in cytoporation buffer T (BTX-Harvard apparatus) and electroporated in 0.4 cm cuvettes with 10 μg of mRNA encoding GFP or 20 μg of plasmids encoding GFP or pUC using the preferred cytopulse program of table 7.

TABLE 7

Cytopulse program used to electroporate purified T-cells.

| Cytopulse program | Group 1 | | | | Group 2 | | | | Group 3 | | | |
|---|---|---|---|---|---|---|---|---|---|---|---|---|
| | Pulse | V | duration (ms) | Interval (ms) | Pulse | V | duration (ms) | Interval (ms) | Pulse | V | duration (ms) | Interval (ms) |
| 3 | 1 | 1200 | 0.1 | 0.2 | 1 | 1200 | 0.1 | 100 | 4 | 130 | 0.2 | 2 |

48 h after transfection cells were stained with viability dye (eFluor-450) and the cellular viability and % of viable GFP+ cells was determined by flow cytometry.

The electroporation of RNA with the optimal condition determined here was not toxic and allowed transfection of more than 95% of the viable cells.

In synthesis, the whole dataset shows that T-cells can be efficiently transfected either with DNA or RNA. In particular, RNA transfection has no impact on cellular viability and allows uniform expression levels of the transfected gene of interest in the cellular population.

Efficient transfection can be achieved early after cellular activation, independently of the activation method used (PHA/IL-2 or CD3/CD28-coated-beads). The inventors have succeeded in transfecting cells from 72 h after activation with efficiencies of >95%. In addition, efficient transfection of T cells after thawing and activation can also be obtained using the same electroporation protocol.

mRNA Electroporation in Primary Human T Cells for TALE-Nuclease Functional Expression After demonstrating that mRNA electroporation allow efficient expression of GFP in primary human T cells, we tested whether this method was applicable to the expression of other proteins of interest. Transcription activator-like effector nucleases (TALE-nuclease) are site-specific nucleases generated by the fusion of a TAL DNA binding domain to a DNA cleavage domain. They are powerful genome editing tools as they induce double-strand breaks at practically any desired DNA sequence. These double-strand breaks activate Non-homologous end-joining (NHEJ), an error-prone DNA repair mechanism, potentially leading to inactivation of any desired gene of interest. Alternatively, if an adequate repair template is introduced into the cells at the same time, TALE-nuclease-induced DNA breaks can be repaired by homologous recombination, therefore offering the possibility of modifying at will the gene sequence.

We have used mRNA electroporation to express a TALE-nuclease designed to specifically cleave a sequence in the human gene coding for the alpha chain of the T cell antigen receptor (TRAC). Mutations induced in this sequence are expected to result in gene inactivation and loss of TCRαβ complex from the cell surface. TRAC TALE-nuclease RNA or non-coding RNA as control are transfected into activated primary human T lymphocytes using Cytopulse technology. The electroporation sequence consisted in 2 pulses of 1200 V followed by four pulses of 130 V as described in Table 7.

Figure 4:
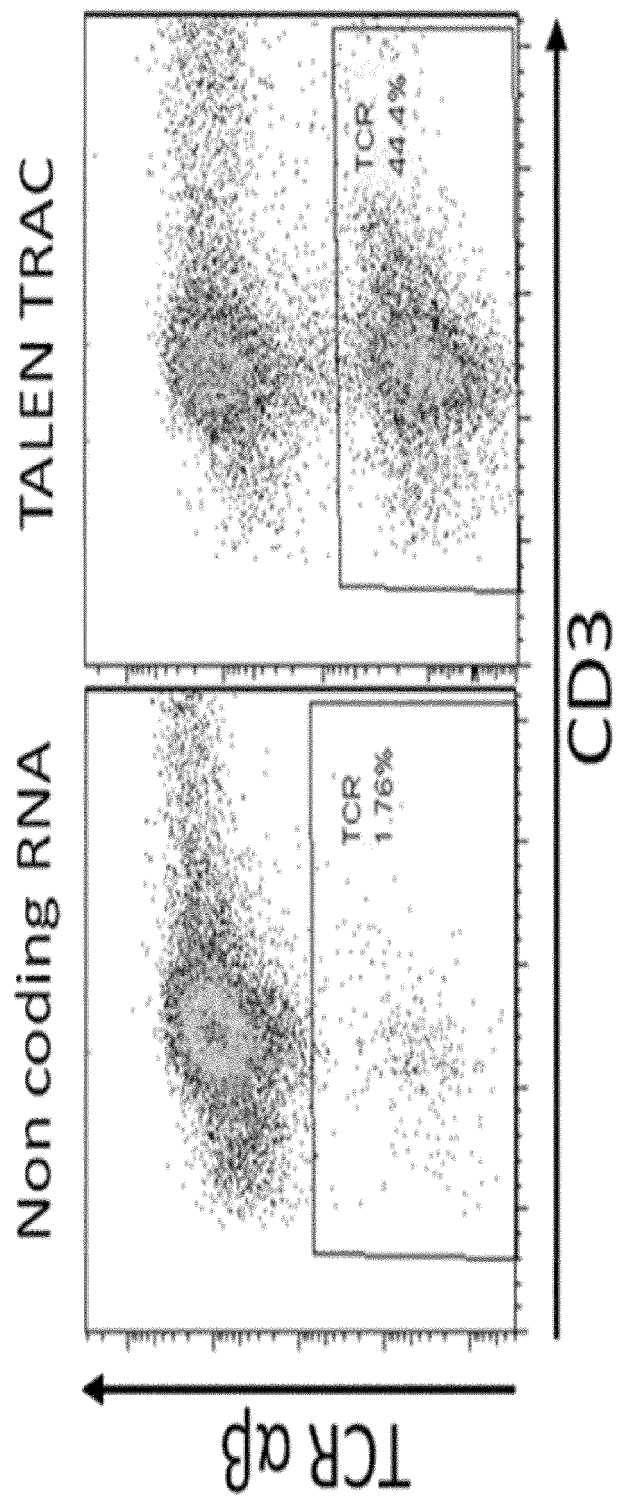
FIG. 4: Flow cytometry analysis of TCR alpha/beta and CD3 expression on human primary T cells following TRAC TALE-nuclease mRNA electroporation (top).

By flow cytometry analysis of TCR surface expression 7 days post electroporation (FIG. 4, top panel), we observed that 44% of T cells lost the expression of TCRαβ. We analyzed the genomic DNA of the transfected cells by PCR amplification of the TRAC locus followed by 454 high throughput sequencing. 33% of alleles sequenced (727 out of 2153) contained insertion or deletion at the site of TALE-nuclease cleavage.

These data indicate that electroporation of mRNA using cytopulse technology results in functional expression of TRAC TALE-nuclease.

Activity of TRAC-TALE-Nuclease and TRBC-TALE-Nuclease in HEK293 Cells

Each TALE-nuclease construct was subcloned using restriction enzyme digestion in a mammalian expression vector under the control of pEF1alpha long promoter. One million HEK293 cells were seeded one day prior to transfection. Cells were transfected with 2.5 µg of each of the two plasmids encoding the TALE-nucleases recognizing the two half targets in the genomic sequence of interest in the T-cell receptor alpha constant chain region (TRAC) or T-cell receptor beta constant chain region (TRBC) under the control of the EF1-alpha promoter or 5 µg of a control pUC vector (pCLS0003) using 25 µl of lipofectamine (Invitrogen) according to the manufacturer's instructions. The double stranded cleavage generated by TALE-nucleases in TRAC coding sequences is repaired in live cells by non homologous end joining (NHEJ), which is an error-prone mechanism. Activity of TALE-nucleases in live cells is measured by the frequency of insertions or deletions at the genomic locus targeted. 48 hours after transfection, genomic DNA was isolated from transfected cells and locus specific PCRs were performed using the following primers: for TRAC: 5'-ATCACTGGCATCTGGACTCCA-3' (SEQ ID NO: for TRBC1: 5'-AGAGCCCCTACCAGAACCAGAC-3' (SEQ ID NO: 76, or for TRBC2: 5'-GGACCTAGTAACATAAT-TGTGC-3' (SEQ ID NO: 77), and the reverse primer for TRAC: 5'-CCTCATGTCTAGCACAGTTT-3'(SEQ ID NO: 78), for TRBC1 and TRBC2: 5'-ACCAGCTCAGCTC-CACGTGGT-3' (SEQ ID NO: 79). PCR products were sequenced by a 454 sequencing system (454 Life Sciences). Approximately 10,000 sequences were obtained per PCR product and then analyzed for the presence of site-specific insertion or deletion events; results are in Table 8.

TABLE 8

Percentages of indels for TALE-nuclease targeting TRAC_T01, TRBC_T01 and TRBC_T02 targets.

| Target | % Indels with TALE-nuclease transfection | % Indels with pUC control transfection |
|---|---|---|
| TRAC_T01 | 41.9 | 0.3 |
| TRBC_T01 in constant chain 1 | 3.81 | 0 |
| TRBC_T01 in constant chain 2 | 2.59 | 0 |
| TRBC_T02 in constant chain 1 | 14.7 | 0 |
| TRBC_T02 in constant chain 1 | 5.99 | 0 |

Activity of β2m and TRAC-TALE-Nuclease in Primary T Lymphocytes

Each TALE-nuclease construct was subcloned using restriction enzyme digestion in a mammalian expression vector under the control of the T7 promoter.

mRNA encoding TALE-nuclease cleaving β2m, TRAC and TRBC genomic sequence were synthesized from plasmid carrying the coding sequences downstream from the T7 promoter. T lymphocytes isolated from peripheral blood were activated for 5 days using anti-CD3/CD28 activator beads (Life technologies) and 5 million cells were then transfected by electroporation with 10 μg of each of 2 mRNAs encoding both half TALE-nuclease (or non coding RNA as controls) using a CytoLVT-P instrument. As a consequence of the insertions and deletions induced by NHEJ, the coding sequence for β2m and/or TRAC will be out of frame in a fraction of the cells resulting in non-functional genes. 5 days after electroporation, cells were labeled with fluorochrome-conjugated anti-β2m or anti-TCR antibody by flow cytometry for the presence of β2m or TCR at their cell surface. Since all T lymphocytes expanded from peripheral blood normally express β2m and TCR, the proportion of β2m-negative or TCR-negative cells is a direct measure of TALE-nuclease activity.

Functional Analysis of T Cells with Targeted TRAC Gene

Figure 3:
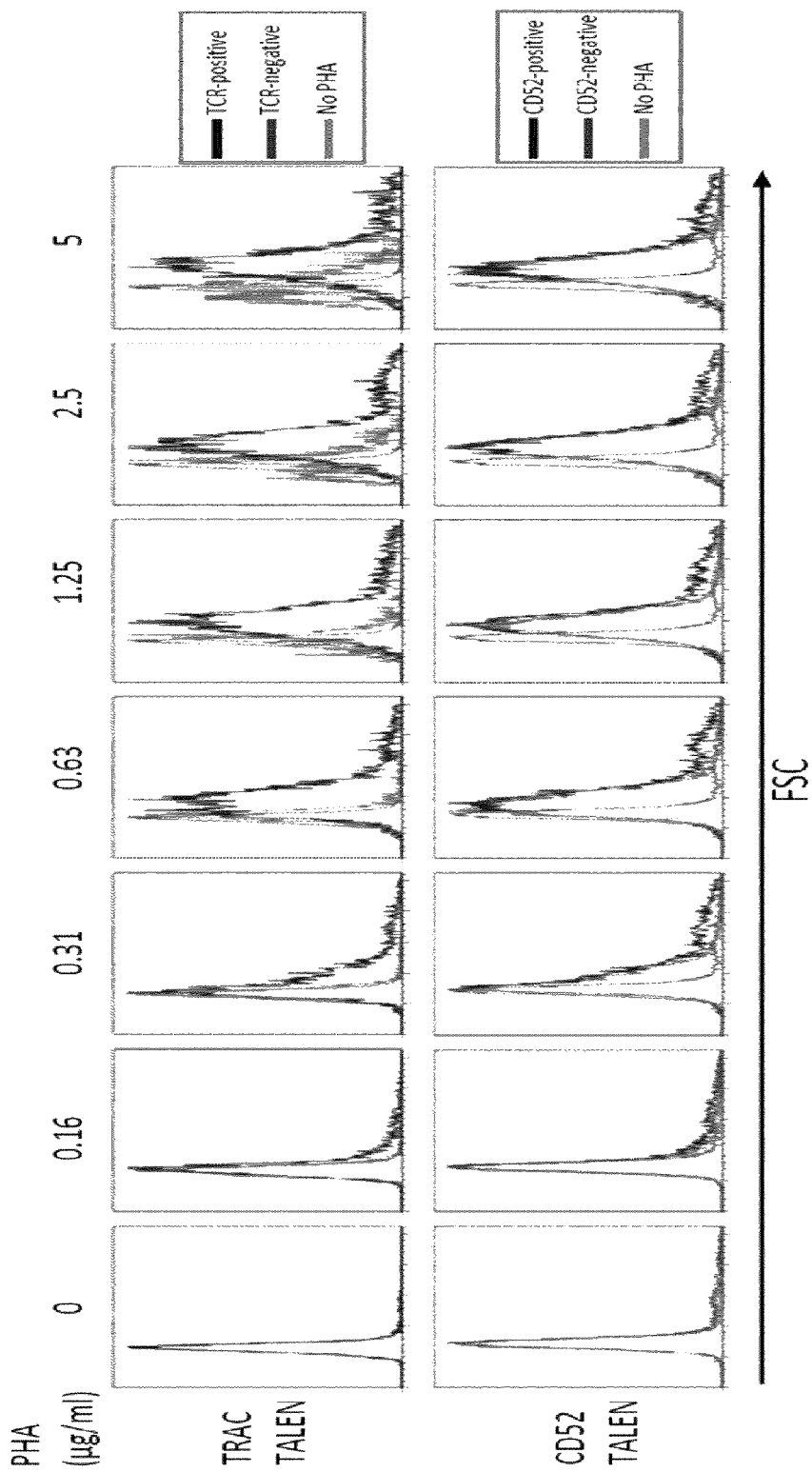
FIG. 3: Comparison of the forward side scatter (FSC) distribution, an indicator of cell size, between TCR-positive and TCR-negative cells.

The goal of TRAC gene inactivation is to render T lymphocytes unresponsive to T-cell receptor stimulation. As described in the previous paragraph, T lymphocytes were transfected with mRNA encoding TALE-nuclease cleaving TRAC. 16 days after transfection, cells were treated with up to 5 μg/ml of phytohemagglutinin (PHA, Sigma-Aldrich), a T-cell mitogen acting through the T cell receptor. Cells with a functional T-cell receptor should increase in size following PHA treatment. After three days of incubation, cells were labeled with a fluorochrome-conjugated anti-TCR antibody and analyzed by flow cytometry to compare the cell size distribution between TCR-positive and TCR-negative cells. FIG. 3 shows that TCR-positive cells significantly increase in size after PHA treatment whereas TCR-negative cells have the same size as untreated cells indicating that TRAC inactivation rendered them unresponsive to TCR-signaling.

Functional Analysis of T Cells with Targeted β2m Gene

Figure 5:
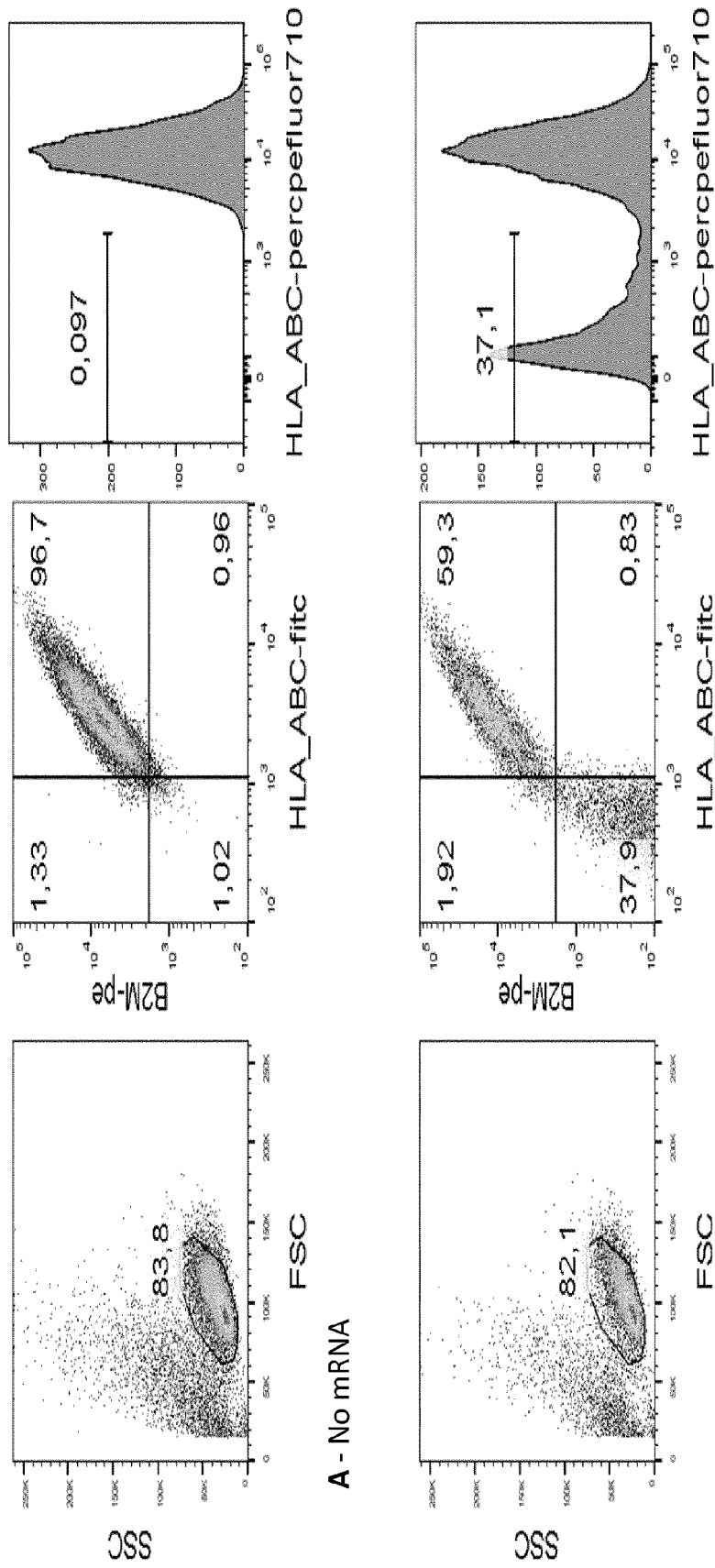
FIG. 5: Flow cytometry analysis of HLA_ABC expression on the surface of human primary T cells in: A. Control T-cells. B. following β2m TALE-nuclease mRNA electroporation.

Similarly to the above, the TALEN-transfected cells and control cells (transfected without RNA) were stained with fluorochrome labeled antibody against B2M protein as well as an antibody recognizing all three classes MHC-I molecules (HLA-A, -B or -C). TALEN transfection induced loss of surface expression of B2M and MHC-I molecules in more than 37% of T cells. See FIG. 5

Genomic Safety of β2m-TALE-Nuclease and TRAC-TALE-Nuclease in Primary T Lymphocytes As our constructs include nuclease subunits, an important question is whether multiple TALE-nuclease transfection can lead to genotoxicity and off-target cleavage at 'close match' target sequences or by mispairing of half-TALE-nucleases. To estimate the impact of TRAC-TALE-nuclease and β2m-TALE-nuclease on the integrity of the cellular genomes, we listed sequences in the human genome that presented the potential for off-site cleavage. To generate this list, we identified all the sequences in the genome with up to 4 substitutions compared to the original half targets and then identified the pairs of potential half targets in a head to head orientation with a spacer of 9 to 30 bp from each other. This analysis included sites potentially targeted by homodimers of one half-TALE-nuclease molecule or heterodimers formed by one β2m half TALE-nuclease and one TRAC half-TALE-nuclease. We scored the potential off-site targets based on the specificity data taking into account the cost of individual substitutions and the position of the substitutions (where mismatches are better tolerated for bases at the 3' end of the half target). We obtained 173 unique sequences with a score reflecting an estimation of the likelihood of cleavage. We selected the 15 top scores and analyzed by deep sequencing the frequency of mutations found at these loci in T cells simultaneously transfected with β2m and TRAC TALE-nuclease and purified by magnetic separation as β2m-negative, TCRαβ-negative. Results showed that the highest frequency of insertion/deletion is $7 \times 10^{-4}$. These results make the putative offsite target at least 600 times less likely to be mutated than the intended targets. The TALE-nuclease reagents used in this study therefore appear extremely specific.

Electroporation of T cells with a monocistronic mRNA encoding for an anti-CD19 single chain Chimeric Antigen Receptor (CAR):

$5 \times 10^6$ T cells preactivated several days (3-5) with anti-CD3/CD28 coated beads and 1L2 were resuspended in cytoporation buffer T, and electroporated in 0.4 cm cuvettes without mRNA or with of mRNA encoding a single chain CAR (SEQ ID NO: 6) using the program described in Table 7.

24 hours post electroporation, cells were stained with a fixable viability dye eFluor-780 and a PE-conjugated goat anti mouse IgG F(ab')2 fragment specific to assess the cell surface expression of the CAR on the live cells. The data is shown in the FIG. 6. A indicates that the vast majority of the live T cells electroporated with the monocitronic mRNA described previously express the CAR at their surface. 24 hours post electroporation, T cells were cocultured with Daudi (CD19+) cells for 6 hours and analyzed by flow cytometry to detect the expression of the degranulation marker CD107a at their surface (Betts, Brenchley et al. 2003).

Figure 6:
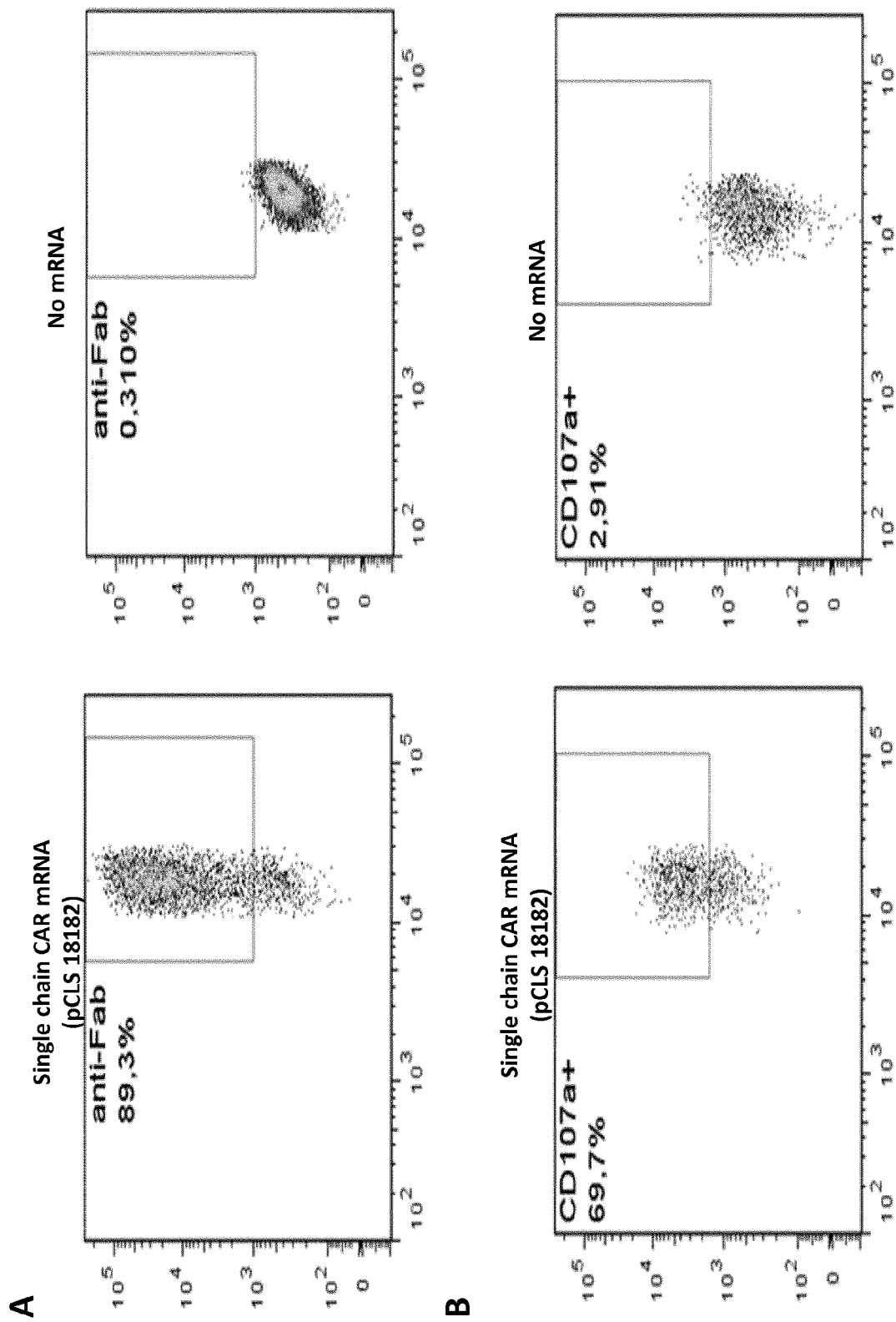
FIG. 6: A. Flow cytometry analysis of CAR expression (anti F(ab')2) after electroporation of T cells with or without mRNA encoding a single chain CAR. B. Flow cytometry analysis of CD107a expression (marker of degranulation) on electroporated T cells cocultured with daudi cells.

The data shown in FIG. 6 indicates that the majority of the cells electroporated with the monocistronic mRNA described previously degranulate in the presence of target cells expressing CD19. These results clearly demonstrate that the CAR expressed at the surface of electroporated T cells is active.

In the following examples, to prolong their survival and enhance their therapeutic activity, the inventors describe a method to prevent NK-cell mediated rejection of therapeutic allogeneic T cells by engineering the allogenic T cells through the inactivation of the B2M gene using specific TALEN, combined to either: i) the expression of a chimeric single chain molecule composed of UL18 and 132M B2M-UL18) or ii) the secretion of NKG2D ligands. The particularity resides in applying to primary T cells a mechanism occurring normally in tumor cells or virally infected cells. Thus, the mechanism of action is potentially different: in tumor cells, shedding NKG2D ligands leads to their decreased presence at the surface whereas in engineered cells, secreted the NKG2D ligand(s) would serve as a decoy for several other NKG2D ligands potentially still present at the T cell surface.

Efficient B2M Gene Knock Out Using Specific B2M TALEN.

Specific TALEN targeting a sequence (T01, SEQ ID No 81) within the first coding exon of the B2M gene (GenBank accession number NC_000015) has been produced (left DNA binding domain RVDs: NN-NN-HD-HD-NG-NG-NI-NN-HD-NG-NN-NG-NN-HD-NG-NG with SEQ ID NO: 82, and right DNA binding domain RVDs: NI-NN-HD-HD-NG-HD-HD-NI-NN-NN-HD-HD-NI-NN-NI-NG with SEQ ID NO: 83). The Table 9 below reports sequences for T01 targeting sequence, as well as for 2 additional targets T02 and T03 and their corresponding left and right TALE sequences.

TABLE 9

Description of additional β2m TALE-nucleases sequences

| Target name | SEQ ID NO: | Half TALE-nuclease sequence |
|---|---|---|
| T01 Beta2M target | 80 | TCTCGCTCCGTGGCCTTAGCTGTGCTCGCGCTACTCTCTCTTTCTGGCCTGGAGGCTA |
| T01 TALEN Beta2M LEFT | 81 | ATGGGCGATCCTAAAAAGAAACGTAAGGTCATCGATTACCCATACGATGTTCCAGATTACGCTATCGATA<br>TCGCCGATCTACGCACGCTCGGCTACAGCCAGCAGCAACAGGAGAAGATCAAACCGAAGGTTCGTTCGA<br>CAGTGGCGCAGCACCACGAGGCACTGGTCGGCCACGGGTTTACACACGCGCACATCGTTGCGTTAAGCC<br>AACACCCGGCAGCGTTAGGGACCGTCGCTGTCAAGTATCAGGACATGATCGCAGCGTTGCCAGAGGCGA<br>CACACGAAGCGATCGTTGGCGTCGGCAAACAGTGGTCCGGCGCACGCGCTCTGGAGGCCTTGCTCACGG<br>TGGCGGGAGAGTTGAGAGGTCCACCGTTACAGTTGGACACAGGCCAACTTCTCAAGATTGCAAAACGTG<br>GCGGCGTGACCGCAGTGGAGGCAGTGCATGCATGGCGCAATGCACTGACGGGTGCCCCGCTCAACTTGA<br>CCCCCCAGCAGGTGGTGGCCATCGCCAGCAATAATGGTGGCAAGCAGGCGCTGGAGACGGTCCAGCGG<br>CTGTTGCCGGTGCTGTGCCAGGCCCACGGCTTGACCCCCAGCAGGTGGTGGCCATCGCCAGCAATAATG<br>GTGGCAAGCAGGCGCTGGAGACGGTCCAGCGGCTGTTGCCGGTGCTGTGCCAGGCCCACGGCTTGACCC<br>CGGAGCAGGTGGTGGCCATCGCCAGCCACGATGGCGGCAAGCAGGCGCTGGAGACGGTCCAGCGGCTG<br>TTGCCGGTGCTGTGCCAGGCCCACGGCTTGACCCCGGAGCAGGTGGTGGCCATCGCCAGCCACGATGGC<br>GGCAAGCAGGCGCTGGAGACGGTCCAGCGGCTGTTGCCGGTGCTGTGCCAGGCCCACGGCTTGACCCCC<br>AGCAGGTGGTGGCCATCGCCAGCAATGGCGGTGGCAAGCAGGCGCTGGAGACGGTCCAGCGGCTGTT<br>GCCGGTGCTGTGCCAGGCCCACGGCTTGACCCCCAGCAGGTGGTGGCCATCGCCAGCAATGGCGGTGG<br>CAAGCAGGCGCTGGAGACGGTCCAGCGGCTGTTGCCGGTGCTGTGCCAGGCCCACGGCTTGACCCCGGA<br>GCAGGTGGTGGCCATCGCCAGCAATATTGGTGGCAAGCAGGCGCTGGAGACGGTGCAGGCGCTGTTGC<br>CGGTGCTGTGCCAGGCCCACGGCTTGACCCCCAGCAGGTGGTGGCCATCGCCAGCAATAATGGTGGCA<br>AGCAGGCGCTGGAGACGGTCCAGCGGCTGTTGCCGGTGCTGTGCCAGGCCCACGGCTTGACCCCGGAGC<br>AGGTGGTGGCCATCGCCAGCCACGATGGCGGCAAGCAGGCGCTGGAGACGGTCCAGCGGCTGTTGCCG<br>GTGCTGTGCCAGGCCCACGGCTTGACCCCCAGCAGGTGGTGGCCATCGCCAGCAATGGCGGTGGCAAG<br>CAGGCGCTGGAGACGGTCCAGCGGCTGTTGCCGGTGCTGTGCCAGGCCCACGGCTTGACCCCCAGCAG<br>GTGGTGGCCATCGCCAGCAATAATGGTGGCAAGCAGGCGCTGGAGACGGTCCAGCGGCTGTTGCCGGT<br>GCTGTGCCAGGCCCACGGCTTGACCCCCAGCAGGTGGTGGCCATCGCCAGCAATGGCGGTGGCAAG<br>GGCGCTGGAGACGGTCCAGCGGCTGTTGCCGGTGCTGTGCCAGGCCCACGGCTTGACCCCCAGCAGGT<br>GGTGGCCATCGCCAGCAATAATGGTGGCAAGCAGGCGCTGGAGACGGTCCAGCGGCTGTTGCCGGTGCT<br>GTGCCAGGCCCACGGCTTGACCCCGGAGCAGGTGGTGGCCATCGCCAGCCACGATGGCGGCAAGCAGG<br>CGCTGGAGACGGTCCAGCGGCTGTTGCCGGTGCTGTGCCAGGCCCACGGCTTGACCCCCCAGCAGGTGG<br>TGGCCATCGCCAGCAATGGCGGTGGCAAGCAGGCGCTGGAGACGGTCCAGCGGCTGTTGCCGGTGCTGT<br>GCCAGGCCCACGGCTTGACCCCTCAGCAGGTGGTGGCCATCGCCAGCAATGGCGGCGGCAGGCCGGCGC<br>TGGAGAGCATTGTTGCCCAGTTATCTCGCCCTGATCCGGCGTTGGCCGCGTTGACCAACGACCACCTCGTC<br>GCCTTGGCCTGCCTCGGCGGGCGTCCTGCGCTGGATGCAGTGAAAAAGGGATTGGGGGATCCTATCAGC<br>CGTTCCCAGCTGGTGAAGTCCGAGCTGGAGGAGAAGAAATCCGAGTTGAGGCACAAGCTGAAGTACGTG<br>CCCCACGAGTACATCGAGCTGATCGAGATCGCCCGGAACAGCACCCAGGACCGTATCCTGGAGATGAAG<br>GTGATGGAGTTCTTCATGAAGGTGTACGGCTACAGGGGCAAGCACCTGGGCGGCTCCAGGAAGCCCGAC<br>GGCGCCATCTACACCGTGGGCTCCCCCATCGACTACGGCGTGATCGTGGACACCAAGGCCTACTCCGGCG<br>GCTACAACCTGCCCATCGGCCAGGCCGACGAAATGCAGAGGTACGTGGAGGAGAACCAGACCAGGAAC<br>AAGCACATCAACCCCAACGAGTGGTGGAAGGTGTACCCCTCCAGCGTGACCGAGTTCAAGTTCCTGTTCG<br>TGTCCGGCCACTTCAAGGGCAACTACAAGGCCCAGCTGACCAGGCTGAACCACATCACCAACTGCAACGG<br>CGCCGTGCTGTCCGTGGAGGAGCTCCTGATCGGCGGCGAGATGATCAAGGCCGGCACCCTGACCCTGGA<br>GGAGGTGAGGAGGAAGTTCAACAACGGCGAGATCAACTTCGCGGCCGACTGATAA |
| T01 TALEN Beta2M RIGHT | 82 | ATGGGCGATCCTAAAAAGAAACGTAAGGTCATCGATAAGGAGACCGCCGCTGCCAAGTTCGAGAGACAG<br>CACATGGACAGCATCGATATCGCCGATCTACGCACGCTCGGCTACAGCCAGCAGCAACAGGAGAAGATC<br>AAACCGAAGGTTCGTTCGACAGTGGCGCAGCACCACGAGGCACTGGTCGGCCACGGGTTTACACACGCG<br>CACATCGTTGCGTTAAGCCAACACCCGGCAGCGTTAGGGACCGTCGCTGTCAAGTATCAGGACATGATCG<br>CAGCGTTGCCAGAGGCGACACACGAAGCGATCGTTGGCGTCGGCAAACAGTGGTCCGGCGCACGCGCTC<br>TGGAGGCCTTGCTCACGGTGGCGGGAGAGTTGAGAGGTCCACCGTTACAGTTGGACACAGGCCAACTTC<br>TCAAGATTGCAAAACGTGGCGGCGTGACCGCAGTGGAGGCAGTGCATGCATGGCGCAATGCACTGACG<br>GGTGCCCCGCTCAACTTGACCCCGGAGCAGGTGGTGGCCATCGCCAGCAATATTGGTGGCAAGCAGGCG<br>CTGGAGACGGTGCAGGCGCTGTTGCCGGTGCTGTGCCAGGCCCACGGCTTGACCCCCCAGCAGGTGGTG<br>GCCATCGCCAGCAATAATGGTGGCAAGCAGGCGCTGGAGACGGTCCAGCGGCTGTTGCCGGTGCTGTGC<br>CAGGCCCACGGCTTGACCCCGGAGCAGGTGGTGGCCATCGCCAGCCACGATGGCGGCAAGCAGGCGCT<br>GGAGACGGTCCAGCGGCTGTTGCCGGTGCTGTGCCAGGCCCACGGCTTGACCCCGGAGCAGGTGGTGG<br>CCATCGCCAGCCACGATGGCGGCAAGCAGGCGCTGGAGACGGTCCAGCGGCTGTTGCCGGTGCTGTGCC<br>AGGCCCACGGCTTGACCCCGGAGCAGGTGGTGGCCATCGCCAGCCACGATGGCGGCAAGCAGGCGCTGGA<br>GACGGTCCAGCGGCTGTTGCCGGTGCTGTGCCAGGCCCACGGCTTGACCCCGGAGCAGGTGGTGGCCAT<br>CGCCAGCAATATTGGTGGCAAGCAGGCGCTGGAGACGGTGCAGGCGCTGTTGCCGGTGCTGTGCCAGG<br>CCCACGGCTTGACCCCCCAGCAGGTGGTGGCCATCGCCAGCAATAATGGTGGCAAGCAGGCGCTGGAGA<br>CGGTCCAGCGGCTGTTGCCGGTGCTGTGCCAGGCCCACGGCTTGACCCCCAGCAGGTGGTGGCCATCG<br>CCAGCAATAATGGTGGCAAGCAGGCGCTGGAGACGGTCCAGCGGCTGTTGCCGGTGCTGTGCCAGGCCC<br>ACGGCTTGACCCCGGAGCAGGTGGTGGCCATCGCCAGCCACGATGGCGGCAAGCAGGCGCTGGAGACG<br>GTCCAGCGGCTGTTGCCGGTGCTGTGCCAGGCCCACGGCTTGACCCCGGAGCAGGTGGTGGCCATCGCC<br>AGCCACGATGGCGGCAAGCAGGCGCTGGAGACGGTCCAGCGGCTGTTGCCGGTGCTGTGCCAGGCCCA<br>CGGCTTGACCCCGGAGCAGGTGGTGGCCATCGCCAGCAATATTGGTGGCAAGCAGGCGCTGGAGACGG<br>TGCAGGCGCTGTTGCCGGTGCTGTGCCAGGCCCACGGCTTGACCCCCAGCAGGTGGTGGCCATCGCCA<br>GCAATAATGGTGGCAAGCAGGCGCTGGAGACGGTCCAGCGGCTGTTGCCGGTGCTGTGCCAGGCCCACG<br>GCTTGACCCCGGAGCAGGTGGTGGCCATCGCCAGCAATATTGGTGGCAAGCAGGCGCTGGAGACGGTG |

TABLE 9-continued

Description of additional β2m TALE-nucleases sequences

| Target name | SEQ ID NO: | Half TALE-nuclease sequence |
|---|---|---|
| | | CAGGCGCTGTTGCCGGTGCTGTGCCAGGCCCACGGCTTGACCCCTCAGCAGGTGGTGGCCATCGCCAGC<br>AATGGCGGCGGCAGGCCGGCGCTGGAGAGCATTGTTGCCCAGTTATCTCGCCCTGATCCGGCGTTGGCC<br>GCGTTGACCAACGACCACCTCGTCGCCTTGGCCTGCCTCGGCGGGCGTCCTGCGCTGGATGCAGTGAAAA<br>AGGGATTGGGGGATCCTATCAGCCGTTCCCAGCTGGTGAAGTCCGAGCTGGAGGAGAAGAAATCCGAGT<br>TGAGGCACAAGCTGAAGTACGTGCCCCACGAGTACATCGAGCTGATCGAGATCGCCCGGAACAGCACCC<br>AGGACCGTATCCTGGAGATGAAGGTGATGGAGTTCTTCATGAAGGTGTACGGCTACAGGGGCAAGCACC<br>TGGGCGGCTCCAGGAAGCCCGACGGCGCCATCTACACCGTGGGCTCCCCCATCGACTACGGCGTGATCGT<br>GGACACCAAGGCCTACTCCGGCGGCTACAACCTGCCCATCGGCCAGGCCGACGAAATGCAGAGGTACGT<br>GGAGGAGAACCAGACCAGGAACAAGCACATCAACCCCAACGAGTGGTGGAAGGTGTACCCCTCCAGCGT<br>GACCGAGTTCAAGTTCCTGTTCGTGTCCGGCCACTTCAAGGGCAACTACAAGGCCCAGCTGACCAGGCTG<br>AACCACATCACCAACTGCAACGGCGCCGTGCTGTCCGTGGAGGAGCTCCTGATCGGCGGCGAGATGATC<br>AAGGCCGGCACCCTGACCCTGGAGGAGGTGAGGAGGAAGTTCAACAACGGCGAGATCAACTTCGCGGC<br>CGACTGATAA |
| T02 Beta2M target | 83 | TCCAAAGATTCAGGTTTACTCACGTCATCCAGCAGAGAATGGAAAGTCAA |
| T02 TALEN Beta2M LEFT | 84 | ATGGGCGATCCTAAAAAGAAACGTAAGGTCATCGATTACCCATACGATGTTCCAGATTACGCTATCGATA<br>TCGCCGATCTACGCACGCTCGGCTACAGCCAGCAGCAACAGGAGAAGATCAAACCGAAGGTTCGTTCGA<br>CAGTGGCGCAGCACCACGAGGCACTGGTCGGCCACGGGTTTACACACGCGCACATCGTTGCGTTAAGCC<br>AACACCCGGCAGCGTTAGGGACCGTCGCTGTCAAGTATCAGGACATGATCGCAGCGTTGCCAGAGGCGA<br>CACACGAAGCGATCGTTGGCGTCGGCAAACAGTGGTCCGGCGCACGCGCTCTGGAGGCCTTGCTCACGG<br>TGGCGGGAGAGTTGAGAGGTCCACCGTTACAGTTGGACACAGGCCAACTTCTCAAGGATTGCAAAACGTG<br>GCGGCGTGACCGCAGTGGAGGCAGTGCATGCATGGCGCAATGCACTGACGGGTGCCCCGCTCAACTTGA<br>CCCCGGAGCAGGTGGTGGCCATCGCCAGCCACGATGGCGGCAAGCAGGCGCTGGAGACGGTCCAGCGG<br>CTGTTGCCGGTGCTGTGCCAGGCCCACGGCTTGACCCCGGAGCAGGTGGTGGCCATCGCCAGCCACGAT<br>GGCGGCAAGCAGGCGCTGGAGACGGTCCAGCGGCTGTTGCCGGTGCTGTGCCAGGCCCACGGCTTGAC<br>CCCGGAGCAGGTGGTGGCCATCGCCAGCAATATTGGTGGCAAGCAGGCGCTGGAGACGGTGCAGGCGC<br>TGTTGCCGGTGCTGTGCCAGGCCCACGGCTTGACCCCGGAGCAGGTGGTGGCCATCGCCAGCAATATTG<br>GTGGCAAGCAGGCGCTGGAGACGGTGCAGGCGCTGTTGCCGGTGCTGTGCCAGGCCCACGGCTTGACCC<br>CGGAGCAGGTGGTGGCCATCGCCAGCAATATTGGTGGCAAGCAGGCGCTGGAGACGGTGCAGGCGCTG<br>TTGCCGGTGCTGTGCCAGGCCCACGGCTTGACCCCCAGCAGGTGGTGGCCATCGCCAGCAATAATGGT<br>GGCAAGCAGGCGCTGGAGACGGTCCAGCGGCTGTTGCCGGTGCTGTGCCAGGCCCACGGCTTGACCCCG<br>GAGCAGGTGGTGGCCATCGCCAGCAATATTGGTGGCAAGCAGGCGCTGGAGACGGTGCAGGCGCTGTT<br>GCCGGTGCTGTGCCAGGCCCACGGCTTGACCCCCAGCAGGTGGTGGCCATCGCCAGCAATGGCGGTGG<br>CAAGCAGGCGCTGGAGACGGTCCAGCGGCTGTTGCCGGTGCTGTGCCAGGCCCACGGCTTGACCCCCCA<br>GCAGGTGGTGGCCATCGCCAGCAATGGCGGTGGCAAGCAGGCGCTGGAGACGGTCCAGCGGCTGTTGC<br>CGGTGCTGTGCCAGGCCCACGGCTTGACCCCGGAGCAGGTGGTGGCCATCGCCAGCCACGATGGCGGCA<br>AGCAGGCGCTGGAGACGGTCCAGCGGCTGTTGCCGGTGCTGTGCCAGGCCCACGGCTTGACCCCGGAGC<br>AGGTGGTGGCCATCGCCAGCAATATTGGTGGCAAGCAGGCGCTGGAGACGGTGCAGGCGCTGTTGCC<br>GTGCTGTGCCAGGCCCACGGCTTGACCCCCAGCAGGTGGTGGCCATCGCCAGCAATAATGGTGGCAAG<br>CAGGCGCTGGAGACGGTCCAGCGGCTGTTGCCGGTGCTGTGCCAGGCCCACGGCTTGACCCCCAGCAG<br>GTGGTGGCCATCGCCAGCAATAATGGTGGCAAGCAGGCGCTGGAGACGGTCCAGCGGCTGTTGCCGGT<br>GCTGTGCCAGGCCCACGGCTTGACCCCCAGCAGGTGGTGGCCATCGCCAGCAATGGCGGTGGCAAGCA<br>GGCGCTGGAGACGGTCCAGCGGCTGTTGCCGGTGCTGTGCCAGGCCCACGGCTTGACCCCCCAGCAGGT<br>GGTGGCCATCGCCAGCAATGGCGGTGGCAAGCAGGCGCTGGAGACGGTCCAGCGGCTGTTGCCGGTGC<br>TGTGCCAGGCCCACGGCTTGACCCCTCAGCAGGTGGTGGCCATCGCCAGCAATGGCGGCGGCAGGCCGG<br>CGCTGGAGAGCATTGTTGCCCAGTTATCTCGCCCTGATCCGGCGTTGGCCGCGTTGACCAACGACCACCT<br>CGTCGCCTTGGCCTGCCTCGGCGGGCGTCCTGCGCTGGATGCAGTGAAAAAGGGATTGGGGGATCCTAT<br>CAGCCGTTCCCAGCTGGTGAAGTCCGAGCTGGAGGAGAAGAAATCCGAGTTGAGGCACAAGCTGAAGTA<br>CGTGCCCCACGAGTACATCGAGCTGATCGAGATCGCCCGGAACAGCACCCAGGACCGTATCCTGGAGAT<br>GAAGGTGATGGAGTTCTTCATGAAGGTGTACGGCTACAGGGGCAAGCACCTGGGCGGCTCCAGGAAGC<br>CCGACGGCGCCATCTACACCGTGGGCTCCCCCATCGACTACGGCGTGATCGTGGACACCAAGGCCTACTC<br>CGGCGGCTACAACCTGCCCATCGGCCAGGCCGACGAAATGCAGAGGTACGTGGAGGAGAACCAGACCA<br>GGAACAAGCACATCAACCCCAACGAGTGGTGGAAGGTGTACCCCTCCAGCGTGACCGAGTTCAAGTTCCT<br>GTTCGTGTCCGGCCACTTCAAGGGCAACTACAAGGCCCAGCTGACCAGGCTGAACCACATCACCAACTGC<br>AACGGCGCCGTGCTGTCCGTGGAGGAGCTCCTGATCGGCGGCGAGATGATCAAGGCCGGCACCCTGACC<br>CTGGAGGAGGTGAGGAGGAAGTTCAACAACGGCGAGATCAACTTCGCGGCCGACTGATAA |
| T02 TALEN Beta2M RIGHT | 85 | ATGGGCGATCCTAAAAAGAAACGTAAGGTCATCGATAAGGAGACCGCCGCTGCCAAGTTCGAGAGACAG<br>CACATGGACAGCATCGATATCGCCGATCTACGCACGCTCGGCTACAGCCAGCAGCAACAGGAGAAGATC<br>AAACCGAAGGTTCGTTCGACAGTGGCGCAGCACCACGAGGCACTGGTCGGCCACGGGTTTACACACGCG<br>CACATCGTTGCGTTAAGCCAACACCCGGCAGCGTTAGGGACCGTCGCTGTCAAGTATCAGGACATGATCG<br>CAGCGTTGCCAGAGGCGACACACGAAGCGATCGTTGGCGTCGGCAAACAGTGGTCCGGCGCACGCGCTC<br>TGGAGGCCTTGCTCACGGTGGCGGGAGAGTTGAGAGGTCCACCGTTACAGTTGGACACAGGCCAACTTC<br>TCAAGATTGCAAAACGTGGCGGCGTGACCGCAGTGGAGGCAGTGCATGCATGGCGCAATGCACTGACG<br>GGTGCCCCGCTCAACTTGACCCCCAGCAGGTGGTGGCCATCGCCAGCAATAATGGTGGCAAGCAGGCG<br>CTGGAGACGGTCCAGCGGCTGTTGCCGGTGCTGTGCCAGGCCCACGGCTTGACCCCGGAGCAGGTGGTG<br>GCCATCGCCAGCAATATTGGTGGCAAGCAGGCGCTGGAGACGGTGCAGGCGCTGTTGCCGGTGCTGTGC<br>CAGGCCCACGGCTTGACCCCGGAGCAGGTGGTGGCCATCGCCAGCCACGATGGCGGCAAGCAGGCGCT<br>GGAGACGGTCCAGCGGCTGTTGCCGGTGCTGTGCCAGGCCCACGGCTTGACCCCCAGCAGGTGGTGGC<br>CATCGCCAGCAATGGCGGTGGCAAGCAGGCGCTGGAGACGGTCCAGCGGCTGTTGCCGGTGCTGTGCCA<br>GGCCCACGGCTTGACCCCCAGCAGGTGGTGGCCATCGCCAGCAATGGCGGTGGCAAGCAGGCGCTGG<br>AGACGGTCCAGCGGCTGTTGCCGGTGCTGTGCCAGGCCCACGGCTTGACCCCCCAGCAGGTGGTGGCCA |

TABLE 9-continued

Description of additional β2m TALE-nucleases sequences

| Target name | SEQ ID NO: | Half TALE-nuclease sequence |
|---|---|---|
| | | TCGCCAGCAATGGCGGTGGCAAGCAGGCGCTGGAGACGGTCCAGCGGCTGTTGCCGGTGCTGTGCCAG<br>GCCCACGGCTTGACCCCGGAGCAGGTGGTGGCCATCGCCAGCCACGATGGCGGCAAGCAGGCGCTGGA<br>GACGGTCCAGCGGCTGTTGCCGGTGCTGTGCCAGGCCCACGGCTTGACCCCGGAGCAGGTGGTGGCCAT<br>CGCCAGCCACGATGGCGGCAAGCAGGCGCTGGAGACGGTCCAGCGGCTGTTGCCGGTGCTGTGCCAGG<br>CCCACGGCTTGACCCCGGAGCAGGTGGTGGCCATCGCCAGCAATATTGGTGGCAAGCAGGCGCTGGAGA<br>CGGTGCAGGCGCTGTTGCCGGTGCTGTGCCAGGCCCACGGCTTGACCCCCAGCAGGTGGTGGCCATCG<br>CCAGCAATGGCGGTGGCAAGCAGGCGCTGGAGACGGTCCAGCGGCTGTTGCCGGTGCTGTGCCAGGCC<br>CACGGCTTGACCCCCAGCAGGTGGTGGCCATCGCCAGCAATGGCGGTGGCAAGCAGGCGCTGGAGAC<br>GGTCCAGCGGCTGTTGCCGGTGCTGTGCCAGGCCCACGGCTTGACCCCGGAGCAGGTGGTGGCCATCGC<br>CAGCCACGATGGCGGCAAGCAGGCGCTGGAGACGGTCCAGCGGCTGTTGCCGGTGCTGTGCCAGGCCC<br>ACGGCTTGACCCCCAGCAGGTGGTGGCCATCGCCAGCAATGGCGGTGGCAAGCAGGCGCTGGAGACG<br>GTCCAGCGGCTGTTGCCGGTGCTGTGCCAGGCCCACGGCTTGACCCCGGAGCAGGTGGTGGCCATCGCC<br>AGCCACGATGGCGGCAAGCAGGCGCTGGAGACGGTCCAGCGGCTGTTGCCGGTGCTGTGCCAGGCCCA<br>CGGCTTGACCCCCAGCAGGTGGTGGCCATCGCCAGCAATGGCGGTGGCAAGCAGGCGCTGGAGACGG<br>TCCAGCGGCTGTTGCCGGTGCTGTGCCAGGCCCACGGCTTGACCCCTCAGCAGGTGGTGGCCATCGCCAG<br>CAATGGCGGCAGGCCGGCGCTGGAGAGCATTGTTGCCCAGTTATCTCGCCCTGATCCGGCGTTGGC<br>CGCGTTGACCAACGACCACCTCGTCGCCTTGGCCTGCCTCGGCGGGCGTCCTGCGCTGGATGCAGTGAAA<br>AAGGGATTGGGGGATCCTATCAGCCGTTCCCAGCTGGTGAAGTCCGAGCTGGAGGAGAAGAAATCCGA<br>GTTGAGGCACAAGCTGAAGTACGTGCCCCACGAGTACATCGAGCTGATCGAGATCGCCCGGAACAGCAC<br>CCAGGACCGTATCCTGGAGATGAAGGTGATGGAGTTCTTCATGAAGGTGTACGGCTACAGGGGCAAGCA<br>CCTGGGCGGCTCCAGGAAGCCCGACGGCGCCATCTACACCGTGGGCTCCCCCATCGACTACGGCGTGATC<br>GTGGACACCAAGGCCTACTCCGGCGGCTACAACCTGCCCATCGGCCAGGCCGACGAAATGCAGAGGTAC<br>GTGGAGGAGAACCAGACCAGGAACAAGCACATCAACCCCAACGAGTGGTGGAAGGTGTACCCCTCCAGC<br>GTGACCGAGTTCAAGTTCCTGTTCGTGTCCGGCCACTTCAAGGGCAACTACAAGGCCCAGCTGACCAGGC<br>TGAACCACATCACCAACTGCAACGGCGCCGTGCTGTCCGTGGAGGAGCTCCTGATCGGCGGCGAGATGA<br>TCAAGGCCGGCACCCTGACCCTGGAGGAGGTGAGGAGGAAGTTCAACAACGGCGAGATCAACTTCGCG<br>GCCGACTGATAA |
| T03<br>Beta2M<br>target | 86 | TTAGCTGTGCTCGCGCTACTCTCTCTTTCTGGCCTGGAGGCTATCCA |
| T03<br>TALEN<br>Beta2M<br>LEFT | 87 | ATGGGCGATCCTAAAAAGAAACGTAAGGTCATCGATTACCCATACGATGTTCCAGATTACGCTATCGATA<br>TCGCCGATCTACGCACGCTCGGCTACAGCCAGCAGCAACAGGAGAAGATCAAACCGAAGGTTCGTTCGA<br>CAGTGGCGCAGCACCACGAGGCACTGGTCGGCCACGGGTTTACACACGCGCACATCGTTGCGTTAAGCC<br>AACACCCGGCAGCGTTAGGGACCGTCGCTGTCAAGTATCAGGACATGATCGCAGCGTTGCCAGAGGCGA<br>CACACGAAGCGATCGTTGGCGTCGGCAAACAGTGGTCCGGCGCACGCGCTCTGGAGGCCTTGCTCACGG<br>TGGCGGGAGAGTTGAGAGGTCCACCGTTACAGTTGGACACAGGCCAACTTCTCAAGATTCAAAACGTG<br>GCGGCGTGACCGCAGTGGAGGCAGTGCATGCATGGCGCAATGCACTGACGGGTGCCCCGCTCAACTTGA<br>CCCCGGAGCAGGTGGTGGCCATCGCCAGCAATATTGGTGGCAAGCAGGCGCTGGAGACGGTGCAGGCG<br>CTGTTGCCGGTGCTGTGCCAGGCCCACGGCTTGACCCCCCAGCAGGTGGTGGCCATCGCCAGCAATAATG<br>GTGGCAAGCAGGCGCTGGAGACGGTCCAGCGGCTGTTGCCGGTGCTGTGCCAGGCCCACGGCTTGACCC<br>CGGAGCAGGTGGTGGCCATCGCCAGCCACGATGGCGGCAAGCAGGCGCTGGAGACGGTCCAGCGGCTG<br>TTGCCGGTGCTGTGCCAGGCCCACGGCTTGACCCCCCAGCAGGTGGTGGCCATCGCCAGCAATGGCGGT<br>GGCAAGCAGGCGCTGGAGACGGTCCAGCGGCTGTTGCCGGTGCTGTGCCAGGCCCACGGCTTGACCCCC<br>CAGCAGGTGGTGGCCATCGCCAGCAATAATGGTGGCAAGCAGGCGCTGGAGACGGTCCAGCGGCTGTT<br>GCCGGTGCTGTGCCAGGCCCACGGCTTGACCCCCAGCAGGTGGTGGCCATCGCCAGCAATGGCGGTGG<br>CAAGCAGGCGCTGGAGACGGTCCAGCGGCTGTTGCCGGTGCTGTGCCAGGCCCACGGCTTGACCCCCCA<br>GCAGGTGGTGGCCATCGCCAGCAATAATGGTGGCAAGCAGGCGCTGGAGACGGTCCAGCGGCTGTTGCC<br>GGTGCTGTGCCAGGCCCACGGCTTGACCCCGGAGCAGGTGGTGGCCATCGCCAGCCACGATGGCGGCA<br>AGCAGGCGCTGGAGACGGTCCAGCGGCTGTTGCCGGTGCTGTGCCAGGCCCACGGCTTGACCCCCCAGC<br>AGGTGGTGGCCATCGCCAGCAATGGCGGTGGCAAGCAGGCGCTGGAGACGGTCCAGCGGCTGTTGCCG<br>GTGCTGTGCCAGGCCCACGGCTTGACCCCGGAGCAGGTGGTGGCCATCGCCAGCCACGATGGCGGCAAG<br>CAGGCGCTGGAGACGGTCCAGCGGCTGTTGCCGGTGCTGTGCCAGGCCCACGGCTTGACCCCCCAGCAG<br>GTGGTGGCCATCGCCAGCAATAATGGTGGCAAGCAGGCGCTGGAGACGGTCCAGCGGCTGTTGCCGGT<br>GCTGTGCCAGGCCCACGGCTTGACCCCGGAGCAGGTGGTGGCCATCGCCAGCCACGATGGCGGCAAGCA<br>GGCGCTGGAGACGGTCCAGCGGCTGTTGCCGGTGCTGTGCCAGGCCCACGGCTTGACCCCCCAGCAGGT<br>GGTGGCCATCGCCAGCAATAATGGTGGCAAGCAGGCGCTGGAGACGGTCCAGCGGCTGTTGCCGGTGCT<br>GTGCCAGGCCCACGGCTTGACCCCGGAGCAGGTGGTGGCCATCGCCAGCCACGATGGCGGCAAGCAGG<br>CGCTGGAGACGGTCCAGCGGCTGTTGCCGGTGCTGTGCCAGGCCCACGGCTTGACCCCCCAGCAGGTGG<br>TGGCCATCGCCAGCAATGGCGGTGGCAAGCAGGCGCTGGAGACGGTCCAGCGGCTGTTGCCGGTGCTGT<br>GCCAGGCCCACGGCTTGACCCCTCAGCAGGTGGTGGCCATCGCCAGCAATGGCGGCGGCAGGCCGGCGC<br>TGGAGAGCATTGTTGCCCAGTTATCTCGCCCTGATCCGGCGTTGGCCGCGTTGACCAACGACCACCTCGTC<br>GCCTTGGCCTGCCTCGGCGGGCGTCCTGCGCTGGATGCAGTGAAAAAGGGATTGGGGGATCCTATCAGC<br>CGTTCCCAGCTGGTGAAGTCCGAGCTGGAGGAGAAGAAATCCGAGTTGAGGCACAAGCTGAAGTACGTG<br>CCCCACGAGTACATCGAGCTGATCGAGATCGCCCGGAACAGCACCCAGGACCGTATCCTGGAGATGAAG<br>GTGATGGAGTTCTTCATGAAGGTGTACGGCTACAGGGGCAAGCACCTGGGCGGCTCCAGGAAGCCCGAC<br>GGCGCCATCTACACCGTGGGCTCCCCCATCGACTACGGCGTGATCGTGGACACCAAGGCCTACTCCGGCG<br>GCTACAACCTGCCCATCGGCCAGGCCGACGAAATGCAGAGGTACGTGGAGGAGAACCAGACCAGGAAC<br>AAGCACATCAACCCCAACGAGTGGTGGAAGGTGTACCCCTCCAGCGTGACCGAGTTCAAGTTCCTGTTCG<br>TGTCCGGCCACTTCAAGGGCAACTACAAGGCCCAGCTGACCAGGCTGAACCACATCACCAACTGCAACGG<br>CGCCGTGCTGTCCGTGGAGGAGCTCCTGATCGGCGGCGAGATGATCAAGGCCGGCACCCTGACCCTGGA<br>GGAGGTGAGGAGGAAGTTCAACAACGGCGAGATCAACTTCGCGGCCGACTGATAA |

TABLE 9-continued

Description of additional β2m TALE-nucleases sequences

| Target name | SEQ ID NO: | Half TALE-nuclease sequence |
|---|---|---|
| T03 TALEN Beta2M RIGHT | 88 | ATGGGCGATCCTAAAAAGAAACGTAAGGTCATCGATAAGGAGACCGCCGCTGCCAAGTTCGAGAGACAG<br>CACATGGACAGCATCGATATCGCCGATCTACGCACGCTCGGCTACAGCCAGCAGCAACAGGAGAAGATC<br>AAACCGAAGGTTCGTTCGACAGTGGCGCAGCACCACGAGGCACTGGTCGGCCACGGGTTTACACACGCG<br>CACATCGTTGCGTTAAGCCAACACCCGGCAGCGTTAGGGACCGTCGCTGTCAAGTATCAGGACATGATCG<br>CAGCGTTGCCAGAGGCGACACACGAAGCGATCGTTGGCGTCGGCAAACAGTGGTCCGGCGCACGCGCTC<br>TGGAGGCCTTGCTCACGGTGGCGGGAGAGTTGAGAGGTCCACCGTTACAGTTGGACACAGGCCAACTTC<br>TCAAGATTGCAAAACGTGGCGGCGTGACCGCAGTGGAGGCAGTGCATGCATGGCGCAATGCACTGACG<br>GGTGCCCCGCTCAACTTGACCCCCCAGCAGGTGGTGGCCATCGCCAGCAATAATGGTGGCAAGCAGGCG<br>CTGGAGACGGTCCAGCGGCTGTTGCCGGTGCTGTGCCAGGCCCACGGCTTGACCCCCCAGCAGGTGGTG<br>GCCATCGCCAGCAATAATGGTGGCAAGCAGGCGCTGGAGACGGTCCAGCGGCTGTTGCCGGTGCTGTGC<br>CAGGCCCACGGCTTGACCCCGGAGCAGGTGGTGGCCATCGCCAGCAATATTGGTGGCAAGCAGGCGCTG<br>GAGACGGTGCAGGCGCTGTTGCCGGTGCTGTGCCAGGCCCACGGCTTGACCCCCCAGCAGGTGGTGGCC<br>ATCGCCAGCAATGGCGGTGGCAAGCAGGCGCTGGAGACGGTCCAGCGGCTGTTGCCGGTGCTGTGCCA<br>GGCCCACGGCTTGACCCCGGAGCAGGTGGTGGCCATCGCCAGCAATATTGGTGGCAAGCAGGCGCTGGA<br>GACGGTGCAGGCGCTGTTGCCGGTGCTGTGCCAGGCCCACGGCTTGACCCCCAGCAGGTGGTGGCCAT<br>CGCCAGCAATAATGGTGGCAAGCAGGCGCTGGAGACGGTCCAGCGGCTGTTGCCGGTGCTGTGCCAGGC<br>CCACGGCTTGACCCCGGAGCAGGTGGTGGCCATCGCCAGCCACGATGGCGGCAAGCAGGCGCTGGAGA<br>CGGTCCAGCGGCTGTTGCCGGTGCTGTGCCAGGCCCACGGCTTGACCCCGGAGCAGGTGGTGGCCATCG<br>CCAGCCACGATGGCGGCAAGCAGGCGCTGGAGACGGTCCAGCGGCTGTTGCCGGTGCTGTGCCAGGCCC<br>ACGGCTTGACCCCCCAGCAGGTGGTGGCCATCGCCAGCAATGGCGGTGGCAAGCAGGCGCTGGAGACG<br>GTCCAGCGGCTGTTGCCGGTGCTGTGCCAGGCCCACGCTTGACCCCGGAGCAGGTGGTGGCCATCGCC<br>AGCCACGATGGCGGCAAGCAGGCGCTGGAGACGGTCCAGCGGCTGTTGCCGGTGCTGTGCCAGGCCCA<br>CGGCTTGACCCCGGAGCAGGTGGTGGCCATCGCCAGCCACGATGGCGGCAAGCAGGCGCTGGAGACGG<br>TCCAGCGGCTGTTGCCGGTGCTGTGCCAGGCCCACGGCTTGACCCCGGAGCAGGTGGTGGCCATCGCCA<br>GCAATATTGGTGGCAAGCAGGCGCTGGAGACGGTGCAGGCGCTGTTGCCGGTGCTGTGCCAGGCCCAC<br>GGCTTGACCCCCCAGCAGGTGGTGGCCATCGCCAGCAATAATGGTGGCAAGCAGGCGCTGGAGACGGTC<br>CAGCGGCTGTTGCCGGTGCTGTGCCAGGCCCACGGCTTGACCCCCAGCAGGTGGTGGCCATCGCCAGC<br>AATAATGGTGGCAAGCAGGCGCTGGAGACGGTCCAGCGGCTGTTGCCGGTGCTGTGCCAGGCCCACGGC<br>TTGACCCCGGAGCAGGTGGTGGCCATCGCCAGCCACGATGGCGGCAAGCAGGCGCTGGAGACGGTCCA<br>GCGGCTGTTGCCGGTGCTGTGCCAGGCCCACGGCTTGACCCCTCAGCAGGTGGTGGCCATCGCCAGCAA<br>TGGCGGCGGCAGGCCGGCGCTGGAGAGCATTGTTGCCCAGTTATCTCGCCCTGATCCGGCGTTGGCCGC<br>GTTGACCAACGACCACCTCGTCGCCTTGGCCTGCCTCGGCGGGCGTCCTGCGCTGGATGCAGTGAAAAAG<br>GGATTGGGGGATCCTATCAGCCGTTCCCAGCTGGTGAAGTCCGAGCTGGAGGAGAAGAAATCCAGGTTG<br>AGGCACAAGCTGAAGTACGTGCCCCACGAGTACATCGAGCTGATCGAGATCGCCCGGAACAGCACCCAG<br>GACCGTATCCTGGAGATGAAGGTGATGGAGTTCTTCATGAAGGTGTACGGCTACAGGGGCAAGCACCTG<br>GGCGGCTCCAGGAAGCCCGACGGCGCCATCTACACCGTGGGCTCCCCCATCGACTACGGCGTGATCGTG<br>GACACCAAGGCCTACTCCGGCGGCTACAACCTGCCCATCGGCCAGGCCGACGAAATGCAGAGGTACGTG<br>GAGGAGAACCAGACCAGGAACAAGCACATCAACCCCAACGAGTGGTGGAAGGTGTACCCCTCCAGCGTG<br>ACCGAGTTCAAGTTCCTGTTCGTGTCCGGCCACTTCAAGGGCAACTACAAGGCCCAGCTGACCAGGCTGA<br>ACCACATCACCAACTGCAACGGCGCCGTGCTGTCCGTGGAGGAGCTCCTGATCGGCGGCGAGATGATCA<br>AGGCCGGCACCCTGACCCTGGAGGAGGTGAGGAGGAAGTTCAACAACGGCGAGATCAACTTCGCGGCC<br>GACTGATAA |

Figure 10:
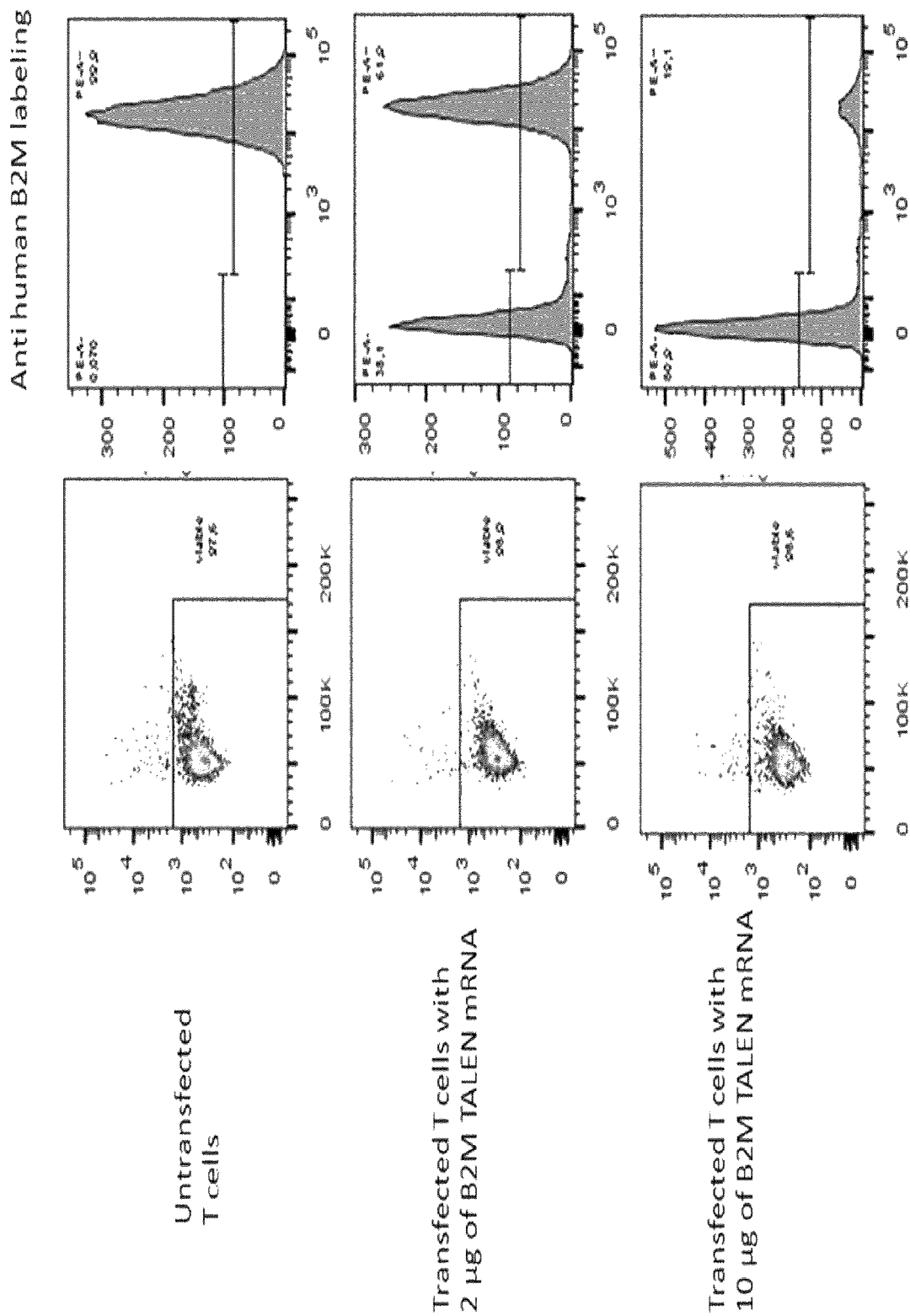
FIG. 10: FACS analysis of β2-m expression in T cells. Untransfected (top) and transfected T cells (middle and bottom) are analysed by FACS for viability (left) and β2-m expression (right).

To test the ability of this B2M specific TALEN to promote error-prone NHEJ events at the B2M locus, 2 or 10 μg of mRNA encoding TALEN were electroporated in Primary T cells using Pulse Agile technology according to the manufacturer protocol. Three days post transfection, cells were recovered and labeled with a specific β2-microglobulin antibody coupled to the PhycoErythrin fluorochrome. Cells are then analyzed by flow cytometry for viability and β2-m expression. The results are shown on FIG. 10. On the top panel, nearly 100% of untransfected T cells express β2-m (top right panel). Transfection of T cells with the specific B2M TALEN reduces dramatically β 2-m expression since 38% (middle right) and 80% of T cells (bottom right panel) become beta2-m negative when transfected with 2 μg or 10 μg of TALEN mRNA respectively. These data indicates that B2M knock-out in T cells can be achieved with high efficacy.

Production and Expression of the Single Chain Molecule B2M-UL18 in T Cells

HCMV UL18 encodes a type I transmembrane glycoprotein that shares a high level of AA sequence identity with MHC Class I molecules that associates with beta2-m and binds endogenous peptides. Since our goal is to express this molecule in T cells where B2M gene has been invalidated, our strategy is to produce a chimeric molecule where beta2-m and UL18 is fused as a single chain polypeptide. SEQ ID No 89 shows the amino-acid sequence of the chimeric protein. Lentiviral particles containing the chimeric B2M-UL18 are transduced into T cells. Expression of transgene is monitored by FACS analysis using a beta2-m antibody. The results from this experiment aim to show that a B2M-UL18 chimeric protein is efficiently expressed in T cells.

Production and Expression of NKG2D Ligands in T Cells

NKG2D natural ligands are transmembrane or GPI-anchored proteins. In order to achieve secretion of these molecules by T cells, the extra-cellular domains of NKG2D ligands have been fused in their N-terminus to a secretory peptide form. Amino-acid sequences of secreted chimeric NKG2D ligands are listed below (SEQ ID NO:90 to SEQ ID NO:97). Lentiviral particles containing the chimeric NKG2D ligands are transduced into T cells. Expression of transgene in culture supernatant is monitored by Western Blot analysis using specific antibodies. The results from this experiment aim to show that chimeric NKG2D ligand proteins are efficiently expressed in T cells.

Beta2-M Deficient CART Cells are not Recognized by Allogenic T Cells.

PBMCs from healthy donor A is co-cultured with irradiated or mitomycin-treated engineered beta2-m deficient T cells from donor B. As a control, PBMCs from healthy donor A is co-cultured with irradiated or mitomycin-treated engineered beta2-m positive T cells from donor B. 7 days later, cells proliferation from donor A is measured by XTT colorimetric assay or by CFSE dilution (FACS analysis). Although cell proliferation is observed in control, no or limited cell proliferation is observed when engineered T cells do not express beta2-m. The results from this experiment aim to show that alloreactive T cells are not able to recognize and proliferate against beta2-m deficient T cells. Efficient Inhibition of NK Mediated Engineered T Cells Lysis NK cells are purified from healthy donor A PBMCs. As targets, engineered T cells from healthy donor B are produced and listed below. a) engineered T cells (negative control), b) beta2-m deficient engineered T cells (positive control), c) beta2-m deficient engineered T cells expressing B2M-UL18 (SEQ ID No 89), d-k) beta2-m deficient engineered T cells expressing respectively SP-MICAed (SEQ ID No 90), SP-MICBed (SEQ ID No 91), SP-ULBP1ed (SEQ ID No 92), SP-ULBP2ed (SEQ ID No 93), SP-ULBP3ed (SEQ ID No 94), SP-N2DL4ed (SEQID No 95), SP-RET1Ged (SEQ ID No 96), SP-RAETILed (SEQ ID No 97). These sequences are reported in the following Table 10.

TABLE 10

Polypeptide sequence of a viral MHC homolog (UL18) and a panel of NKG2D ligands to be expressed according to the present invention.

| | SEQ ID NO: | Polypeptide sequence |
|---|---|---|
| Chimeric B2M-UL18 | 89 | MALPVTALLLPLALLLHAARPSRSVALAVLALLSLSGLEAIQRTPKIQVYSRHPAENGKSNFLNCYVSGFHPSDIEVDLLKNGERIEKVEHSDLSFSKDWSFYLLYYTEFTPTEKDEYACRVNHVTLSQPKIVKWDRDMGGGGSGGGGSGGGGSGGGGSMTMWCLTLFVLWMLRVVGMHVLRYGYTGIFDDTSHMTLTVVGIFDGQHFFTYHVNSSDKASSRANGTISWMANVSAAYPTYLDGERAKGDLIFNQTEQNLLELEIALGYRSQSVLTWTHECNTTENGSFVAGYEGFGWDGETLMELKDNLTLWTGPNYEISWLKQNKTYIDGKIKNISEGDTTIQRNYLKGNCTQWSVIYSGFQTPVTHPVVKGGVRNQNDNRAEAFCTSYGFFPGEINITFIHYGNKAPDDSEPQCNPLLPTFDGTFHQGCYVAIFCNQNYTCRVTHGNWTVEIPISVTSPDDSSSGEVPDHPTANKRYNTMTISSVLLALLLCALLFAFLHYFTTLKQYLRNLAFAWRYRKVRSS |
| SP-MICAed | 90 | MGGVLLTQRTLLSLVLALLFPSMASMEPHSLRYNLTVLSWDGSVQSGFLTEVHLDGQPFLRCDRQKCRAKPQGQWAEDVLGNKTWDRETRDLTGNGKDLRMTLAHIKDQKEGLHSLQEIRVCEIHEDNSTRSSQHFYYDGELFLSQNLETKEWTMPQSSRAQTLAMNVRNFLKEDAMKTKTHYHAMHADCLQELRRYLKSGVVLRRTVPPMVNVTRSEASEGNITVTCRASGFYPWNITLSWRQDGVSLSHDTQQWGDVLPDGNGTYQTWVATRICQGEEQRFTCYMEHSGNHSTHPVPSGKVLVLQSHW |
| SP-MICBed | 91 | MGGVLLTQRTLLSLVLALLFPSMASMAEPHSLRYNLMVLSQDESVQSGFLAEGHLDGQPFLRYDRQKRRAKPQGQWAEDVLGAKTWDTETEDLTENGQDLRRTLTHIKDQKGGLHSLQEIRVCEIHEDSSTRGSRHFYYDGELFLSQNLETQESTVPQSSRAQTLAMNVTNFWKEDAMKTKTHYRAMQADCLQKLQRYLKSGVAIRRTVPPMVNVTCSEVSEGNITVTCRASSFYPRNITLTWRQDGVSLSHNTQQWGDVLPDGNGTYQTWVATRIRQGEEQRFTCYMEHSGNHGTHPVPSGKVLVLQSQRTD |
| SP-ULBP1ed | 92 | MGGVLLTQRTLLSLVLALLFPSMASMGWVDTHCLCYDFIITPKSRPEPQWCEVQGLVDERPFLHYDCVNHKAKAFASLGKKVNVTKTWEEQTETLRDVVDFLKGQLLDIQVENLIPIEPLTLQARMSCEHEAHGHGRGSWQFLFNGQKFLLFDSNNRKWTALHPGAKKMTEKWEKNRDVTMFFQKISLGDCKMWLEEFLMYWEQMLDPT |
| SP-ULBP2ed | 93 | MGGVLLTQRTLLSLVLALLFPSMASMGRADPHSLCYDITVIPKFRPGPRWCAVQGQVDEKTFLHYDCGNKTVTPVSPLGKKLNVTTAWKAQNPVLREVVDILTEQLRDIQLENYTPKEPLTLQARMSCEQKAEGHSSGSWQFSFDGQIFLLFDSEKRMWTTVHPGARKMKEKWENDKVVAMSFHYFSMGDCIGWLEDFLMGMDSTLEPSAG |
| SP-ULBP3ed | 94 | MGGVLLTQRTLLSLVLALLFPSMASMDAHSLWYNFTIIHLPRHGQQWCEVQSQVDQKNFLSYDCGSDKVLSMGHLEEQLYATDAWGKQLEMLREVGQRLRLELADTELEDFTPSGPLTLQVRMSCECEADGYIRGSWQFSFDGRKFLLFDSNNRKWTWVHAGARRMKEKWEKDSGLTTFFKMVSMRDCKSWLRDFLMHRKKRLEPT |
| SP-N2DL4ed | 95 | MGGVLLTQRTLLSLVLALLFPSMASMHSLCFNFTIKSLSRPGQPWCEAQVFLNKNLFLQYNSDNNMVKPLGLLGKKVYATSTWGELTQTLGEVGRDLRMLLCDIKPQIKTSDPSTLQVEMFCQREAERCTGASWQFATNGEKSLLFDAMNMTWTVINHEASKIKETWKKDRGLEKYFRKLSKGDCDHWLREFLGHWEAMPEPTVSPVNASDIHWSSSSLPD |
| SP-RET1Ged | 96 | MGGVLLTQRTLLSLVLALLFPSMASMGLADPHSLCYDITVIPKFRPGPRWCAVQGQVDEKTFLHYDCGSKTVTPVSPLGKKLNVTTAWKAQNPVLREVVDILTEQLLDIQLENYIPKEPLTLQARMSCEQKAEGHSGSWQLSFDGQIFLLFDSENRMWTTVHPGARKMKEKWENDKDMTMSFHYISMGDCTGWLEDFLMGMDSTLEPSAGAPPTMSSGTAQPR |
| SP-RAETILed | 97 | MGGVLLTQRTLLSLVLALLFPSMASMRRDDPHSLCYDITVIPKFRPGPRWCAVQGQVDEKTFLHYDCGNKTVTPVSPLGKKLNVTMAWKAQNPVLREVVDILTEQLLDIQLENYTPKEPLTLQARMSCEQKAEGHSSGSWQFSIDGQTFLLFDSEKRMWTTVHPGARKMKEKWENDKDVAMSFHYISMGDCIGWLEDFLMGMDSTLEPSAG |

Cytotoxicity mediated by NK cells was determined by a CFSE labeling assay. Target cells were labeled with CFSE, washed in PBS, mixed with NK cells at various E:T cell ratios and incubated for 4 h at 37° C. Cells are then analysed by flow cytometry and percentages of CFSE positive engineered T cells are measured, indicating the survival of engineered T cells in the presence of NK cells. It is intended that although NK mediated cell lysis is observed in the positive control (beta2-m deficient engineered T cells), no or limited NK mediated cell lysis is observed when beta2-m deficient engineered T cells engineered T cells express B2M-UL18 (SEQ ID No 89) or secreted NKG2D ligands (SP-MICAed (SEQ ID No 90), SP-MICBed (SEQ ID No 91), SP-ULBP1ed (SEQ ID No 92), SP-ULBP2ed (SEQ ID No 93), SP-ULBP3ed (SEQ ID No 94), SP-N2DL4ed (SEQ ID No 95), SP-RET1Ged (SEQ ID No 96), SP-RAETILed (SEQ ID No 97). The results from this experiment aim to show that allogenic NK cells cytotoxicity activity is impaired when chimeric molecules, express in engineered T cells, act as decoy either for inhibitory signal receptor (B2M-UL18) or for stimulatory signal receptor (NKG2D ligands).

LIST OF REFERENCES CITED IN THE DESCRIPTION

Ashwell, J. D. and R. D. Klusner (1990). "Genetic and mutational analysis of the T-cell antigen receptor." *Annu Rev Immunol* 8: 139-67.

Betts, M. R., J. M. Brenchley, et al. (2003). "Sensitive and viable identification of antigen-specific CD8+ T cells by a flow cytometric assay for degranulation." *J Immunol Methods* 281(1-2): 65-78.

Bierer B. E. et al. (1993) "Cyclosporin A and FK506: molecular mechanisms of immunosuppression and probes for transplantation biology." *Curr Opin Immunol* 5(5): 763-73.

Bix M. et al (1991). "Rejection of class I MHC-deficient haemopoietic cells by irradiated MHC-matched mice." *Nature* 349(6307):329-31.

Boch, J., H. Scholze, et al. (2009). "Breaking the code of DNA binding specificity of TAL-type III effectors." *Science* 326(5959): 1509-12.

Cambier, J. C. (1995). "Antigen and Fc receptor signaling. The awesome power of the immunoreceptor tyrosine-based activation motif (ITAM)." *J Immunol* 155(7): 3281-5.

Carter L, et al. (2002). "PD-1:PD-L inhibitory pathway affects both CD4(+) and CD8(+) T cells and is overcome by IL-2". *Eur. J. Immunol.* 32 (3): 634-43.

Cong, L., F. A. Ran, et al. (2013). "Multiplex genome engineering using CRISPR/Cas systems." *Science* 339 (6121): 819-23.

Critchlow, S. E. and S. P. Jackson (1998). "DNA end-joining: from yeast to man." *Trends Biochem Sci* 23(10): 394-8.

Deltcheva, E., K. Chylinski, et al. (2011). "CRISPR RNA maturation by trans-encoded small RNA and host factor RNase III." *Nature* 471(7340): 602-7.

Gasiunas, G. et al. (2012). "Cas9-crRNA ribonucleoprotein complex mediates specific DNA cleavage for adaptive immunity in bacteria." *Proc Natl Acad Sci USA* 109(39): E2579-86.

Haseloff and Gerlach (1988). "Simple RNA enzymes with new and highly specific endoribonuclease activities." *Nature* 334: 585-591.

Jena, B., G. Dotti, et al. (2010). "Redirecting T-cell specificity by introducing a tumor-specific chimeric antigen receptor." *Blood* 116(7): 1035-44.

Jinek, M., K. Chylinski, et al. (2012). "A programmable dual-RNA-guided DNA endonuclease in adaptive bacterial immunity." *Science* 337(6096): 816-21.

Liu L. et al. (1991). "Calcineurin is a common target of cyclophilin-cyclosporin A and FKBP-FK506 complexes." *Cell* 66(4): 807-15.

Ma, J. L., E. M. Kim, et al. (2003). "Yeast Mre11 and Rad1 proteins define a Ku-independent mechanism to repair double-strand breaks lacking overlapping end sequences." *Mol Cell Biol* 23(23): 8820-8.

Mach B., Steimle V, Reith W (1994). "MHC class II-deficient combined immunodeficiency: a disease of gene regulation". *Immunol. Rev.* 138 (1): 207-21.

Mali, P., L. Yang, et al. (2013). "RNA-guided human genome engineering via Cas9." *Science* 339(6121): 823-6.

Moscou, M. J. and A. J. Bogdanove (2009). "A simple cipher governs DNA recognition by TAL effectors." *Science* 326(5959): 1501.

Park, T. S., S. A. Rosenberg, et al. (2011). "Treating cancer with genetically engineered T cells." *Trends Biotechnol* 29(11): 550-7.

Stoddard, B. L. (2005). "Homing endonuclease structure and function." *Q Rev Biophys* 38(1): 49-95.

Urnov F. D. et al. (2010) "Genome editing with engineered zinc finger nucleases" *Nature reviews Genetics* 11:636-646

We claim:

1. A method for preparing engineered human T-cells expressing a Chimeric Antigen Receptor (CAR) that have lost surface expression of HLA-A, HLA-B, and HLA-C comprising:
   a) providing a population of human T-cells comprising a CAR;
   b) introducing into said human T-cells a rare-cutting endonuclease able to selectively inactivate the gene encoding B2M,
   wherein said rare-cutting endonuclease is a TALE-nuclease encoded by a polynucleotide having at least 90% identity with SEQ ID NO:81, SEQ ID NO:82, SEQ ID NO:84, SEQ ID NO:85, SEQ ID NO:87, or SEQ ID NO:88; and
   c) cleaving the B2M gene with said rare-cutting endonuclease in said human T-cells to induce loss of surface expression of B2M, HLA-A, HLA-B, and HLA-C.

2. A method for preparing engineered human T-cells expressing a Chimeric Antigen Receptor (CAR) that have lost surface expression of HLA-A, HLA-B, and HLA-C comprising:
   a) providing a population of primary human T-cells;
   b) introducing into said human T-cells a rare-cutting endonuclease able to selectively inactivate the gene encoding B2M,
   wherein said rare-cutting endonuclease is a TALE-nuclease encoded by a polynucleotide having at least 90% identity with SEQ ID NO:81, SEQ ID NO:82, SEQ ID NO:84, SEQ ID NO:85, SEQ ID NO:87, or SEQ ID NO:88;
   c) cleaving the B2M gene with said rare-cutting endonuclease in said human T-cells to induce loss of surface expression of B2M, HLA-A, HLA-B, and HLA-C; and
   d) introducing a CAR into the human T-cells that have lost surface expression of B2M, HLA-A, HLA-B, and HLA-C.

3. The method of claim 1, wherein the gene encoding B2M is inactivated in the T cells by cleavage of the gene encoding B2M with a TALE-nuclease (TALEN) that cleaves a target site selected from SEQ ID NO:80, SEQ ID NO:83, and SEQ ID NO:86.

4. The method of claim 2, wherein the gene encoding B2M is inactivated in the T cells by cleavage of the gene encoding B2M with a TALE-nuclease (TALEN) that cleaves a target site selected from SEQ ID NO:80, SEQ ID NO:83, and SEQ ID NO:86.

5. The method of claim 1, wherein said TALEN is encoded by a nucleotide sequences comprising SEQ ID NO:81 or SEQ ID NO:82.

6. The method of claim 2, wherein said TALEN is encoded by a nucleotide sequences comprising SEQ ID NO:81 or SEQ ID NO:82.

7. The method of claim 1, further comprising generating a population of engineered T-cells in which at least 37% of engineered human T-cells that have lost surface expression of HLA-A, HLA-B, and HLA-C.

8. The method of claim 2, further comprising generating a population of engineered T-cells in which at least 37% of engineered human T-cells that have lost surface expression of HLA-A, HLA-B, and HLA-C.

9. The method of claim 1, wherein said Chimeric Antigen Receptor is directed against the B-lymphocyte antigen CD19.

10. The method of claim 2, wherein said Chimeric Antigen Receptor is directed against the B-lymphocyte antigen CD19.

11. The method of claim 7, further comprising administering said population of engineered T-cells to a human patient.

12. The method of claim 8, further comprising administering said population of engineered T-cells to a human patient.

* * * * *

SEQUENCE LISTING

```
Sequence total quantity: 97
SEQ ID NO: 1            moltype = AA  length = 119
FEATURE                 Location/Qualifiers
source                  1..119
                        mol_type = protein
                        organism = Homo sapiens
SEQUENCE: 1
MSRSVALAVL ALLSLSGLEA IQRTPKIQVY SRHPAENGKS NFLNCYVSGF HPSDIEVDLL   60
KNGERIEKVE HSDLSFSKDW SFYLLYYTEF TPTEKDEYAC RVNHVTLSQP KIVKWDRDM   119

SEQ ID NO: 2            moltype = DNA  length = 6673
FEATURE                 Location/Qualifiers
source                  1..6673
                        mol_type = unassigned DNA
                        organism = Homo sapiens
SEQUENCE: 2
aatataagtg gaggcgtcgc gctggcgggc attcctgaag ctgacagcat tcgggccgag   60
```

```
atgtctcgct ccgtggcctt agctgtgctc gcgctactct ctctttctgg cctggaggct    120
atccagcgtg agtctctcct accctcccgc tctggtcctt cctctcccgc tctgcaccct    180
ctgtggccct cgctgtgctc tctcgctccg tgacttccct tctccaagtt ctccttggtg    240
gcccgccgtg gggctagtcc agggctggat ctcggggaag cggcggggtg gcctgggagt    300
ggggaagggg gtgcgcaccc gggacgcgcg ctacttgccc ctttcggcgg ggagcagggg    360
agacctttgg cctacggcga cgggagggtc gggacaaagt ttagggcgtc gataagcgtc    420
agagcgccga ggttggggga gggtttctct tccgctcttt cgcggggcct ctggctcccc    480
cagcgcagct ggagtggggg acgggtaggc tcgtcccaaa ggcgcggcgc tgaggtttgt    540
gaacgcgtgg aggggcgctt ggggtctggg ggaggcgtcg cccgggtaag cctgtctgct    600
gcggctctgc ttcccttaga ctggagagct gtggacttcg tctaggcgcc cgctaagttc    660
gcatgtccta gcacctctgg gtctatgtgg ggccacaccg tggggaggaa acagcacgcg    720
acgtttgtag aatgcttggc tgtgatacaa agcggtttcg aataattaac ttatttgttc    780
ccatcacatg tcactttaaa aaaattataa gaactacccg ttattgacat ctttctgtgt    840
gccaaggact ttatgtgctt tgcgtcattt aattttgaaa acagttatct tccgccatag    900
ataactacta tggttatctt ctgcctctca cagatgaaga aactaaggca ccgagattt     960
aagaaactta attacacagg ggataaatgg cagcaatcga gattgaagtc aagcctaacc   1020
agggcttttg cgggagcgca tgccttttgg ctgtaattcg tgcatttttt tttaagaaaa   1080
acgcctgcct tctgcgtgag attctccaga gcaaactggg cggcatgggc cctgtggtct   1140
tttcgtacag agggcttcct cttttggctct ttgcctggtt gtttccaaga tgtactgtgc   1200
ctcttacttt cggttttgaa aacatgaggg ggttgggcgt ggtagcttac gcctgtaatc   1260
ccagcactta gggaggccga ggcgggagga tggcttgagg tccgtagttg agaccagcct   1320
ggccaacatg gtgaagcctg gtctctacaa aaaataataa caaaaattag ccgggtgtgg   1380
tggctcgtgc ctgtggtccc agctgctccg gtgtgctgagg cgggaggatc tcttgagctt   1440
aggcttttga gctatcatgg cgccagtgca ctccagcgtg ggcaacagag cgagaccctg   1500
tctctcaaaa aagaaaaaaa aaaaaaaga aagagaaaag aaaagaaaga aagaagtgaa   1560
ggtttgtcag tcaggggagc tgtaaaacca ttaataaaga taatccaaga tggttaccaa   1620
gactgttgag gacgccagag atcttgagca ctttctaagt acctggcaat acactaagcg   1680
cgctcacctt ttcctctggc aaaacatgat cgaaagcaga atgttttgat catgagaaaa   1740
ttgcatttaa tttgaataca atttatttac aacataaagg ataatgtata tatcaccacc   1800
attactggta tttgctggtt atgttagatg tcattttaaa aaataacaat ctgatattta   1860
aaaaaaaatc ttattttgaa aatttccaaa gtaatacatg ccatgcatag accatttctg   1920
gaagatacca caagaaacat gtaatgatga ttgcctctga aggtctattt tcctcctctg   1980
acctgtgtgt gggttttgtt tttgttttac tgtgggcata aattaatttt tcagttaagt   2040
tttggaagct taaataactc tccaaaagtc ataaagccag taactggttg agcccaaatt   2100
caaacccagc ctgtctgata cttgtcctct tcttagaaaa gattacagtg atgctctcac   2160
aaaatcttgc cgccttccct caaacagaga gttccaggca ggatgaatct gtgctctgat   2220
ccctgaggca tttaatatgt tcttattatt agaagctcag atgcaaagag ctctcttagc   2280
ttttaatgtt atgaaaaaaa tcaggtcttc attagattcc ccaatccacc tcttgatggg   2340
gctagtagcc tttccttaat gataggtgt ttctagagag atatatctgg tcaaggtggt   2400
ctggtactcc tccttctccc cacagcctcc cagacaagga ggagtagctc cctttagtg   2460
atcatgtacc ctgaatataa gtgtatttaa aagaatttta tacacatata tttagtgtca   2520
atctgtatat ttagtagcac taacacttct cttcatttc aatgaaaaat atagagttta   2580
taatattttc ttcccacttc cccatggatg gtctagtcat ggcctctcatt ttggaaagta   2640
ctgtttctga aacattaggc aatatattcc caacctggct agtttacagc aatcacctgt   2700
ggatgctaat taaaacgcaa atcccactgt cacatgcatt actccatttg atcataatgg   2760
aaagtatgtt ctgtcccatt tgccatagtc ctcacctatc cctgttgtat tttatcgggt   2820
ccaactcaac catttaaggt atttgccagc tcttgtatgc atttaggttt tgtttctttg   2880
tttttttagct catgaaatta ggtacaaagt cagagagggg tctggcatat aaaacctcag   2940
cagaaataaa gaggttttgt tgtttggtaa gaacatacct tgggttggtt gggcacggtg   3000
gctcgtgcct gtaatcccaa cactttggga ggccaaggca ggctgatcac ttgaagttgg   3060
gagttcaaga ccagcctggc caacatggtg aaatcccgtc tctactgaaa atacaaaaat   3120
taaccaggca tggtggtgtg tgcctgtagt cccaggaatc acttgaaccc aggaggcgga   3180
ggttgcagtg agctgagatc tcaccactgc acactgcact ccagcctggg caatggaatg   3240
agattccatc ccaaaaaata aaaaaataaa aaataaaga acataccttg ggttgatcca   3300
cttaggaacc tcagataata acatctgcca cgtatagacc aattgctatg tcccaggcac   3360
tctactagac acttcataca gtttagaaaa tcagatgggt gtagatcaag gcaggagcag   3420
gaaccaaaaa gaaaggcata aacataagaa aaaaatgga aggggtggaa acagagtaca   3480
ataacatgag taatttgatg ggggctatta tgaactgaga aatgaacttt gaaaagtatc   3540
ttggggccaa atcatgtaga ctcttgagtg atgtgttaag gaatgctatg agtgctgaga   3600
gggcatcaga agtccttgag agcctccaga gaaaggctct taaaaatgca gcgcaatctc   3660
cagtgacaga agatactgct agaaatctgc tagaaaaaaa acaaaaaagg catgtataga   3720
ggaattatga gggaaagata ccaagtcacg gtttattctt caaaatggag gtggcttgtt   3780
gggaaggtgg aagctcattt ggccagagtg gaaatgaat tgggagaaat cgatgaccaa   3840
atgtaaacac ttggtgcctg atatagcttg acaccaagtt agcccaagt gaaatacctt   3900
ggcaatatta atgtgtcttt tcccgatatt cctcaggtac tccaaagatt caggtttact   3960
cacgtcatcc agcagagaat ggaaagtcaa atttcctgaa ttgctatgtg tctgggttc   4020
atccatccga cattgaagtt gacttactga agaatggaga gagaattgaa aaagtggagc   4080
attcagactt gtctttcagc aaggactggt cttttctatct cttgtactac actgaattca   4140
cccccactga aaaagatgag tatgcctgcc gtgtgaacca tgtgactttg tcacagccca   4200
agatagttaa gtgggtaag tcttacattc ttttgtaagc tgctgaaagt tgtgtatgag   4260
tagtcatatc ataaagctgc tttgatataa aaaaggtcta tggccatact accctgaatg   4320
agtcccatcc catctgatat aaacaatctg catattggga ttgtcaggga atgttcttaa   4380
agatcagatt agtggcacct gctgagatac tgatgcacac catggtttct gaaccagtag   4440
tttcccttgca gttgagcagg gagcagcagc agcacttgca caaatacata tacactctta   4500
acacttctta cctactggct tcctctagct tttgtggcag cttcaggtat atttagcact   4560
gaacgaacat ctcaagaagg tataggcctt gtttgtaagt cctgctgtc ctagcatcct   4620
ataatcctgg acttctccag tactttctgg ctggattggt atctgaggct agtaggaagg   4680
gcttgttcct gctgggtagc tctaaacaat gtattcatgg gtaggaacag cagcctattc   4740
tgccagcctt atttctaacc attttagaca tttgttagta catggtattt taaaagtaaa   4800
```

```
acttaatgtc ttcctttttt ttctccactg tcttttcat agatcgagac atgtaagcag    4860
catcatggag gtaagttttt gaccttgaga aaatgttttt gtttcactgt cctgaggact    4920
attttatagac agctctaaca tgataacccct cactatgtgg agaacattga cagagtaaca   4980
ttttagcagg gaaagaagaa tcctacaggg tcatgttccc ttctcctgtg gagtggcatg    5040
aagaaggtgt atggcccag gtatggccat attactgacc ctctacagag agggcaaagg    5100
aactgccagt atggtattgc aggataaagg caggtggtta cccacattac ctgcaaggct    5160
ttgatctttc ttctgccatt tccacattgg acatctctgc tgaggagaga aaatgaacca    5220
ctcttttcct ttgtataatg ttgttttatt cttcagacag aagagaggag ttatacagct    5280
ctgcagacat cccattcctg tatggggact gtgtttgcct cttagaggtt cccaggccac    5340
tagaggagat aaagggaaac agattgttat aacttgatat aatgatacta taatagatgt    5400
aactacaagg agctccagaa gcaagagaga gggaggaact tggacttctc tgcatcttta    5460
gttggagtcc aaaggctttt caatgaaatt ctactgccca gggtacattg atgctgaaac    5520
cccattcaaa tctcctgtta tattctagaa cagggaattg atttgggaga gcatcaggaa    5580
ggtggatgat ctgcccagtc acactgttag taaattgtag agccaggacc tgaactctaa    5640
tatagtcatg tgttacttaa tgacgggac atgttctgag aaatgcttac acaaacctag    5700
gtgttgtagc ctactacacg cataggctac atggtatagc ctattgctcc tagactacaa    5760
acctgtacag cctgttactg tactgaatac tgtgggcagt gtaacacaa tggtaagtat    5820
ttgtgtatct aaacatagaa gttgcagtaa aaatatgcta ttttaatctt atgagaccac    5880
tgtcatatat acagtccatc attgaccaaa acatcatatc agcatttttt cttctaagat    5940
tttgggagca ccaaagggat acactaacag gatatactct ttataatggg tttggagaac    6000
tgtctgcagc tacttctttt aaaaaggtga tctacacagt agaaattaga caagtttggt    6060
aatgatctc gcaatccaaa taaaataaat tcattgctaa ccttttctt ttcttttcag      6120
gtttgaagat gccgcatttg gattggatga attccaaatt ctgcttgctt gcttttaaat    6180
attgatatgc ttatacactt acactttatg cacaaaatgt agggttataa taatgttaac    6240
atggacatga tcttctttat aattctactt tgagtgctgt ctccatgttt gatgtatctg    6300
agcaggttgc tccacaggta gctctaggag ggctgcggtcaa ttagaggtgg ggagcagaga   6360
attctcttat ccaacatcaa catcttggtc agatttgaac tcttcaatct cttgcactca    6420
aagcttgtta agatagttaa gcgtgcataa gttaacttcc aatttacata ctctgcttag    6480
aatttgggggg aaaattaga aatataattg acaggattat tggaaatttg ttataatgaa    6540
tgaaacattt tgtcatataa gattcatatt tacttcttat acatttgata agtaaggca    6600
tggttgtgtg taatctggtt tattttgtt ccacaagtta aataaatcat aaaacttgat     6660
gtgttatctc tta                                                      6673

SEQ ID NO: 3        moltype = DNA  length = 987
FEATURE             Location/Qualifiers
source              1..987
                    mol_type = unassigned DNA
                    organism = Homo sapiens
SEQUENCE: 3
aatataagtg gaggcgtcgc gctggcgggc attcctgaag ctgacagcat tcgggccgag    60
atgtctcgct ccgtggcctt agctgtgctc gcgctactct ctctttctgg cctgaggct    120
atccagcgta ctccaaagat tcaggtttac tcacgtcatc cagcagagaa tggaaagtca    180
aatttcctga attgctatgt gtctgggttt catccatccg acattgaagt tgacttactg    240
aagaatggag agagaattga aaagtggag cattcagact tgtctttcag caaggactgg    300
tctttctatc tcttgtacta cactgaattc accccccactg aaaagaatga gtatgcctgc    360
cgtgtgaacc atgtgacttt gtcacagccc aagatagtta agtgggatcg agacatgaa    420
gcagcatcat ggaggtttga agatgccgca tttggattgg atgaattcca aattctgctt    480
gcttgctttt taatattgat atgcttatac acttacactt tatgcacaaa atgtagggt    540
ataataatgt taacatggac atgatcttct ttataattct actttgagtg ctgtctccat    600
gtttgatgta tctgagcagg ttgctccaca ggtagctcta ggagggctgg caacttagag    660
gtggggagca gagaattctc tatccaaca tcaacatctt ggtcagattt gaactcttca    720
atctcttgca ctcaaagctt gttaagatag ttaagcgtgc ataagttaac ttccaattta    780
catactctgc ttagaatttg ggggaaaatt tagaaatata attgacagga ttattggaaa    840
tttgttataa tgaatgaaac attttgtcat ataagattca tatttacttc ttatacattt    900
gataaagtaa ggcatggttg tggttaatct ggtttatttt tgttccacaa gttaaataaa    960
tcataaaact tgatgtgtta tctctta                                       987

SEQ ID NO: 4        moltype = AA   length = 1130
FEATURE             Location/Qualifiers
source              1..1130
                    mol_type = protein
                    organism = Homo sapiens
SEQUENCE: 4
MRCLAPRPAG SYLSEPQGSS QCATMELGPL EGGYLELLNS DADPLCLYHF YDQMDLAGEE    60
EIELYSEPDT DTINCDQFSR LLCDMEGDEE TREAYANIAE LDQYVFQDSQ LEGLSKDIFK    120
HIGPDEVIGE SMEMPAEVGQ KSQKRPFPEE LPADLKHWKP AEPPTVVTGS LLVGPVSDCS    180
TLPCLPLPAL FNQEPASGQM RLEKTDQIPM PFSSSSLSCL NLPEGPIQFV PTISTLPHGL    240
WQISEAGTGV SSIFIYHGEV PQASQVPPPS GFTVHGLPTS PDRPGSTSPF APSATDLPSM    300
PEPALTSRAN MTEHKTSPTQ CPAAGEVSNK LPKWPEPVEQ FYRSLQDTYG AEPAGPDGIL    360
VEVDLVQARL ERSSSKSLER ELATPDWAER QLAQGGLAEV LLAAKEHRRP RETRVIAVLG    420
KAGQGKSYWA GAVSRAWACG RLPQYDFVFS VPCHCLNRPG DAYGLQDLLF SLGPQPLVAA    480
DEVFSHILKR PDRVLLILDG FEELEAQDGF LHSTCGPAPA EPCSLRGLLA GLFQKKLLRG    540
CTLLLTARPR GRLVQSLSKA DALFELSGFS MEQAQAYVMR YFESSGMTEH QDRALTLLRD    600
RPLLLSHSHS PTLCRAVCQL SEALLELGED AKLPSTLTGL YVGLLGRAAL DSPPGALAEL    660
AKLAWELGRR HQSTLQEDQF PSADVRTWAM AKGLVQHPPR AAESELAFPS FLLQCFLGAL    720
WLALSGEIKD KELPQYLALT PRKKRPYDNW LEGVPRFLAG LIFQPPARCL GALLGPSAAA    780
SVDRKQKVLA RYLKRLQPGT LRARQLLELL HCAHEAEEAG IWQHVVQELP GRLSFLGTRL    840
TPPDAHVLGK ALEAAGQDFS LDLRSTGICP SGLGSLVGLS CVTRFRAALS DTVALWESLQ    900
QHGETKLLQA AEEKFTIEPF KAKSLKDVED LGKLVQTQRL RSSSEDTAGE LPAVRDLKKL    960
```

```
EFALGPVSGP QAFPKLVRIL TAFSSLQHLD LDALSENKIG DEGVSQLSAT FPQLKSLETL    1020
NLSQNNITDL GAYKLAEALP SLAASLLRLS LYNNCICDVG AESLARVLPD MVSLRVMDVQ    1080
YNKFTAAGAQ QLAASLRRCP HVETLAMWTP TIPFSVQEHL QQQDSRISLR              1130

SEQ ID NO: 5           moltype = DNA  length = 4654
FEATURE                Location/Qualifiers
source                 1..4654
                       mol_type = unassigned DNA
                       organism = Homo sapiens
SEQUENCE: 5
ggttagtgat gaggctagtg atgaggctgt gtgcttctga gctgggcatc cgaaggcatc     60
cttggggaag ctgagggcac gaggaggggc tgccagactc cgggagctgc tgcctggctg    120
ggattcctac acaatgcgtt gcctggctcc acgccctgct gggtcctacc tgtcagagcc    180
ccaaggcagc tcacagtgtg ccaccatgga gttgggggcc ctagaaggtg gctacctgga    240
gcttcttaac agcgatgctg accccctgtg cctctaccac ttctatgacc agatggacct    300
ggctggagaa gaagagattg agctctactc agaacccgac acagacacca tcaactgcga    360
ccagttcagc aggctgttgt gtgacatgga aggtgatgaa gagaccaggg aggcttatgc    420
caatatcgcg gaactggacc agtatgtctt ccaggactcc cagctggagg gcctgagcaa    480
ggacattttc aagcacatag gaccagatga agtgatcggt gagagtatgg agatgccagc    540
agaagttggg cagaaaagtc agaaaagacc cttcccagag gagcttccgg cagacctgaa    600
gcactggaag ccagctgagc cccccactgt ggtgactggc agtctcctag tgggaccagt    660
gagcgactgc tccaccctgc cctgcctgcc actgcctgcc ctgttcaacc aggagccagc    720
ctccggccag atgcgcctgg agaaaaccga ccagattccc atgccttcct ccagttcctg    780
gttgagctgc ctgaatctcc ctgagggacc catccagttt gtcccaccca tctccactct    840
gccccatggg ctctggcaaa tctctgaggc tggaacaggg gtctccagta tattcatcta    900
ccatgggag gtgccccagg ccagccaagt acccccctcc agtggattca ctgtccacgg    960
cctcccaaca tctccagacc ggccaggctc caccagcccc ttcgctccat cagccactga   1020
cctgccagc atgcctgaac ctgccctgac ctcccgagca aacatgacag agcacaagac   1080
gtcccccacc caatgcccgg cagctggaga ggtctccaac aagcttccaa aatggcctga   1140
gccggtggag cagttctacc gctcactgca ggacacgtat ggtgccgagc ccgcaggccc   1200
ggatggcatc ctagtggagg tggatctggt gcaggccagg ctggagagga gcagcagcaa   1260
gagcctggag cgggaactgg ccaccccgga ctgggcagaa cggcagctgg cccaaggagg   1320
cctggctgag gtgctgttgg ctgccaagga gcaccggcgg ccgcgtgaga cacgagtgat   1380
tgctgtgctg ggcaaagctg gtcagggcaa gagctattgg gctggggcag tgagccgggc   1440
ctgggcttgt ggccggcttc ccagtacga cttttgtcttc tctgtcccct gccattgctt   1500
gaaccgtccg ggggatgcct atggcctgca ggatctgctc ttctccctgg cccacagcc    1560
actcgtggcg gccgatgagg ttttcagcca catcttgaag agacctgacc gcgttctgct   1620
catcctagac ggcttcgagg agctggaagc gcaagatggc ttcctgcaca gcacgtgcgg   1680
accggcaccg gcggagccct gctccctccg ggggctgctg gccggccttt tccagaagaa   1740
gctgctccga ggttgcaccc tcctcctcac agcccggccc cggggccgcc tggtccagag   1800
cctgagcaag gccgacgccc tatttgagct gtccggcttc tccatggagc aggcccaggc   1860
atacgtgatg cgctactttg agagctcagg gatgacagag caccaagaca gagccctgac   1920
gctcctccgg gaccggccac ttcttctcag tcacagccac agccctactt tgtgccgggc   1980
agtgtgccag ctctcagagg ccctgctgga gcttggggag gacgccaagc tgccctccac   2040
gctcacggga ctctatgtcg gcctgctggg ccgtgcagcc ctcgacagcc cccccggggc   2100
cctggcagag ctggccaagc tggcctggga gctgggccgc agacatcaaa gtaccctaca   2160
ggaggaccag ttccatccg cagacgtgag gacctgggca atgccaaag gcttagtcca     2220
acacccaccg cgggccgcag agtccgagct ggccttcccc agcttcctcc tgcaatgctt   2280
cctgggggcc ctgtgctgg ctctgagtgg cgaaatcaag gacaaggagc tcccgcagta    2340
cctagcattg accccaagga agaagaggcc ctatgacaac tggctggagg gcgtgccacg   2400
ctttctggct gggctgatct tccagcctcc cgcccgctgc ctgggagccc tactcgggcc   2460
atcggcggct gcctcggtgg acaggaagca gaaggtgctt gcgaggtacc tgaagcggct   2520
gcagccgggg acactgcggg cgcggcagct gctggagctg ctgcactgcg cccacgaggc   2580
cgaggaggct ggaatttggc agcacgtggt acaggagctc cccggccgcc tctcttttct   2640
gggcacccgc ctcacgcctc ctgatgcaca tgtactgagc aaggccttgg aggcggcggg   2700
ccaagacttc tccctggacc tccgcagcac tggcatttgc ccctctggat tggggagcct   2760
cgtgggactc agctgtgtca cccgtttcag ggctgccttg agcacacgg tggcgctgtg    2820
ggagtccctg cagcagcatg gggagaccaa gctacttcag gcagcagagg agaagttcac   2880
catcgagcct ttcaaagcca gtccctgaa ggatgtggaa gacctgggaa agcttgtgca    2940
gactcagagg acgagaagtt cctcggaaga cacgctggg gagctccctg ctgttcggga    3000
cctaaagaaa ctggagtttg cgctgggccc tgtctcaggc cccaggcttt ccccaaact    3060
ggtgcggatc ctcacggcct ttcctcct gcagcatctg gacctggatg cgctgagtga     3120
gaacaagatc ggggacgagg tgtgtctcga gctctcagcc accttccccc agctgaagtc   3180
cttggaaacc ctcaatctgt cccagaacaa tatcactgac ctggtgccta acaaactcgc   3240
cgaggccctg ccttcgctcg ctgcatccct gctcaggcta agcttgtaca ataactgcat   3300
ctgcgacgtg ggagccgaga gcttggctcg tgtgcttccg gacatggtgt ccctccgggt   3360
gatggacgtc cagtacaaca gttcacggc tgccggggcc cagcagctcg ctgccagcct    3420
tcggaggtgt cctcatgtgg agacgttggc gatgtggacg cccaccatgc cattcagtgt   3480
ccaggaacac ctgcaacaac aggattcacg gatcagcctg agatgatccc agctgtgctc   3540
tggacaggca tgttctctga ggacactaac cacgctggac cttaactgg gtacttgtgg    3600
acacagctct tctccaggct gtatcccatg agcctcagca cctggcacc cggccctgc     3660
tggttcaggt ttgccctg cccggctgcg gaatgaacca catcttgctc tgctgacaga     3720
cacaggcccg gctccaggct cctttagcgc ccagttgggg ggatgcctgg tggcagctgc   3780
ggtccaccca ggaggccga ggcctcctct gaaggacatt gggacagcc acggccaggc    3840
cagagggagt gacagaggca gcccattct gcctgcccag gcccctgcca ccctgggga    3900
aaagtacttc tttttttta ttttagaca gagtctcact gttgcccagg ctggcgtgca    3960
gtggtgcgat ctgggttcac tgcaacctcc gcctcttggg ttcaagcgat tcttctgctt   4020
cagcctcccg agtagctggg actacaggca cccaccatca tgtctggcta attttcatt   4080
ttagtagag acagggtttt gccatgttgg ccaggctggt ctcaaactct tgacctcagg   4140
```

```
tgatccaccc acctcagcct cccaaagtgc tgggattaca agcgtgagcc actgcaccgg    4200
gccacagaga aagtacttct ccaccctgct ctccgaccag acaccttgac agggcacacc    4260
gggcactcag aagacactga tgggcaaccc ccagcctgct aattcccag attgcaacag     4320
gctgggcttc agtggcagct gcttttgtct atgggactca atgcactgac attgttggcc    4380
aaagccaaag ctaggcctgg ccagatgcac cagccctag cagggaaaca gctaatggga     4440
cactaatggg gcggtgagag gggaacagac tggaagcaca gcttcatttc ctgtgtcttt    4500
tttcactaca ttataaatgt ctctttaatg tcacaggcag gtccagggtt tgagttcata    4560
ccctgttacc attttggggt acccactgct ctggttatct aatatgtaac aagccacccc    4620
aaatcatagt ggcttaaaac aacactcaca ttta                                4654

SEQ ID NO: 6             moltype = AA  length = 495
FEATURE                  Location/Qualifiers
REGION                   1..495
                         note = anti-CD19 Cimeric Antigen Receptor
source                   1..495
                         mol_type = protein
                         organism = synthetic construct
SEQUENCE: 6
METDTLLLWV LLLWVPGSTG EVQLQQSGPE LIKPGASVKM SCKASGYTFT SYVMHWVKQK      60
PGQGLEWIGY INPYNDGTKY NEKFKGKATL TSDKSSSTAY MELSSLTSED SAVYYCARGT     120
YYYGSRVFDY WGQGTTLTVS SGGGGSGGGG SGGGGSDIVM TQAAPSIPVT PGESVSISCR     180
SSKSLLNSNG NTYLYWFLQR PGQSPQLLIY RMSNLASGVP DRFSGSGSGT AFTLRISRVE     240
AEDVGVYYCM QHLEYPFTFG AGTKLELKRS DPTTTPAPRP PTPAPTIASQ PLSLRPEACR     300
PAAGGAVHTR GLDFACDIYI WAPLAGTCGV LLLSLVITLY CKRGRKKLLY IFKQPFMRPV     360
QTTQEEDGCS CRFPEEEEGG CELRVKFSRS ADAPAYQQGQ NQLYNELNLG RREEYDVLDK     420
RRGRDPEMGG KPRRKNPQEG LYNELQKDKM AEAYSEIGMK GERRRGKGHD GLYQGLSTAT     480
KDTYDALHMQ ALPPR                                                     495

SEQ ID NO: 7             moltype = AA  length = 17
FEATURE                  Location/Qualifiers
REGION                   1..17
                         note = ANti-CD19 CAR
source                   1..17
                         mol_type = protein
                         organism = synthetic construct
SEQUENCE: 7
AAAAAAAAAA AAAAAAA                                                    17

SEQ ID NO: 8             moltype = DNA  length = 23
FEATURE                  Location/Qualifiers
source                   1..23
                         mol_type = unassigned DNA
                         organism = Homo sapiens
SEQUENCE: 8
gagaatcaaa atcggtgaat agg                                             23

SEQ ID NO: 9             moltype = DNA  length = 23
FEATURE                  Location/Qualifiers
source                   1..23
                         mol_type = unassigned DNA
                         organism = Homo sapiens
SEQUENCE: 9
ttcaaaacct gtcagtgatt ggg                                             23

SEQ ID NO: 10            moltype = DNA  length = 23
FEATURE                  Location/Qualifiers
source                   1..23
                         mol_type = unassigned DNA
                         organism = Homo sapiens
SEQUENCE: 10
tgtgctagac atgaggtcta tgg                                             23

SEQ ID NO: 11            moltype = DNA  length = 23
FEATURE                  Location/Qualifiers
source                   1..23
                         mol_type = unassigned DNA
                         organism = Homo sapiens
SEQUENCE: 11
cgtcatgagc agattaaacc cgg                                             23

SEQ ID NO: 12            moltype = DNA  length = 23
FEATURE                  Location/Qualifiers
source                   1..23
                         mol_type = unassigned DNA
                         organism = Homo sapiens
SEQUENCE: 12
tcagggttct ggatatctgt ggg                                             23

SEQ ID NO: 13            moltype = DNA  length = 23
```

```
FEATURE                 Location/Qualifiers
source                  1..23
                        mol_type = unassigned DNA
                        organism = Homo sapiens
SEQUENCE: 13
gtcagggttc tggatatctg tgg                                               23

SEQ ID NO: 14           moltype = DNA   length = 23
FEATURE                 Location/Qualifiers
source                  1..23
                        mol_type = unassigned DNA
                        organism = Homo sapiens
SEQUENCE: 14
ttcggaaccc aatcactgac agg                                               23

SEQ ID NO: 15           moltype = DNA   length = 23
FEATURE                 Location/Qualifiers
source                  1..23
                        mol_type = unassigned DNA
                        organism = Homo sapiens
SEQUENCE: 15
taaacccggc cactttcagg agg                                               23

SEQ ID NO: 16           moltype = DNA   length = 23
FEATURE                 Location/Qualifiers
source                  1..23
                        mol_type = unassigned DNA
                        organism = Homo sapiens
SEQUENCE: 16
aaagtcagat ttgttgctcc agg                                               23

SEQ ID NO: 17           moltype = DNA   length = 23
FEATURE                 Location/Qualifiers
source                  1..23
                        mol_type = unassigned DNA
                        organism = Homo sapiens
SEQUENCE: 17
aacaaatgtg tcacaaagta agg                                               23

SEQ ID NO: 18           moltype = DNA   length = 23
FEATURE                 Location/Qualifiers
source                  1..23
                        mol_type = unassigned DNA
                        organism = Homo sapiens
SEQUENCE: 18
tggatttaga gtctctcagc tgg                                               23

SEQ ID NO: 19           moltype = DNA   length = 23
FEATURE                 Location/Qualifiers
source                  1..23
                        mol_type = unassigned DNA
                        organism = Homo sapiens
SEQUENCE: 19
taggcagaca gacttgtcac tgg                                               23

SEQ ID NO: 20           moltype = DNA   length = 23
FEATURE                 Location/Qualifiers
source                  1..23
                        mol_type = unassigned DNA
                        organism = Homo sapiens
SEQUENCE: 20
agctggtaca cggcagggtc agg                                               23

SEQ ID NO: 21           moltype = DNA   length = 23
FEATURE                 Location/Qualifiers
source                  1..23
                        mol_type = unassigned DNA
                        organism = Homo sapiens
SEQUENCE: 21
gctggtacac ggcagggtca ggg                                               23

SEQ ID NO: 22           moltype = DNA   length = 23
FEATURE                 Location/Qualifiers
source                  1..23
                        mol_type = unassigned DNA
                        organism = Homo sapiens
SEQUENCE: 22
tctctcagct ggtacacggc agg                                               23
```

-continued

```
SEQ ID NO: 23          moltype = DNA   length = 23
FEATURE                Location/Qualifiers
source                 1..23
                       mol_type = unassigned DNA
                       organism = Homo sapiens
SEQUENCE: 23
tttcaaaacc tgtcagtgat tgg                                              23

SEQ ID NO: 24          moltype = DNA   length = 23
FEATURE                Location/Qualifiers
source                 1..23
                       mol_type = unassigned DNA
                       organism = Homo sapiens
SEQUENCE: 24
gattaaaccc ggccactttc agg                                              23

SEQ ID NO: 25          moltype = DNA   length = 23
FEATURE                Location/Qualifiers
source                 1..23
                       mol_type = unassigned DNA
                       organism = Homo sapiens
SEQUENCE: 25
ctcgaccagc ttgacatcac agg                                              23

SEQ ID NO: 26          moltype = DNA   length = 23
FEATURE                Location/Qualifiers
source                 1..23
                       mol_type = unassigned DNA
                       organism = Homo sapiens
SEQUENCE: 26
agagtctctc agctggtaca cgg                                              23

SEQ ID NO: 27          moltype = DNA   length = 23
FEATURE                Location/Qualifiers
source                 1..23
                       mol_type = unassigned DNA
                       organism = Homo sapiens
SEQUENCE: 27
ctctcagctg gtacacggca ggg                                              23

SEQ ID NO: 28          moltype = DNA   length = 23
FEATURE                Location/Qualifiers
source                 1..23
                       mol_type = unassigned DNA
                       organism = Homo sapiens
SEQUENCE: 28
aagttcctgt gatgtcaagc tgg                                              23

SEQ ID NO: 29          moltype = DNA   length = 23
FEATURE                Location/Qualifiers
source                 1..23
                       mol_type = unassigned DNA
                       organism = Homo sapiens
SEQUENCE: 29
atcctcctcc tgaaagtggc cgg                                              23

SEQ ID NO: 30          moltype = DNA   length = 23
FEATURE                Location/Qualifiers
source                 1..23
                       mol_type = unassigned DNA
                       organism = Homo sapiens
SEQUENCE: 30
tgctcatgac gctgcggctg tgg                                              23

SEQ ID NO: 31          moltype = DNA   length = 23
FEATURE                Location/Qualifiers
source                 1..23
                       mol_type = unassigned DNA
                       organism = Homo sapiens
SEQUENCE: 31
acaaaactgt gctagacatg agg                                              23

SEQ ID NO: 32          moltype = DNA   length = 23
FEATURE                Location/Qualifiers
source                 1..23
                       mol_type = unassigned DNA
                       organism = Homo sapiens
SEQUENCE: 32
atttgtttga gaatcaaaat cgg                                              23
```

```
SEQ ID NO: 33            moltype = DNA   length = 23
FEATURE                  Location/Qualifiers
source                   1..23
                         mol_type = unassigned DNA
                         organism = Homo sapiens
SEQUENCE: 33
catcacagga actttctaaa agg                                              23

SEQ ID NO: 34            moltype = DNA   length = 23
FEATURE                  Location/Qualifiers
source                   1..23
                         mol_type = unassigned DNA
                         organism = Homo sapiens
SEQUENCE: 34
gtcgagaaaa gctttgaaac agg                                              23

SEQ ID NO: 35            moltype = DNA   length = 23
FEATURE                  Location/Qualifiers
source                   1..23
                         mol_type = unassigned DNA
                         organism = Homo sapiens
SEQUENCE: 35
ccactttcag gaggaggatt cgg                                              23

SEQ ID NO: 36            moltype = DNA   length = 23
FEATURE                  Location/Qualifiers
source                   1..23
                         mol_type = unassigned DNA
                         organism = Homo sapiens
SEQUENCE: 36
ctgacaggtt ttgaaagttt agg                                              23

SEQ ID NO: 37            moltype = DNA   length = 23
FEATURE                  Location/Qualifiers
source                   1..23
                         mol_type = unassigned DNA
                         organism = Homo sapiens
SEQUENCE: 37
agctttgaaa caggtaagac agg                                              23

SEQ ID NO: 38            moltype = DNA   length = 23
FEATURE                  Location/Qualifiers
source                   1..23
                         mol_type = unassigned DNA
                         organism = Homo sapiens
SEQUENCE: 38
tggaataatg ctgttgttga agg                                              23

SEQ ID NO: 39            moltype = DNA   length = 23
FEATURE                  Location/Qualifiers
source                   1..23
                         mol_type = unassigned DNA
                         organism = Homo sapiens
SEQUENCE: 39
agagcaacag tgctgtggcc tgg                                              23

SEQ ID NO: 40            moltype = DNA   length = 23
FEATURE                  Location/Qualifiers
source                   1..23
                         mol_type = unassigned DNA
                         organism = Homo sapiens
SEQUENCE: 40
ctgtggtcca gctgaggtga ggg                                              23

SEQ ID NO: 41            moltype = DNA   length = 23
FEATURE                  Location/Qualifiers
source                   1..23
                         mol_type = unassigned DNA
                         organism = Homo sapiens
SEQUENCE: 41
ctgcggctgt ggtccagctg agg                                              23

SEQ ID NO: 42            moltype = DNA   length = 23
FEATURE                  Location/Qualifiers
source                   1..23
                         mol_type = unassigned DNA
                         organism = Homo sapiens
SEQUENCE: 42
```

```
tgtggtccag ctgaggtgag ggg                                              23

SEQ ID NO: 43           moltype = DNA   length = 23
FEATURE                 Location/Qualifiers
source                  1..23
                        mol_type = unassigned DNA
                        organism = Homo sapiens
SEQUENCE: 43
cttcttcccc agcccaggta agg                                              23

SEQ ID NO: 44           moltype = DNA   length = 23
FEATURE                 Location/Qualifiers
source                  1..23
                        mol_type = unassigned DNA
                        organism = Homo sapiens
SEQUENCE: 44
acacggcagg gtcagggttc tgg                                              23

SEQ ID NO: 45           moltype = DNA   length = 23
FEATURE                 Location/Qualifiers
source                  1..23
                        mol_type = unassigned DNA
                        organism = Homo sapiens
SEQUENCE: 45
cttcaagagc aacagtgctg tgg                                              23

SEQ ID NO: 46           moltype = DNA   length = 23
FEATURE                 Location/Qualifiers
source                  1..23
                        mol_type = unassigned DNA
                        organism = Homo sapiens
SEQUENCE: 46
ctggggaaga aggtgtcttc tgg                                              23

SEQ ID NO: 47           moltype = DNA   length = 23
FEATURE                 Location/Qualifiers
source                  1..23
                        mol_type = unassigned DNA
                        organism = Homo sapiens
SEQUENCE: 47
tcctcctcct gaaagtggcc ggg                                              23

SEQ ID NO: 48           moltype = DNA   length = 23
FEATURE                 Location/Qualifiers
source                  1..23
                        mol_type = unassigned DNA
                        organism = Homo sapiens
SEQUENCE: 48
ttaatctgct catgacgctg cgg                                              23

SEQ ID NO: 49           moltype = DNA   length = 23
FEATURE                 Location/Qualifiers
source                  1..23
                        mol_type = unassigned DNA
                        organism = Homo sapiens
SEQUENCE: 49
acccggccac tttcaggagg agg                                              23

SEQ ID NO: 50           moltype = DNA   length = 23
FEATURE                 Location/Qualifiers
source                  1..23
                        mol_type = unassigned DNA
                        organism = Homo sapiens
SEQUENCE: 50
ttcttcccca gcccaggtaa ggg                                              23

SEQ ID NO: 51           moltype = DNA   length = 23
FEATURE                 Location/Qualifiers
source                  1..23
                        mol_type = unassigned DNA
                        organism = Homo sapiens
SEQUENCE: 51
cttacctggg ctggggaaga agg                                              23

SEQ ID NO: 52           moltype = DNA   length = 23
FEATURE                 Location/Qualifiers
source                  1..23
                        mol_type = unassigned DNA
                        organism = Homo sapiens
```

```
SEQUENCE: 52
gacaccttct tccccagccc agg                                           23

SEQ ID NO: 53           moltype = DNA   length = 23
FEATURE                 Location/Qualifiers
source                  1..23
                        mol_type = unassigned DNA
                        organism = Homo sapiens
SEQUENCE: 53
gctgtggtcc agctgaggtg agg                                           23

SEQ ID NO: 54           moltype = DNA   length = 23
FEATURE                 Location/Qualifiers
source                  1..23
                        mol_type = unassigned DNA
                        organism = Homo sapiens
SEQUENCE: 54
ccgaatcctc ctcctgaaag tgg                                           23

SEQ ID NO: 55           moltype = DNA   length = 49
FEATURE                 Location/Qualifiers
source                  1..49
                        mol_type = unassigned DNA
                        organism = Homo sapiens
SEQUENCE: 55
ttccctccca ggcagctcac agtgtgccac catggagttg gggcccta                49

SEQ ID NO: 56           moltype = DNA   length = 49
FEATURE                 Location/Qualifiers
source                  1..49
                        mol_type = unassigned DNA
                        organism = Homo sapiens
SEQUENCE: 56
tgcctctacc acttctatga ccagatggac ctggctggag aagaagaga               49

SEQ ID NO: 57           moltype = DNA   length = 49
FEATURE                 Location/Qualifiers
source                  1..49
                        mol_type = unassigned DNA
                        organism = Homo sapiens
SEQUENCE: 57
tcttcatcca agggactttt cctcccagaa cccgacacag acaccatca               49

SEQ ID NO: 58           moltype = DNA   length = 49
FEATURE                 Location/Qualifiers
source                  1..49
                        mol_type = unassigned DNA
                        organism = Homo sapiens
SEQUENCE: 58
tgttgtgtga catggaaggt gatgaagaga ccagggaggc ttatgccaa                49

SEQ ID NO: 59           moltype = DNA   length = 47
FEATURE                 Location/Qualifiers
source                  1..47
                        mol_type = unassigned DNA
                        organism = Homo sapiens
SEQUENCE: 59
ccaaagattc aggtttactc acgtcatcca gcagagaatg gaaagtc                 47

SEQ ID NO: 60           moltype = DNA   length = 49
FEATURE                 Location/Qualifiers
source                  1..49
                        mol_type = unassigned DNA
                        organism = Homo sapiens
SEQUENCE: 60
ttgtcccaca gatatccaga accctgaccc tgccgtgtac cagctgaga               49

SEQ ID NO: 61           moltype = DNA   length = 49
FEATURE                 Location/Qualifiers
source                  1..49
                        mol_type = unassigned DNA
                        organism = Homo sapiens
SEQUENCE: 61
tgtgtttgag ccatcagaag cagagatctc ccacacccaa aaggccaca               49

SEQ ID NO: 62           moltype = DNA   length = 50
FEATURE                 Location/Qualifiers
source                  1..50
                        mol_type = unassigned DNA
```

```
                              organism = Homo sapiens
SEQUENCE: 62
ttcccacccg aggtcgctgt gtttgagcca tcagaagcag agatctccca                50

SEQ ID NO: 63           moltype = DNA  length = 49
FEATURE                 Location/Qualifiers
source                  1..49
                        mol_type = unassigned DNA
                        organism = Homo sapiens
SEQUENCE: 63
tttagaaagt tcctgtgatg tcaagctggt cgagaaaagc tttgaaaca                 49

SEQ ID NO: 64           moltype = DNA  length = 49
FEATURE                 Location/Qualifiers
source                  1..49
                        mol_type = unassigned DNA
                        organism = Homo sapiens
SEQUENCE: 64
tccagtgaca agtctgtctg cctattcacc gattttgatt ctcaaacaa                 49

SEQ ID NO: 65           moltype = DNA  length = 49
FEATURE                 Location/Qualifiers
source                  1..49
                        mol_type = unassigned DNA
                        organism = Homo sapiens
SEQUENCE: 65
tatatcacag acaaaactgt gctagacatg aggtctatgg acttcaaga                 49

SEQ ID NO: 66           moltype = DNA  length = 49
FEATURE                 Location/Qualifiers
source                  1..49
                        mol_type = unassigned DNA
                        organism = Homo sapiens
SEQUENCE: 66
tgaggtctat ggacttcaag agcaacagtg ctgtggcctg agcaacaa                  49

SEQ ID NO: 67           moltype = DNA  length = 2814
FEATURE                 Location/Qualifiers
misc_feature            1..2814
                        note = TALE-nuclease sequence
source                  1..2814
                        mol_type = other DNA
                        organism = synthetic construct
SEQUENCE: 67
atgggcgatc ctaaaaagaa acgtaaggtc atcgattacc catacgatgt tccagattac     60
gctatcgata tcgccgatct acgcacgctc ggctacagcc agcagcaaca ggagaagatc    120
aaaccgaagg ttcgttcgac agtggcgcag caccacgagg cactggttcg ccacgggttt    180
acacacgcgc acatcgttgc gttaagccaa caccccggcag cgttagggac cgtcgctgtc    240
aagtatcagg acatgatcgc agcgttgcca gaggcgacac acgaagcgat cgttggcgtc    300
ggcaaacagt ggtccggcgc acgcgctctg gaggccttgc tcacggtggc gggagagttg    360
agaggtccac cgttacagtt ggacacaggc caacttctca agattgcaaa acgtggcggc    420
gtgaccgcag tggaggcagt gcatgcatgg cgcaatgcac tgacgggtgc cccgctcaac    480
ttgacccccg agcaggtggt ggccatcgcc agccacgatg gcggcaagca ggcgctggag    540
acggtccagc ggctgttgcc ggtgctgtgc caggcccacg gcttgacccc ggagcaggtg    600
gtggccatcg ccagcacga tggcggcaag caggcgctgg agacggtcca gcggctgttg    660
ccggtgctgt gccaggccca cggcttgacc ccggagcagg tggtggccat cgccagcaat    720
attggtggca agcaggcgct ggagacggtc agcgcgctgt tgccggtgct gtgccaggcc    780
cacggcttga ccccggagca ggtggtggcc atcgccagca atattggtgg caagcaggcg    840
ctggagacgg tgcaggcgct gttgccggtg ctgtgccagg cccacggctt gaccccggag    900
caggtggtgg ccatcgccag caatattggt ggcaagcagg cgctggagac ggtgagaga    960
ctgttgccgg tgctgtgcca ggcccacggc ttgacccccc agcaggtggt ggccatcgcc   1020
agcaataatg gtggcaagca ggcgctggag acggtccagc ggctgttgcc ggtgctgtgc   1080
caggcccacg gcttgacccc ggagcaggtg gtggccatcg ccagcaatat tggtggcaag   1140
caggcgctgg agacggtgca ggcgctgttg ccggtgctgt gccaggccca cggcttgacc   1200
cccagcagg tggtggccat cgccagcaat ggcggtggca agcaggcgct ggagacggtc   1260
cagcggctgt tgccggtgct gtgccaggcc cacggcttga ccccccagca ggtggtggcc   1320
atcgccagca atggcggtgg caagcaggcg ctggagacgg tccagcggct gttgccggtc   1380
ctgtgccagg cccacggctt gaccccggag caggtggtgg ccatcgccag ccacgatggc   1440
ggcaagcagg cgctggagac ggtccaagcgg ctgttgtgcc agcacgacgg   1500
ttgaccccgg agcaggtggt ggccatcgcc agcaatattg gtggcaagca ggcgctggag   1560
acggtcagg cgctgttgcc ggtgctgtgc caggcccacg gcttgacccc cagcaggtg   1620
gtggccatcg ccagcaataa tggtggcaag caggcgctgg agacggtcca gcggctgttg   1680
ccggtgctgt gccaggccca cggcttgacc cccagcagg tggtggccat cgccagcaat   1740
aatggtggca agcaggcgct ggagacggtc agcgcgctgt tgccggtgct gtgccaggcc   1800
cacggcttga ccccccagca ggtggtggcc atcgccagca atggcggtgg caagcaggcg   1860
ctggagacgg tccagcggct gttgccggtg ctgtgccagg cccacggctt gacccccccag   1920
caggtggtgg ccatcgccag caatggcggt ggcaagcagg cgctgagac ggtccagcgg   1980
ctgttgccgg tgctgtgcca ggcccacggc ttgacccctc agcaggtggt ggccatcgcc   2040
agcaatggcg gcggcaggcc ggcgctggag cattgttg cccagttatc tcgccctgat   2100
```

```
ccggcgttgg ccgcgttgac caacgaccac ctcgtcgcct tggcctgcct cggcgggcgt    2160
cctgcgctgg atgcagtgaa aaagggattg gggatcccta tcagccgttc ccagctggtg    2220
aagtccgagc tggaggagaa gaaatccgag ttgaggcaca agctgaagta cgtgccccac    2280
gagtacatcg agctgatcga gatcgcccgg aacagcaccc aggaccgtat cctggagatg    2340
aaggtgatgg agttcttcat gaaggtgtac ggctacaagg gcaagcacct gggcggctcc    2400
aggaagcccg acggcgccat ctacaccgtg ggctccccca tcgactacgg cgtgatcgtg    2460
gacaccaagg cctactccgg cggctacaac ctgcccatcg gccaggccga cgaaatgcag    2520
aggtacgtgg aggagaacca gaccaggaac aagcacatca ccccaacga gtggtggaag    2580
gtgtacccct ccagcgtgac cgagttcaag ttcctgttcg tgtccggcca cttcaagggc    2640
aactacaagg cccagctgac caggctgaac cacatcacca actgcaacgg cgccgtgctg    2700
tccgtggagg agctcctgat cggcggcgag atgatcaagg ccggcaccct gaccctggag    2760
gaggtgagga ggaagttcaa caacggcgag atcaacttcg cggccgactg ataa          2814

SEQ ID NO: 68           moltype = DNA  length = 2832
FEATURE                 Location/Qualifiers
misc_feature            1..2832
                        note = TALE-nuclease sequence
source                  1..2832
                        mol_type = other DNA
                        organism = synthetic construct
SEQUENCE: 68
atgggcgatc ctaaaaagaa acgtaaggtc atcgataagg agaccgccgc tgccaagttc     60
gagagacagc acatggacag catcgatatc gccgatctac gcacgctcgg ctacagccag    120
cagcaacagg agaagatcaa accgaaggtt cgttcgacag tggcgcagca ccacgaggca    180
ctggtcggcc acgggtttac acacgcgcac atcgttgcgt taagccaaca cccggcagcg    240
ttagggaccg tcgctgtcaa gtatcaggac atgatcgcac cgttgccaga cgcgacacac    300
gaagcgatcg ttggcgtcgg caaacagtgt ccggcgcaca gcgctctgga ggccttgctc    360
acggtggcgg gagagttgag aggtccaccg ttacagttgg acacaggcca acttctcaag    420
attgcaaaac gtggcggcgt gaccgcagtg gaggcagtgc atgcatggcg caatgcactg    480
acgggtgccc cgctcaactt gacccccag caggtggtg ccatcgccag caataatggt    540
ggcaagcagg cgctggagac ggtccagcgg ctgttgccgg tgctgtgcca ggcccacggc    600
ttgacccegg agcaggtggt ggccatcgcc agcaatattg gtggcaagca ggcgctggag    660
acggtgcagg cgctgttgcc ggtgctgtgc aggcccacg gcttgaccce ggagcaggtg    720
gtggccatcg ccagccacga tggcggcaag caggcgctg agacggtcca gcggctgttg    780
ccggtgctgt gccaggccca cggcttgacc cccagcagg tggtggccat cgccagcaat    840
ggcggtggca agcaggcgct ggagacggtc cagcggctgt tgccggtgct gtgccaggcc    900
cacggcttga ccccccagca ggtggtggcc atcgccagca atggcggtgg caagcaggcg    960
ctggagacgt ccagcggct gttgccggtg ctgtgccagg cccacggctt gacccccag   1020
caggtggtgg ccatcgccag caatggcggt ggcaagcagg cgctggagac ggtccagcgg   1080
ctgttgccgg tgctgtgcca ggcccacggc ttgaccccgg agcaggtggt ggccatcgcc   1140
agccacgatg gcggcaagca ggcgctggag acggtccagc ggctgttgcc ggtgctgtgc   1200
caggcccacg gcttgacccc ggagcaggtg gtggccatcg ccagccacga tggcggcaag   1260
caggcgctgg agacggtcca gcggctgttg ccggtgctgt gccaggccca cggcttgacc   1320
ccggagcagg tggtggccat cgccagcaat attggtggca agcaggcgct ggagacggtg   1380
caggcgctgt tgccggtgct gtgccaggcc cacggcttga ccccccagca ggtggtggcc   1440
atcgccagca atggcggtgg caagcaggcg ctggagacgt ccagcggct gttgccggtg   1500
ctgtgccagg cccacggctt gaccccccag caggtggtgg ccatcgccag caatggcggt   1560
ggcaagcagg cgctggagac ggtccagcgg ctgttgccgg tgctgtgcca ggcccacggc   1620
ttgaccccgg agcaggtggt ggccatcgcc agccacgatg gcggcaagca ggcgctggag   1680
acggtccagc ggctgttgcc ggtgctgtgc caggcccacg gcttgacccc ccagcaggtg   1740
gtggccatcg ccagcaatgg cggtggcaag caggcgctgg agacggtcca gcggctgttg   1800
ccggtgctgt gccaggccca cggcttgacc ccggagcagg tggtggccat cgccagccac   1860
gatggcggca agcaggcgct ggagacggtc agcggctgt tgccggtgct gtgccaggcc    1920
cacggcttga ccccccagca ggtggtggcc atcgccagca atggcggtgg caagcaggcg   1980
ctggagacgg tccagcggct gttgccggtg ctgtgccagg cccacggctt gacccctcag   2040
caggtggtgg ccatcgccag caatggcggc ggcaggccgg cgctggagag cattgttgcc   2100
cagttatctc gccctgatcc ggcgttggcc gcgttgacca acgaccacct cgtcgccttg   2160
gcctgcctcg gcgggcgtcc tgcgctggat gcagtgaaaa agggattggg ggatcctatc   2220
agccgttccc agctggtgaa gtccgagctg gaggagaaga atccgagtt gaggcacaag   2280
ctgaagtacg tgccccacga gtacatcgag ctgatcgaga tcgcccggaa cagcacccag   2340
gaccgtatcc tggagatgaa ggtgatggag ttcttcatga aggtgtacgg ctacagggge   2400
aagcacctgg gcggctccag gaagcccgac ggcgccatct acaccgtggg ctcccccatc   2460
gactacggcg tgatcgtgga caccaaggcc tactccggcg gctacaacct gcccatcggc   2520
caggccgacg aaatgcagag gtacgtggag gagaaccaga ccaggaacaa gcacatccag   2580
cccaacgagt ggtggaaggt gtacccctcc agcgtgaccg agttcaagtt cctgttcgtg   2640
tccggccact tcaagggcaa ctacaaggcc cagctgacca ggctgaacca catcaccaac   2700
tgcaacggcg ccgtgctgtc cgtggaggag ctcctgatcg gcggcgagat gatcaaggcc   2760
ggcaccctga ccctggagga ggtgaggagg aagttcaaca acggcgagat caacttcgcg   2820
gccgactgat aa                                                         2832

SEQ ID NO: 69           moltype = DNA  length = 2814
FEATURE                 Location/Qualifiers
misc_feature            1..2814
                        note = TALE-nuclease sequence
source                  1..2814
                        mol_type = other DNA
                        organism = synthetic construct
SEQUENCE: 69
atgggcgatc ctaaaaagaa acgtaaggtc atcgattacc catacgatgt tccagattac     60
```

```
gctatcgata tcgccgatct acgcacgctc ggctacagcc agcagcaaca ggagaagatc    120
aaaccgaagg ttcgttcgac agtgcgcag caccacgagg cactggtcgg ccacgggttt    180
acacacgcgc acatcgttgc gttaagccaa caccggcag cgttagggac cgtcgctgtc    240
aagtatcagg acatgatcgc agcgttgcca gaggcgacac acgaagcgat cgttggcgtc    300
ggcaaacagt ggtccggcgc cacgcgctctg gaggccttgc tcacggtggc gggagagttg    360
agaggtccac cgttacagtt ggacacaggc caacttctca agattgcaaa acgtggcggc    420
gtgaccgcag tggaggcagt gcatgcatgg cgcaatgcac tgacgggtgc cccgctcaac    480
ttgaccccc agcaggtggt ggccatcgcc agcaatggcg gtggcaagca ggcgctggag    540
acggtccagc ggctgttgcc ggtgctgtgc caggcccacg gcttgacccc ccagcaggtg    600
gtggccatcg ccagcaataa tggtggcaag caggcgctgg agacggtcca gcggctgttg    660
ccggtgctgt gccaggccca cggcttgacc cccagcagg tggtggccat cgccagcaat    720
ggcggtggca agcaggcgct ggagacggtc agcggctgt tgccggtgct gtgccaggcc    780
cacggcttga ccccggagca ggtggtggcc atcgccagcc acgatggcgg caagcaggcg    840
ctggagacgg tccagcggct gttgccggtg ctgtgccagg cccacggctt gaccccggag    900
caggtggtgg ccatcgccag ccacgatggc ggcaagcagg cgctggagac ggtccagcgg    960
ctgttgccgg tgctgtgcca ggcccacggc ttgaccccgg agcaggtggt ggccatcgcc   1020
agccacgatg cggcaagca ggcgctggag acggtccagc ggctgttgcc ggtgctgtgc   1080
caggcccacg gcttgacccc ggagcaggtg gtggccatcg ccagcaatat tggtggcaag   1140
caggcgctgg agacggtgca ggcgctgttg ccggtgctgt gccaggccca cggcttgacc   1200
ccggagcagg tggtggccat cgccagccac gatggcggca agcaggcgct ggagacggtc   1260
cagcggctgt gccggtgct gtgccaggcc cacggcttga ccccggagca ggtggtggcc   1320
atcgccagca atattggtgg caagcaggcg ctggagacgg tgcaggcgct gttgccggtg   1380
ctgtgccagg cccacggctt gaccccccag caggtggtgg ccatcgccag caataatggt   1440
ggcaagcagg cgctggagac ggtccagcgg ctgttgccgg tgctgtgcca ggcccacggc   1500
ttgaccccgg agcaggtggt ggccatcgcc agcaatattg gtggcaagca ggcgctggag   1560
acggtgcagg cgctgttgcc ggtgctgtgc caggcccacg gcttgacccc ccagcaggtg   1620
gtggccatcg ccagcaatgg cggtggcaag caggcgctgg agacggtcca gcggctgttg   1680
ccggtgctgt gccaggccca cggcttgacc ccggagcagg tggtggccat cgccagcaat   1740
attggtggca agcaggcgct ggagacggtg caggcgctgt gccggtgct gtgccaggcc   1800
cacggcttga ccccccagca ggtggtggcc atcgccagca atggcggtgg caagcaggcg   1860
ctggagacgg tccagcggct gttgccggtg ctgtgccagg cccacggctt gaccccggag   1920
caggtggtgg ccatcgccag ccacgatggc ggcaagcagg cgctggagac ggtccagcgg   1980
ctgttgccgg tgctgtgcca ggcccacggc ttgacccctc agcaggtggt ggccatcgcc   2040
agcaatggcg cggcaggcc ggcgctggag agcattgttg cccagttatc tcgccctgat   2100
ccggcgttgg ccgcgttgac caacgaccac ctcgtcgcct tggcctgcct cggcgggcgt   2160
cctgcgctgg atgcagtgaa aaagggattg gggatccta tcagccgttc ccagctggtg   2220
aagtccgagc tggaggagaa gaaatccgag ttgaggcaca agctgaagta cgtgccccac   2280
gagtacatcg agctgatcga atcgcccgg aacagcaccc aggaccgtat cctggagatg   2340
aaggtgagtg agttcttcat gaaggtgtac ggctacaggg gcaagcacct gggcggctcc   2400
aggaagcccg acggcgccat ctacaccgtg ggctccccca tcgactacgg cgtgatcgtg   2460
gacaccaagg cctactccgg cggctacaac ctgcccatcg gccaggccga cgaaatgcag   2520
aggtacgtgg aggagaacca gaccaggaac aagcacatca ccccaacga gtggtggaag   2580
gtgtacccct ccagcgtgac cgagttcaag ttcctgttcg tgtccggcca cttcaagggc   2640
aactacaagg cccagctgac caggctgaac cacatcacca actgcaacgg cgccgtgctg   2700
tccgtggagg agctcctgat cggcggcgag atgatcaagg ccggcaccct gaccctggag   2760
gaggtgagga ggaagttcaa caacggcgag atcaacttcg cggccgactg ataa         2814
```

```
SEQ ID NO: 70          moltype = DNA   length = 2832
FEATURE                Location/Qualifiers
misc_feature           1..2832
                       note = TALE-nuclease sequence
source                 1..2832
                       mol_type = other DNA
                       organism = synthetic construct
SEQUENCE: 70
atgggcgatc ctaaaaagaa acgtaaggtc atcgataagg agaccgccgc tgccaagttc     60
gagagacagc acatggacag catcgatatc gccgatctac gcacgctcgg ctacagccag    120
cagcaacagg agaagatcaa accgaaggtt cgttcgacag tggcgcagca ccacgaggca    180
ctggtcggcc acgggtttac acacgcgcac atcgttgcgt taagccaaca cccggcagcg    240
ttagggaccg tcgctgtcaa gtatcaggac atgatcgcag cgttgccaga ggcgacacac    300
gaagcgatcg ttggcgtcgg caaacagtgg tccggcgcac gcgctctgga ggccttgctc    360
acggtggcgg gagagttgag aggtccaccg ttacagttgg acacaggcca acttctcaag    420
attgcaaaac gtggcggcgt gaccgcagtg gaggcagtga tgcatggcg caatgcactg    480
acgggtgccc cgctcaactt gacccccgag caggtggtgg ccatcgccag ccacgatggc    540
ggcaagcagg cgctggagac ggtccagcgg ctgttgccgg tgctgtgcca ggcccacggc    600
ttgaccccc agcaggtggt ggccatcgcc agcaatggcg gtggcaagca ggcgctggag    660
acggtccagc ggctgttgcc ggtgctgtgc caggcccacg gcttgacccc ggagcaggtg    720
gtggccatcg ccagcacga tggcggcaag caggcgctgg agacggtcca gcggctgttg    780
ccggtgctgt gccaggccca cggcttgacc ccggagcagg tggtggccat cgccagcaat    840
attggtggca agcaggcgct ggagacggtg caggcgctgt gccggtgct gtgccaggcc    900
cacggcttga ccccccagca ggtggtggcc atcgccagca ataatggtgg caagcaggcg    960
ctggagacgg tccagcggct gttgccggtg ctgtgccagg cccacggctt gaccccggag   1020
caggtggtgg ccatcgccag ccacgatggc ggcaagcagg cgctggagac ggtccagcgg   1080
ctgttgccgg tgctgtgcca ggcccacggc ttgaccccag caggtggt ggccatcgcc   1140
agcaatggcg tggcaagca ggcgctggag acggtccagc ggctgttgcc ggtgctgtgc   1200
caggcccacg gcttgacccc cagcaggtg tggccatcg ccagcaataa tggtggcaag   1260
caggcgctgg agacggtcca gcggctgttg ccggtgctgt gccaggccca cggcttgacc   1320
ccccagcagg tggtggccat cgccagcaat aatggtggca agcaggcgct ggagacggtc   1380
cagcggctgt gccggtgct gtgccaggcc cacggcttga ccccccagca ggtggtggcc   1440
```

```
atcgccagca atggcggtgg caagcaggcg ctggagacgg tccagcggct gttgccggtg   1500
ctgtgccagg cccacggctt gacccccgga caggtggtgg ccatcgccag caatattggt   1560
ggcaagcagg cgctggagac ggtgcaggcg ctgttgccgg tgctgtgcca ggcccacggc   1620
ttgacccccg agcaggtggt ggccatcgcc agccacgatg cggcaagcag ggcgctggag   1680
acggtccagc ggctgttgcc ggtgctgtgc caggcccacg gcttgacccc ggagcaggtg   1740
gtggccatcg ccagcaatat tggtggcaag caggcgctgg agacggtgca ggcgctgttg   1800
ccggtgctgt gccaggccca cggcttgacc ccggagcagg tggtggccat cgccagccac   1860
gatggcggca agcaggcgct ggagacggtc agcggctgt tgccggtgct gtgccaggcc   1920
cacggcttga cccccaagca ggtggtggcc atcgccagca ataatggtgg caagcaggcg   1980
ctggagacgg tccagcggct gttgccggtg ctgtgccagg cccacggctt gacccctcag   2040
caggtggtgg ccatcgccag caatggcggc ggcaggccgg cgctggagag cattgttgcc   2100
cagttatctc gccctgatcc ggcgttggcc gcgttgacca acgaccacct cgtcgccttg   2160
gcctgcctcg gcgggcgtcc tgcgctggat gcagtgaaaa agggattggg ggatcctatc   2220
agccgttccc agctggtgaa gtccgagctg gaggagaaga atccgagtt gaggcacaag   2280
ctgaagtacg tgccccacga gtacatcgag ctgatcgaga tcgcccggaa cagcacccag   2340
gaccgtatcc tggagatgaa ggtgatggag ttcttcatga aggtgtacgg ctacaggggc   2400
aagcacctgg cggctccag gaagcccgac ggcgccatct acaccgtggg ctcccccatc   2460
gactacggcg tgatcgtgga caccaaggcc tactccggcg gctacaacct gcccatcggc   2520
caggccgacg aaatgcagag gtacgtggag gagaaccaga ccaggaacaa gcacatcaac   2580
cccaacagt ggtggaaggt gtaccctcc agcgtgaccg agttcaagtt cctgttcgtg   2640
tccgccact tcaagggcaa ctacaaggcc agctgacca ggctgaacca catcaccaac   2700
tgcaacggcg ccgtgctgtc cgtggaggag ctcctgatcg gcggcgagat gatcaaggcc   2760
ggcaccctga ccctggagga ggtgaggagg aagttcaaca acggcgagat caacttcgcg   2820
gccgactgat aa                                                       2832
SEQ ID NO: 71          moltype = DNA   length = 2814
FEATURE                Location/Qualifiers
misc_feature           1..2814
                       note = TALE-nuclease sequence
source                 1..2814
                       mol_type = other DNA
                       organism = synthetic construct
SEQUENCE: 71
atgggcgatc ctaaaaagaa acgtaaggtc atcgattacc catacgatgt tccagattac     60
gctatcgata tcgccgatct acgcacgctc ggctacagcc agcagcaaca ggagaagatc   120
aaaccgaagg ttcgttcgac agtggcgcag caccacgagg cactggtcgg ccacgggttt   180
acacacgcgc atcgttgc gttaagccaa cacccggcag cgttagggac cgtcgctgtc   240
aagtatcagg acatgatcgc agcgttgcca gaggcgacac acgaagcgat cgttggcgtc   300
ggcaaacagt ggtccggcgc acgcgctctg gaggccttgc tcacggtgcg gggagagttg   360
agaggtccac cgttacagtt ggacacaggc caacttctca agattgcaaa acgtggcggc   420
gtgaccgcag tggaggcagt gcatgcatgg cgcaatgcac tgacgggtgc cccgctcaac   480
ttgacccccc agcaggtggt ggccatcgcc agcaataatg tggcaagca ggcgctggag   540
acggtccagc ggctgttgcc ggtgctgtgc caggcccacg gcttgacccc ccagcaggtg   600
gtggccatcg ccagcaatgg cggtggcaag caggcgctgg agacggtcca gcggctgttg   660
ccggtgctgt gccaggccca cggcttgacc cccagcagg tggtggccat cgccagcaat   720
aatggtggca agcaggcgct ggagacggtc agcggctgt tgccggtgct gtgccaggcc   780
cacggcttga cccccagca ggtggtggcc atcgccagca atggcggtgg caagcaggcg   840
ctggagacgg tccagcggct gttgccggtg ctgtgccagg cccacggctt gaccccccag   900
caggtggtgg ccatcgccag caatggcggt ggcaagcagg cgctggagac ggtccagcgg   960
ctgttgccgg tgctgtgcca ggcccacggc ttgacccccc agcaggtggt ggccatcgcc   1020
agcaatggcg gtgtggcaagca ggcgctggag acggtccagc ggctgttgcc ggtgctgtgc   1080
caggcccacg gcttgacccc ccagcaggtg gtggccatcg ccagcaataa tggtggcaag   1140
caggcgctgg agacggtcca gcggctgttg ccggtgctgt gccaggccca cggcttgacc   1200
ccggagcagg tggtggccat cgccagcaat attggtggca agcaggcgct ggagacggtg   1260
caggcgctgt tgccggtgct gtgccaggcc cacggcttga cccccagca ggtggtggcc   1320
atcgccagca ataatggtgg caagcaggcg ctggagacgg tccagcggct gttgccggtg   1380
ctgtgccagg cccacggctt gaccccggag caggtggtgg ccatcgccag ccacgatggc   1440
ggcaagcagg cgctggagac ggtccagcgg ctgttgccgg tgctgtgcca ggcccacggc   1500
ttgacccccg agcaggtggt ggccatcgcc agccacgatg cggcaagcag ggcgctggag   1560
acggtccagc ggctgttgcc ggtgctgtgc caggcccacg gcttgacccc ggagcaggtg   1620
gtggccatcg ccagcaatat tggtggcaag caggcgctgg agacggtgca ggcgctgttg   1680
ccggtgctgt gccaggccca cggcttgacc ccccagcagg tggtggccat cgccagcaat   1740
ggcggtggca agcaggcgct ggagacggtc agcggctgt tgccggtgct gtgccaggcc   1800
cacggcttga ccccggagca ggtggtggcc atcgccagcc acgatggcgg caagcaggcg   1860
ctggagacgg tccagcggct gttgccggtg ctgtgccagg cccacggctt gaccccggag   1920
caggtggtgg ccatcgccag caatattggt ggcaagcagg cgctggagac ggtgcaggcg   1980
ctgttgccgg tgctgtgcca ggcccacggc ttgacccctc agcaggtggt ggccatcgcc   2040
agcaatggcg gcggcaggcc ggcgctggag agcattgttg cccagtttatc tcgccctgat   2100
ccggcgttgg ccgcgttgac caacgaccac ctcgtcgcct tggcctgcct cggcgggcgt   2160
cctgcgctgg atgcagtgaa aaagggattg ggggatccta tcagccgttc ccagctggtg   2220
aagtccgagc tggaggagaa gaatccgagt tgaggcaca agctgaagta cgtgccccac   2280
gagtacatcg agctgatcga gatcgcccgg aacagcaccc aggaccgtat cctggagatg   2340
aaggtgatgg agttcttcat gaaggtgtac ggctacaggg caagcacct gggcggctcc   2400
aggaagcccg acggcgccat ctacaccgtg gctccccca tcgactacgg cgtgatcgtg   2460
gacaccaagg cctactccgg cggctacaac ctgcccatcg gccaggccga cgaaatgcag   2520
aggtacgtgg aggagaacca gaccaggaac aagcacatca ccccaacga gtggtggaag   2580
gtgtacccct ccagcgtgac cgagttcaag ttcctgttcg tgtccggcca cttcaagggc   2640
aactacaagg cccagctgac caggctgaac acatcacca actgcaacgg cgccgtgctg   2700
tccgtggagg agctcctgat cggcggcgag atgatcaagg ccggcaccct gaccctggag   2760
```

| | | |
|---|---|---|
| gaggtgagga | ggaagttcaa caacggcgag atcaacttcg cggccgactg ataa | 2814 |

SEQ ID NO: 72   moltype = DNA   length = 2832
FEATURE        Location/Qualifiers
misc_feature   1..2832
               note = TALE-nuclease sequence
source         1..2832
               mol_type = other DNA
               organism = synthetic construct
SEQUENCE: 72

| | | |
|---|---|---|
| atgggcgatc | ctaaaaagaa acgtaaggtc atcgataagg agaccgccgc tgccaagttc | 60 |
| gagagacagc | acatggacag catcgatatc gccgatctac gcacgctcgg ctacagccag | 120 |
| cagcaacagg | agaagatcaa accgaaggtt cgttcgacag tggcgcagca ccacgaggca | 180 |
| ctggtcggcc | acgggtttac acacgcgcac atcgttcgt taagccaaca ccggcagtcg | 240 |
| ttagggaccg | tcgctgtcaa gtatcaggac atgatcgcag cgttgccaga ggcgacacac | 300 |
| gaagcgatcg | ttggcgtcgg caaacagtgg tccggcgcac gcgctctgga ggccttgctc | 360 |
| acggtggcgg | gagagttgag aggtccaccg ttacagttgg acacaggcca acttctcaag | 420 |
| attgcaaaac | gtggcggcgt gaccgcagtg gaggcagtgc atgcatggcg caatgcactg | 480 |
| acgggtgccc | cgctcaactt gacccccag caggtggtgg ccatcgccag caataatggt | 540 |
| ggcaagcagg | cgctggagac ggtccagcgg ctgttgccgg tgctgtgcca ggcccacggc | 600 |
| ttgacccccc | agcaggtggt ggccatcgcc agcaatggcg gtggcaagca ggcgctggag | 660 |
| acggtccagc | ggctgttgcc ggtgctgtgc caggcccacg gcttgacccc ccagcaggtg | 720 |
| gtggccatcg | ccagcaataa tggtggcaag caggcgctgg agacggtcca gcggctgttg | 780 |
| ccggtgctgt | gccaggccca cggcttgacc cccagcagg tggtggccat cgccagcaat | 840 |
| aatggtggca | agcaggcgct ggagacggtc agcggctgt tgccggtgct gtgccaggcc | 900 |
| cacggcttga | ccccgagca ggtggtggcc atcgccagc acgatggcg caagcaggcg | 960 |
| ctggagacgg | tccagcggct gttgccggtg ctgtgccagg cccacggctt gaccccggaa | 1020 |
| caggtggtgg | ccatcgccag ccacgatggc ggcaagcagg cgctggagac ggtccagcgg | 1080 |
| ctgttgccgg | tgctgtgcca ggcccacggc ttgacccccc agcaggtggt ggccatcgcc | 1140 |
| agcaatggcg | gtggcaagca ggcgtccagc ggctgttgcc ggtgctgtgc | 1200 |
| caggcccacg | gcttgacccc cagcaggtg gtggccatcg ccagcaatgg cggtggcaag | 1260 |
| caggcgctgg | agacggtcca gcggctgttg ccggtgctgt gccaggccca cggcttgacc | 1320 |
| ccccagcagg | tggtggccat cgccagcaat ggcggtggca agcaggcgct ggagacggtc | 1380 |
| cagcggctgt | tgccggtgct gtgccaggcc cacggcttga cccccagca ggtggtggcc | 1440 |
| atcgccagca | atggcggtgg caagcaggcg ctggagacgg tccagcggct gttgccggtg | 1500 |
| ctgtgccagg | cccacggctt gacccccag caggtggtgg ccatcgccag caataatggt | 1560 |
| ggcaagcagg | cgctggagac ggtccagcgg ctgttgccgg tgctgtgcca ggcccacggc | 1620 |
| ttgacccccc | agcaggtggt ggccatcgcc agcaataatg gtggcaagca ggcgctggag | 1680 |
| acggtccagc | ggctgttgcc ggtgctgtgc caggcccacg gcttgacccc ccagcaggtg | 1740 |
| gtggccatcg | ccagcaataa tggtggcaag caggcgctgg agacggtcca gcggctgttg | 1800 |
| ccggtgctgt | gccaggccca cggcttgacc cccagcagg tggtggccat cgccagcaat | 1860 |
| ggcggtggca | agcaggcgct ggagacggtc agcggctgt tgccggtgct gtgccaggcc | 1920 |
| cacggcttga | ccccccagca ggtggtggcc atcgccagc acgatggcg caagcaggcg | 1980 |
| ctggagacgg | tccagcggct gttgccggtg ctgtgccagg cccacggctt gaccccccag | 2040 |
| caggtggtgg | ccatcgccag caatggcggc ggcaggccgg cgctggagag cattgttgcc | 2100 |
| cagttatctc | gccctgatcc ggcgttggcc gcgttgacca cgaccacct cgtcgccttg | 2160 |
| gcctcctcg | gcggggcgtcc tgcgctggat gcagtgaaaa agggattggg ggatcctatc | 2220 |
| agccgttccc | agctggtgaa gtccgagctg gaggagaaga atccgagtt gaggcacaag | 2280 |
| ctgaagtacg | tgccccacga gtacatcgag ctgatcgaga tcgcccggaa cagcacccag | 2340 |
| gaccgtatcc | tggagatgaa ggtgatggag ttcttcatga aggtgtacgg ctacaggggc | 2400 |
| aagcacctgg | gcggctccag gaagcccgac ggcgccatct acaccgtggg ctccccccctg | 2460 |
| gactacggcg | tgatcgtgga caccaaggcc tactccggcg gctacaacct gcccatcggc | 2520 |
| caggccgacg | aaatgcagag gtacgtggag gagaaccaga ccaggaacaa gcacatcaac | 2580 |
| cccaacgagt | ggtggaaggt gtaccctcc agcgtgaccg agttcaagtt cctgttcgtg | 2640 |
| tccggccact | tcaagggcaa ctacaaggcc cagctgaccc ggctgaacca catcaccaac | 2700 |
| tgcaacggcg | ccgtgctgtc cgtcgaggag ctcctgatcg gcggcgagat gatcaaggcc | 2760 |
| ggcacccgga | ccctggagga ggtgaggagg aagttcaaca acggcgagat caacttcgcg | 2820 |
| gccgactgat | aa | 2832 |

SEQ ID NO: 73   moltype = DNA   length = 2814
FEATURE        Location/Qualifiers
misc_feature   1..2814
               note = TALE-nuclease sequence
source         1..2814
               mol_type = other DNA
               organism = synthetic construct
SEQUENCE: 73

| | | |
|---|---|---|
| atgggcgatc | ctaaaaagaa acgtaaggtc atcgattacc catacgatgt tccagattac | 60 |
| gctatcgata | tcgccgatct acgcacgctc ggctacagcc agcagcaaca ggagaagatc | 120 |
| aaaccgaagg | ttcgttcgac agtggcgcag caccacgagg cactggtcgg ccacgggttt | 180 |
| acacacgcgc | acatcgttgc gttaagccaa caccggcagc gttagggac cgtcgctgtc | 240 |
| aagtatcagg | acatgatcgc agcgttgcca gaggcgacac acgaagcgat cgttggcgtc | 300 |
| ggcaaacagt | ggtccggcgc acgcgctctg gaggccttgc tcacggtggc gggagagttg | 360 |
| agaggtccac | cgttacagtt ggacacaggc caacttctca agattgcaaa acgtggcggc | 420 |
| gtgaccgcag | tggaggcagt gcatgcatgg cgcaatgcac tgacgggtgc cccgctcaac | 480 |
| ttgacccccgg | agcaggtggt ggccatcgcc agcacgatg cggcaagca ggcgctggag | 540 |
| acggtccagc | ggctgttgcc ggtgctgtgc caggcccacg cttgacccc ggagcaggtg | 600 |
| gtggccatcg | ccagccacga tggcggcaag caggcgctgg agacggtcca gcggctgttg | 660 |
| ccggtgctgt | gccaggccca cggcttgacc ccggagcagg tggtggccat cgccagccac | 720 |

```
gatggcggca agcaggcgct ggagacggtc cagcggctgt tgccggtgct gtgccaggcc    780
cacggcttga cccccgagca ggtggtggcc atcgccagca atattggtgg caagcaggcg    840
ctggagacgg tgcaggcgct gttgccggtg ctgtgccagg cccacggctt gaccccggag    900
caggtggtgg ccatcgccag ccacgatggc ggcaagcagg cgctggagac ggtccagcgg    960
ctgttgccgg tgctgtgcca ggcccacggc ttgaccccgg agcaggtggt ggccatcgcc   1020
agccacgatg gcggcaagca ggcgctggag acggtccagc ggctgttgcc ggtgctgtgc   1080
caggcccacg gcttgacccc ggagcaggtg gtggccatcg ccagccacga tggcggcaag   1140
caggcgctgg agacggtcca gcggctgttg ccggtgctgt gccaggccca cggcttgacc   1200
ccccagcagg tggtggccat cgccagcaat aatggtggca agcaggcgct ggagacggtc   1260
cagcggctgt tgccggtgct gtgccaggcc cacggcttga cccccgagca ggtggtggcc   1320
atcgccagca atattggtgg caagcaggcg ctggagacgg tgcaggcgct gttgccggtg   1380
ctgtgccagg cccacggctt gaccccccag caggtggtgg ccatcgccag caataatggt   1440
ggcaagcagg cgctggagac ggtccagcgg ctgttgccgg tgctgtgcca ggcccacggc   1500
ttgaccccccagcaggtggt ggccatcgcc agcaataatg gtggcaagca ggcgctggag   1560
acggtccagc ggctgttgcc ggtgctgtgc caggcccacg gcttgacccc ccagcaggtg   1620
gtggccatcg ccagcaatgg cggtggcaag caggcgctgg agacggtcca gcggctgttg   1680
ccggtgctgt gccaggccca cggcttgacc ccggagcagg tggtggccat cgccagccac   1740
gatggcggca agcaggcgct ggagacggtc cagcggctgt tgccggtgct gtgccaggcc   1800
cacggcttga cccccagca ggtggtggcc atcgccagca ataatggtgg caagcaggcg   1860
ctggagacgg tccagcggct gttgccggtg ctgtgccagg cccacggctt gaccccggag   1920
caggtggtgg ccatcgccag ccacgatggc ggcaagcagg cgctggagac ggtccagcgg   1980
ctgttgccgg tgctgtgcca ggcccacggc ttgaccccccagcaggtggt ggccatcgcc   2040
agcaatggcg gcggcaggcc ggcgctggag agcattgttg cccagttatc tcgccctgat   2100
ccggcgttgg ccgcgttgac caacgaccac ctcgtcgcct ggctgcctcc cggcgggcgt   2160
cctgcgctga tgcagtgaaa aagggattg ggggatccta tcagccgttc cagctggtg    2220
aagtccgagc tggaggagaa gaaatccgag ttgaggcaca agctgaagta cgtgccccac   2280
gagtacatcg agctgatcga gatcgcccgg aacagcaccc aggaccgtat cctggagatg   2340
aaggtgatgg agttcttcat gaaggtgtac ggctacaggg gcaagcacct gggcggctcc   2400
aggaagcccg acggcgccat ctacaccgtg ggctcccca tcgactacgg cgtgatcgtg   2460
gacaccaagg cctactccgg cggctacaac ctgcccatcg cccaggccga cgaaatgcag   2520
aggtacgtgg aggagaacca gaccaggaac aagcacatca accccaacga gtggtggaag   2580
gtgtaccct ccagcgtgac cgagttcaag ttcctgttcg tgtccggcca cttcaagggc   2640
aactacaagg cccagctgac caggctgaac cacatcacca actgcaacgg cgccgtgctg   2700
tccgtggagg agctcctgat cggcggcgag atgatcaagg ccggcaccct gaccctggag   2760
gaggtgagga ggaagttcaa caacggcgag atcaacttcg cggccgactg ataa         2814

SEQ ID NO: 74              moltype = DNA  length = 2832
FEATURE                    Location/Qualifiers
misc_feature               1..2832
                           note = TALE-nuclease sequence
source                     1..2832
                           mol_type = other DNA
                           organism = synthetic construct
SEQUENCE: 74
atgggcgatc ctaaaaagaa acgtaaggtc atcgataagg agaccgccgc tgccaagttc     60
gagagacagc acatggacag catcgatatc gccgatctac gcacgctcgg ctacagccag    120
cagcaacagg agaagatcaa accgaaggtt cgttcgcaga tggcgagca ccacgaggca     180
ctggtcggcc acgggtttac acacgcgcac atcgttgcgt taagccaaca cccggcagcg    240
ttagggaccg tcgctgtcaa gtatcaggac atgatcgcag cgttgccaga ggcgacacac    300
gaagcgatcg ttggcgtcgg caaacagtgg tccggcgcac gcgctctgga ggccttgctc    360
acggtggcgg gagagttgag aggtccaccg ttacagtttg acacaggcca acttctcaag    420
attgcaaaac gtggcggcgt gaccgcagtg gaggcagtgc atgcatgcg caatgcactg    480
acgggtgccc cgctcaactt gacccccccag caggtggtgg ccatcgccag caataatggt    540
ggcaagcagg cgctggagac ggtccagcgg ctgttgccgg tgctgtgcca ggcccacggc    600
ttgaccccccagcaggtggt ggccatcgcc agcaataatg gtggcaagca ggcgctggag    660
acggtccagc ggctgttgcc ggtgctgtgc caggcccacg gcttgacccc ccagcaggtg    720
gtggccatcg ccagcaataa tggtggcaag caggcgctgg agacggtcca gcggctgttg    780
ccggtgctgt gccaggccca cggcttgacc ccggagcagg tggtggccat cgccagcaat    840
attggtggca agcaggcgct ggagacggtg caggcgctgt tgccggtgct gtgccaggcc    900
cacggcttga cccccagca ggtggtggcc atcgccagca ataatggtgg caagcaggcg    960
ctggagacgg tccagcggct gttgccggtg ctgtgccagg cccacggctt gaccccggag   1020
caggtggtgg ccatcgccag caatattggt ggcaagcagg cgctggagac ggtgcaggcg   1080
ctgttgccgg tgctgtgcca ggcccacggc ttgaccccccagcaggtggt ggccatcgcc   1140
agcaatggcg gtggcaagca ggcgctggag acggtccagc ggctgttgcc ggtgctgtgc   1200
caggcccacg gcttgacccc ggagcaggtg gtggccatcg ccagccacga tggcggcaag   1260
caggcgctgg agacggtcca gcggctgttg ccggtgctgt gccaggccca cggcttgacc   1320
ccccagcagg tggtggccat cgccagcaat ggcggtggca agcaggcgct ggagacggtc   1380
cagcggctgt tgccggtgct gtgccaggcc cacggcttga cccccgagca ggtggtggcc   1440
atcgccagcc acgatggcgg caagcaggcg ctggagacgg tccagcggct gttgccggtg   1500
ctgtgccagg cccacggctt gaccccccag caggtggtgg ccatcgccag caatggcggt   1560
ggcaagcagg cgctggagac ggtccagcgg ctgttgccgg tgctgtgcca ggcccacggc   1620
ttgaccccccagcaggtggt ggccatcgcc agcaataatg gtggcaagca ggcgctggag   1680
acggtccagc ggctgttgcc ggtgctgtgc caggcccacg gcttgacccc ggagcaggtg   1740
gtggccatcg ccagcacga tggcggcaag caggcgctgg agacggtcca gcggctgttg   1800
ccggtgctgt gccaggccca cggcttgacc cccagcagg tggtggccat cgccagcaat   1860
ggcggtggca agcaggcgct ggagacggtc cagcggctgt tgccggtgct gtgccaggcc   1920
cacggcttga cccccagca ggtggtggcc atcgccagca atggcggtgg caagcaggcg   1980
ctggagacgg tccagcggct gttgccggtg ctgtgccagg cccacggctt gaccccctcag  2040
caggtggtgg ccatcgccag caatggcggc ggcaggccgg cgctggagag cattgttgcc   2100
```

```
cagttatctc gccctgatcc ggcgttggcc gcgttgacca acgaccacct cgtcgccttg 2160
gcctgcctcg gcgggcgtcc tgcgctggat gcagtgaaaa agggattggg ggatcctatc 2220
agccgttccc agctggtgaa gtccgagctg gaggagaaga aatccgagtt gaggcacaag 2280
ctgaagtacg tgccccacga gtacatcgag ctgatcgaga tcgcccggaa cagcacccag 2340
gaccgtatcc tggagatgaa ggtgatggaa ttcttcatga aggtgtacgg ctacaggggc 2400
aagcacctgg gcggctccag gaagcccgac ggcgccatct acaccgtggg ctcccccatc 2460
gactacggcg tgatcgtgga caccaaggcc tactccggcg gctacaacct gcccatcggc 2520
caggccgacg aaatgcagag gtacgtggag gagaaccaga ccaggaacaa gcacatcaac 2580
cccaacgagt ggtggaaggt gtaccccctcc agcgtgaccg agttcaagtt cctgttcgtg 2640
tccggccact tcaagggcaa ctacaaggcc cagctgaacc ggctgaacca catcaccaac 2700
tgcaacggcg ccgtgctgtc cgtggaggag ctcctgatcg gcggcgagat gatcaaggcc 2760
ggcacccctga ccctggagga ggtgaggagg aagttcaaca acggcgagat caacttcgcg 2820
gccgactgat aa                                                      2832

SEQ ID NO: 75          moltype = DNA  length = 21
FEATURE                Location/Qualifiers
misc_feature           1..21
                       note = PCR primer
source                 1..21
                       mol_type = other DNA
                       organism = synthetic construct
SEQUENCE: 75
atcactggca tctggactcc a                                            21

SEQ ID NO: 76          moltype = DNA  length = 22
FEATURE                Location/Qualifiers
misc_feature           1..22
                       note = PCR primer
source                 1..22
                       mol_type = other DNA
                       organism = synthetic construct
SEQUENCE: 76
agagccccta ccagaaccag ac                                           22

SEQ ID NO: 77          moltype = DNA  length = 22
FEATURE                Location/Qualifiers
misc_feature           1..22
                       note = PCR primer
source                 1..22
                       mol_type = other DNA
                       organism = synthetic construct
SEQUENCE: 77
ggacctagta acataattgt gc                                           22

SEQ ID NO: 78          moltype = DNA  length = 20
FEATURE                Location/Qualifiers
misc_feature           1..20
                       note = PCR primer
source                 1..20
                       mol_type = other DNA
                       organism = synthetic construct
SEQUENCE: 78
cctcatgtct agcacagttt                                              20

SEQ ID NO: 79          moltype = DNA  length = 21
FEATURE                Location/Qualifiers
misc_feature           1..21
                       note = PCR primer
source                 1..21
                       mol_type = other DNA
                       organism = synthetic construct
SEQUENCE: 79
accagctcag ctccacgtgg t                                            21

SEQ ID NO: 80          moltype = DNA  length = 58
FEATURE                Location/Qualifiers
source                 1..58
                       mol_type = unassigned DNA
                       organism = Homo sapiens
SEQUENCE: 80
tctcgctccg tggccttagc tgtgctcgcg ctactctctc tttctggcct ggaggcta    58

SEQ ID NO: 81          moltype = DNA  length = 2814
FEATURE                Location/Qualifiers
misc_feature           1..2814
                       note = Beta2M T01- TALEN - LEFT
source                 1..2814
                       mol_type = other DNA
                       organism = synthetic construct
```

```
SEQUENCE: 81
atgggcgatc ctaaaaagaa acgtaaggtc atcgattacc catacgatgt tccagattac    60
gctatcgata tcgccgatct acgcacgctc ggctacagcc agcagcaaca ggagaagatc   120
aaaccgaagg ttcgttcgac agtggcgcag caccacgagg cactggtcgg ccacgggttt   180
acacacgcgc acatcgttgc gttaagccaa cacccggcca cgttagggac cgtcgctgtc   240
aagtatcagg acatgatcgc agcgttgcca gaggcgacac acgaagcgat cgttggcgtc   300
ggcaaacagt ggtccggcgc acgcgctctg gaggccttgc tcacggtggc gggagagttg   360
agaggtccac cgttacagtt ggacacaggc caacttctca agattgcaaa acgtggcggc   420
gtgaccgcag tggaggcagt gcatgcatgg cgcaatgcac tgacgggtgc cccgctcaac   480
ttgacccccc agcaggtggt ggccatcgcc agcaataatg gtggcaagca ggcgctggag   540
acggtccagc ggctgttgcc ggtgctgtgc caggcccacg gcttgacccc ccagcaggtg   600
gtggccatcg ccagcaataa tggtggcaag caggcgctgg agacggtcca gcggctgttg   660
ccggtgctgt gccaggccca cggcttgacc cggagcaggt ggtggccat cgccagccac   720
gatggcggca agcaggcgct ggagacggtc agcggctgt tgccggtgct gtgccaggcc   780
cacggcttga ccccggagca ggtggtggcc atcgccagcc acgatggcgg caagcaggcg   840
ctggagacgg tccagcggct gttgccggtg ctgtgccagg cccacggctt gacccccag   900
caggtggtgg ccatcgccag caatggcggt ggcaagcagg cgctggagac ggtccagcgg   960
ctgttgccgg tgctgtgcca ggcccacggc ttgaccccc agcaggtggt ggccatcgcc   1020
agcaatggcg gtggcaagca ggcgctggag acggtccagc ggctgttgcc ggtgctgtgc   1080
caggcccacg gcttgacccc ggagcaggtg gtggccatcg ccagcaatat tggtggcaag   1140
caggcgctgg agacggtgca ggcgctgttg ccggtgctgt gccaggccca cggcttgacc   1200
cccagcagg tggtggccat cgccagcaat aatggtggca agcaggcgct ggagacggtc   1260
cagcggctgt gccggtgct gtgccaggcc cacggcttga ccccggagca ggtggtggcc   1320
atcgccagcc acgatggcgg caagcaggcg ctggagacgg tccagcggct gttgccggtg   1380
ctgtgccagg cccacggctt gacccccag caggtggtgg ccatcgccag caatggcggt   1440
ggcaagcagg cgctggagac ggtccagcgg ctgttgccgg tgctgtgcca ggcccacggc   1500
ttgacccccc agcaggtggt ggccatcgcc agcaataatg gtggcaagca ggcgctggag   1560
acggtccagc ggctgttgcc ggtgctgtgc caggcccacg gcttgacccc ccagcaggtg   1620
gtggccatcg ccagcaatgg cggtggcaag caggcgctgg agacggtcca gcggctgttg   1680
ccggtgctgt gccaggccca cggcttgacc cccagcaat tggtggcaa   1740
aatggtggca agcaggcgct ggagacggtc agcggctgt tgccggtgct gtgccaggct   1800
cacggcttga ccccggagca ggtggtggcc atcgccagcc acgatggcgg caagcaggcg   1860
ctggagacgg tccagcggct gttgccggtg ctgtgccagg cccacggctt gacccccag   1920
caggtggtgg ccatcgccag caatggcggt ggcaagcagg cgctggagac ggtccagcgg   1980
ctgttgccgg tgctgtgcca ggcccacggc ttgaccccc agcaggtggt ggccatcgcc   2040
agcaatggcg gcggcaggcc ggcgctggag agcattgttg cccagttatc tgccctgat   2100
ccggcgttgg ccgcgttgac caacgaccac ctcgtcgcct tggcctgcct cggcgggcgt   2160
cctgcgctgg atgcagtgaa aaagggattg ggggatccta tcagccgttc ccagctggtg   2220
aagtccgagc tggaggagaa gaaatccgag ttgaggcaca agctgaagta cgtgccccac   2280
gagtacatcg agctgatcga gatcgcccgg aacagcaccc aggaccgtat cctggagatg   2340
aaggtgatgg agttcttcat gaaggtgtac ggctacaggg gcaagcacct gggcggctcc   2400
aggaagcccg acggcgccat ctacaccgtg gctcccccca tcgactacgg cgtgatcgtg   2460
gacaccaagg cctactccgg cggctacaac ctgcccatcg gccagcgca cgaaatgcag   2520
aggtacgtgg aggagaacca gaccaggaac aagcacatca accccaacga gtggtggaag   2580
gtgtaccccct ccagcgtgac cgagttcaag ttcctgttcg tgtccggcca cttcaagggc   2640
aactacaagg cccagctgac caggctgaac cacatcacca ctgcaacgg cgccgtgctg   2700
tccgtggagg agctcctgat cggcggcgag atgatcaagg ccggcaccct gacccctgag   2760
gaggtgagga ggaagttcaa caacggcgag atcaacttcg cggccgactg ataa        2814
```

SEQ ID NO: 82  moltype = DNA  length = 2832
FEATURE        Location/Qualifiers
misc_feature   1..2832
               note = Beta2M T01 TALEN -RIGHT
source         1..2832
               mol_type = other DNA
               organism = synthetic construct

```
SEQUENCE: 82
atgggcgatc ctaaaaagaa acgtaaggtc atcgataagg agaccgccgc tgccaagttc    60
gagagacagc acatggacag catcgatatc gccgatctac gcacgctcgg ctacagccag   120
cagcaacagg agaagatcaa accgaaggtt cgttcgacag tggcgcagca ccacgaggca   180
ctggtcggcc acgggtttac acacgcgcac atcgttgcgt taagccaaca cccggcagca   240
ttagggaccg tcgctgtcaa gtatcaggac atgatcgcag cgttgccaga ggcgacacac   300
gaagcgatcg ttggcgtcgg caaacagtgg tccggcgcac gcgctctgga ggccttgctc   360
acggtggcgg gagagttgag aggtccaccg ttacagttga cacaggcca acttctcaag   420
attgcaaaac gtggcggcgt gaccgcagtg gaggcagtgc atgcatggcg caatgcactg   480
acgggtgccc cgctcaactt gacccccgag caggtggtgg ccatcgccag caatattggt   540
ggcaagcagg cgctggagac ggtgcaggcg ctgttgccgg tgctgtgcca ggcccacggc   600
ttgacccccc agcaggtggt ggccatcgcc agcaataatg gtggcaagca ggcgctggag   660
acggtccagc ggctgttgcc ggtgctgtgc caggcccacg gcttgacccc ggagcaggtg   720
gtggccatcg ccagcacga tggcggcaag caggcgctgg agacggtcca gcggctgttg   780
ccggtgctgt gccaggccca cggcttgacc cggagcaggt ggtggccat cgccagccac   840
gatggcggca agcaggcgct ggagacggtc agcggctgt gccggtgct gtgccaggcc   900
cacggcttga ccccccagca ggtggtggcc atcgccagca atgcggtgg caagcaggcg   960
ctggagacgg tccagcggct gttgccggtg ctgtgccagg cccacggctt gacccccag   1020
caggtggtgg ccatcgccag ccacgatggc ggcaagcagg cgctggagac ggtccagcgg   1080
ctgttgccgg tgctgtgcca ggcccacggc ttgaccccgg agcaggtggt ggccatcgcc   1140
agccacgatg cggcaagca ggcgctggag acggtccagc ggctgttgcc ggtgctgtgc   1200
caggcccacg gcttgacccc ggagcaggtg gtggccatcg ccagcaatat tggtggcaag   1260
caggcgctgg agacggtgca ggcgctgttg ccggtgctgt gccaggccca cggcttgacc   1320
```

```
ccccagcagg tggtggccat cgccagcaat aatggtggca agcaggcgct ggagacggtc    1380
cagcggctgt tgccggtgct gtgccaggcc cacggcttga ccccccagca ggtggtggcc    1440
atcgccagca ataatggtgg caagcaggcg ctggagacgg tccagcggct gttgccggtg    1500
ctgtgccagg cccacggctt gaccccggag caggtggtgg ccatcgccag ccacgatggc    1560
ggcaagcagg cgctggagac ggtccagcgg ctgttgccgg tgctgtgcca ggcccacggc    1620
ttgaccccgg agcaggtggt ggccatcgcc agccacgatg gcggcaagca ggcgctggag    1680
acggtccagc ggctgttgcc ggtgctgtgc caggcccacg gcttgacccc ggagcaggtg    1740
gtggccatcg ccagcaatat tggtggcaag caggcgctgg agacggtgca ggcgctgttg    1800
ccggtgctgt gccaggccca cggcttgacc ccccagcagg tggtggccat cgccagcaat    1860
aatggtggca agcaggcgct ggagacggtc cagcggctgt tgccggtgct gtgccaggcc    1920
cacggcttga ccccggagca ggtggtggcc atcgccagca atattggtgg caagcaggcg    1980
ctggagacgg tgcaggcgct gttgccggtg ctgtgccagg cccacggctt gacccctcag    2040
caggtggtgg ccatcgccag caatggcggc ggcaggccgg cgctggagag cattgttgcc    2100
cagttatctc gccctgatcc ggcgttggcc gcgttgacca acgaccacct cgtcgccttg    2160
gcctgcctcg gcgggcgtcc tgcgctggat gcagtgaaaa agggattggg ggatcctatc    2220
agccgttccc agctggtgaa gtccgagctg gaggagaaga atccgagtt gaggcacaag     2280
ctgaagtacg tgccccacga gtacatcgag ctgatcgaga tcgcccggaa cagcacccag    2340
gaccgtatcc tggagatgaa ggtgatgaag ttcttcatga agtacaagtt ctacaagggc    2400
aagcacctgg gcggctccag gaagcccgac ggcgccatct acaccgtggg ctcccccatc    2460
gactacggcg tgatcgtgga caccaaggcc tactccggcg gctacaacct gcccatcggc    2520
caggccgacg aaatgcagag gtacgtggag gagaaccaga ccaggaacaa gcacatcaac    2580
cccaacgagt ggtggaaggt gtaccctcc agcgtgacga agttcaagtt cctgttcgtg     2640
tccggccact tcaagggcaa ctacaaggcc cagctgacca ggctgaacca catcaccaac    2700
tgcaacggcg ccgtgctgtc cgtggaggag ctcctgatcg gcggcgagat gatcaaggcc    2760
ggcacccctga ccctggagga ggtgaggagg aagttcaaca cggcgagat caacttcgcg    2820
gccgactgat aa                                                       2832

SEQ ID NO: 83          moltype = DNA  length = 50
FEATURE                Location/Qualifiers
misc_feature           1..50
                       note = B2M T02- TALEN targeting sequence
source                 1..50
                       mol_type = other DNA
                       organism = synthetic construct
SEQUENCE: 83
tccaaagatt caggtttact cacgtcatcc agcagagaat ggaaagtcaa                50

SEQ ID NO: 84          moltype = DNA  length = 2814
FEATURE                Location/Qualifiers
misc_feature           1..2814
                       note = Beta2M T02-TALEN - LEFT
source                 1..2814
                       mol_type = other DNA
                       organism = synthetic construct
SEQUENCE: 84
atgggcgatc ctaaaaagaa acgtaaggtc atcgattacc catacgatgt tccagattac     60
gctatcgata tcgccgatct acgcacgctc ggctacagcc agcagcaaca ggagaagatc    120
aaaccgaagg ttcgttcgac agtgcgcag caccacgagg cactggtcgg ccacgggttt     180
acacacgcgc atcgttgc gttaagccaa caccggcag cgttagggac cgtcgctgtc       240
aagtatcagg acatgatcgc agcgttgcca gaggcgacac acgaagcgat cgttggcgtc    300
ggcaaacagt ggtccggcgc acgcgctctg gaggccttgc tcacggtggc gggagagttg    360
agaggtccac cgttacagtt ggacacaggc caacttctca agattgcaaa acgtggcggc    420
gtgaccgcag tggaggcagt gcatgcatgg cgcaatgcac tgacgggtgc ccgctcaac     480
ttgaccccgg agcaggtggt ggccatcgcc agccacgatg gcggcaagca ggcgctggag    540
acggtccagc ggctgttgcc ggtgctgtgc caggcccacg gcttgacccc ggagcaggtg    600
gtggccatcg ccagccacga tggcggcaag caggcgctgg agacggtcca gcggctgttg    660
ccggtgctgt gccaggccca cggcttgacc ccggagcagg tggtggccat cgccagcaat    720
attggtggca agcaggcgct ggagacggtc aggcgctgt tgccggtgct gtgccaggcc     780
cacggcttga ccccggagca ggtggtggcc atcgccagca atattggtgg caagcaggcg    840
ctggagacgg tgcaggcgct gttgccggtg ctgtgccagg cccacggctt gacccctcag    900
caggtggtgg ccatcgccag caatattggt ggcaagcagg cgctggagac ggtcaggcg     960
ctgttgccgg tgctgtgcca ggcccacggc ttgaccccc agcaggtggt ggccatcgcc    1020
agcaataatg tggcaagca ggcgctggag acggtccagc ggctgttgcc ggtgctgtgc    1080
caggcccacg gcttgacccc ggagcaggtg gtggccatcg ccagcaatat tggtggcaag    1140
caggcgctgg agacggtgca ggcgctgttg ccggtgctgt gccaggccca cggcttgacc    1200
ccccagcagg tggtggccat cgccagcaat ggcggtggca agcaggcgct ggagacggtc    1260
cagcggctgt tgccggtgct gtgccaggcc cacggcttga ccccccagca ggtggtggcc    1320
atcgccagca atgcggtgg caagcaggcg ctggagacgg tccagcggct gttgccggtg     1380
ctgtgccagg cccacggctt gaccccggag caggtggtgg ccatcgccag ccacgatggc    1440
ggcaagcagg cgctggagac ggtccagcgg ctgttgccgg tgctgtgcca ggcccacggc    1500
ttgaccccgg agcaggtggt ggccatcgcc agcaatattg tggcaagca ggcgctggag    1560
acggtgcagg cgctgttgcc ggtgctgtgc aggcccacg gcttgacccc cagcaggtg     1620
gtggccatcg ccagcaataa tggtggcaag caggcgctgg agacggtcca gcggctgttg    1680
ccggtgctgt gccaggccca cggcttgacc ccccagcagg tggtggccat cgccagcaat    1740
aatggtggca agcaggcgct ggagacggtc cagcggctgt tgccggtgct gtgccaggcc    1800
cacggcttga ccccccagca ggtggtggcc atcgccagca atgcggtgg caagcaggcg     1860
ctggagacgg tccagcggct gttgccggtg ctgtgccagg cccacggctt gacccccag    1920
caggtggtgg ccatcgccag caatggcggt ggcaagcagg cgctggagac ggtccagcgg    1980
ctgttgccgg tgctgtgcca ggcccacggc ttgacccctc agcaggtggt ggccatcgcc    2040
```

```
agcaatggcg gcggcaggcc ggcgctggag agcattgttg cccagttatc tcgccctgat   2100
ccggcgttgg ccgcgttgac caacgaccac ctcgtcgcct tggcctgcct cggcgggcgt   2160
cctgcgctgg atgcagtgaa aaagggattg ggggatccta tcagccgttc ccagctggtg   2220
aagtccgagc tggaggagaa gaaatccgag ttgaggcaca agctgaagta cgtgccccac   2280
gagtacatcg agctgatcga gatcgcccgg aacagcaccc aggaccgtat cctggagatg   2340
aaggtgatgg agttcttcat gaaggtgtac ggctacaggg gcaagcacct gggcggctcc   2400
aggaagcccg acggcgccat ctacaccgtg ggctccccca tcgactacgg cgtgatcgtg   2460
gacaccaagg cctactccgg cggctacaac ctgcccatcg gccaggccga cgaaatgcag   2520
aggtacgtgg aggagaacca gaccaggaac aagcacatca accccaacga gtggtggaag   2580
gtgtaccccc tccagcgtga ccgagttcaag ttcctgttcg tgtccggcca cttcaagggc   2640
aactacaagg cccagctgac caggctgaac cacatcacca actgcaacgg cgccgtgctg   2700
tccgtggagg agctcctgat cggcggcgag atgatcaagg ccggcaccct gaccctggag   2760
gaggtgagga ggaagttcaa caacggcgag atcaacttcg cggccgactg ataa          2814

SEQ ID NO: 85           moltype = DNA  length = 2832
FEATURE                 Location/Qualifiers
misc_feature            1..2832
                        note = Beta2M T02-TALEN RIGHT
source                  1..2832
                        mol_type = other DNA
                        organism = synthetic construct
SEQUENCE: 85
atgggcgatc ctaaaaagaa acgtaaggtc atcgataagg agaccgccgc tgccaagttc   60
gagagacagc acatggacag catcgatatc gccgatctac gcacgctcgg ctacagccag   120
cagcaacagg agaagatcaa accgaaggtt cgttcgacag tggcgcagca ccacgaggca   180
ctggtcggcc acgggtttac acacgcgcac atcgttgcgt taagccaaca ccggcagcg   240
ttagggaccg tcgctgtcaa gtatcaggac atgatcgcac cgttgccaga ggcgacacac   300
gaagcgatcg ttggcgtcgg caaacagtgg tccggcgcac gcgctctgga ggccttgctc   360
acggtggcgg gagagttgag aggtccaccg ttacagttgg acacaggcca acttctcaag   420
attgcaaaac gtgtcggcgt gaccgcagtg gaggcagtgc atgatggcgt caatgcactg   480
acgggtgccc cgctcaactt gaccccccag caggtggtgg ccatcgccag caataatggt   540
ggcaagcagg cgctggagac ggtccagcgg ctgttgccgg tgctgtgcca ggcccacggc   600
ttgacccccgg agcaggtggt ggccatcgcc agcaatattg tggcaagca ggcgctggag   660
acggtgcagg cgctgttgcc ggtgctgtgc caggcccacg gcttgacccc ggagcaggtg   720
gtggccatcg ccagccacga tgcggcaag caggcgctgg agacggtcca gcggctgttg   780
ccggtgctgt gccaggccca cggcttgacc ccccagcagg tggtggccat cgccagcaat   840
ggcggtggca agcaggcgct ggagacggtc agcggctgt tgccggtgct gtgccaggcc   900
cacggcttga ccccccagca ggtggtggcc atcgccagca atggcggtgg caagcaggcg   960
ctggagacgg tccagcggct gttgccggtg ctgtgccagg cccacggctt gacccccag   1020
caggtggtgg ccatcgccag caatggcggt ggcaagcagg cgctggagac ggtccagcgg   1080
ctgttgccgg tgctgtgcca ggcccacggc ttgacccccgg agcaggtggt ggccatcgcc   1140
agccacgatg cggcaagca ggcgctggag acggtccagc ggctgttgcc ggtgctgtgc   1200
caggcccacg gcttgacccc ggagcaggtg gtggccatcg ccagccacga tgcggcaag   1260
caggcgctgg agacggtcca gcggctgttg ccggtgctgt gccaggccca cggcttgacc   1320
ccggagcagg tggtggccat cgccagcaat attggtggca agcaggcgct ggagacggtg   1380
caggcgctgt gcggtgct gtgccaggcc cacggcttga ccccccagca ggtggtggcc   1440
atcgccagca atggcggtgg caagcaggcg ctggagacgg tccagcggct gttgccggtg   1500
ctgtgccagg cccacggctt gacccccag caggtggtgg ccatcgccag caatggcggt   1560
ggcaagcagg cgctggagac ggtccagcgg ctgttgccgg tgctgtgcca ggcccacggc   1620
ttgacccccgg agcaggtggt ggccatcgcc agccacgatg cggcaagca ggcgctggag   1680
acggtccagc ggctgttgcc ggtgctgtgc caggcccacg gcttgacccc ccagcaggtg   1740
gtggccatcg ccagcaatgg cggtggcaag caggcgctgg agacggtcca gcggctgttg   1800
ccggtgctgt gccaggccca cggcttgacc ccggagcagg tggtggccat cgccagccac   1860
gatggcggca agcaggcgct ggagacggtc agcggctgt tgccggtgct gtgccaggcc   1920
cacggcttga ccccccagca ggtggtggcc atcgccagca atggcggtgg caagcaggcg   1980
ctggagacgg tccagcggct gttgccggtg ctgtgccagg cccacggctt gacccctcag   2040
caggtggtgg ccatcgccag caatggcggt ggcaggccgg cgctggagag cattgttgcc   2100
cagttatctc gccctgatcc ggcgttggcc gcgttgacaa cgaccacct cgtcgccttg   2160
gcctgcctcg gcgggcgtcc tgcgctggat gcagtgaaaa agggattggg ggatcctatc   2220
agccgttccc agctggtgaa gtccgagctg gaggagaaga aatccgagtt gaggcacaag   2280
ctgaagtacg tgccccacga gtacatcgag ctgatcgaga tcgcccggaa cagcacccag   2340
gaccgtatcc tggagatgaa ggtgatggag ttcttcatga aggtgtacgg ctacaggggc   2400
aagcacctgg gcggctccag gaagcccgac ggcgccatct acaccgtggg ctcccccatc   2460
gactacggcg tgatcgtgga caccaaggcc tactccggcg gctacaacct gcccatcggc   2520
caggccgacg aaatgcagag gtacgtggag gagaaccaga ccaggaacaa gcacatcaac   2580
cccaacgagt ggtggaaggt gtacccctcc agccgtgaccg agttcaagtt cctgttcgtg   2640
tccggccact tcaagggcaa ctacaaggcc agctgacca ggctgaacca catcaccaac   2700
tgcaacggcg ccgtgctgtc cgtggaggag ctcctgatcg gcggcgagat gatcaaggcc   2760
ggcaccctga ccctggagga ggtgaggagg aagttcaaca acggcgagat caacttcgcg   2820
gccgactgat aa                                                        2832

SEQ ID NO: 86           moltype = DNA  length = 47
FEATURE                 Location/Qualifiers
misc_feature            1..47
                        note = B2M T03- TALEN targeting sequence
source                  1..47
                        mol_type = other DNA
                        organism = synthetic construct
SEQUENCE: 86
```

```
ttagctgtgc tcgcgctact ctctctttct ggcctggagg ctatcca         47
```

| SEQ ID NO: 87 | moltype = DNA  length = 2814 |
|---|---|
| FEATURE | Location/Qualifiers |
| misc_feature | 1..2814 |
|  | note = Beta2M T03-TALEN - LEFT |
| source | 1..2814 |
|  | mol_type = other DNA |
|  | organism = synthetic construct |

```
SEQUENCE: 87
atgggcgatc ctaaaaagaa acgtaaggtc atcgattacc catacgatgt tccagattac   60
gctatcgata tcgccgatct acgcacgctc ggctacagcc agcagcaaca ggagaagatc  120
aaaccgaagg ttcgttcgac agtggcgcag caccacgagg cactggtcgg ccacgggttt  180
acacacgcgc acatcgttgc gttaagccaa cacccggcac cgttagggac cgtcgctgtc  240
aagtatcagg acatgatcgc agcgttgcca gaggcgacac acgaagcgat cgttggcgtc  300
ggcaaacagt ggtccggcgc acgcgctctg gaggccttgc tcacggtggc gggagagttg  360
agaggtccac cgttacagtt ggacacaggc caacttctca gattgcaaa acgtggcggc  420
gtgaccgcag tggaggcagt gcatgcatgg cgcaatgcac tgacgggtgc cccgctcaac  480
ttgacccgg agcaggtggt ggccatcgcc agcaatattg tggcaagca ggcgctggag  540
acggtgcagg cgctgttgcc ggtgctgtgc caggcccacg gcttgacccc ccagcaggtg  600
gtggccatcg ccagcaataa tggtggcaag caggcgctgg agacggtcca gcggctgttg  660
ccggtgctgt gccaggccca cggcttgacc ccggagcagg tggtggccat cgccagccac  720
gatggcggca agcaggcgct ggagacggtc agcggctgt tgccggtgct gtgccaggcc  780
cacggcttga ccccccagca ggtggtggcc atcgccagca atggcggtgg caagcaggcg  840
ctggagacgt ccagcggct gttgccggtg ctgtgccagg cccacggctt gacccccag  900
caggtggtgg ccatcgccag caataatggt ggcaagcagg cgctggagac ggtccagcgg  960
ctgttgccgg tgctgtgcca ggcccacggc ttgaccccc agcaggtggt ggccatcgcc  1020
agcaatggcg gtggcaagca ggcgctggag acggtccagc ggctgttgcc ggtgctgtgc  1080
caggcccacg gcttgacccc ccagcaggtg gtggccatcg ccagcaataa tggtggcaag  1140
caggcgctgg agacggtcca gcggctgttg ccggtgctgt gccaggccca cggcttgacc  1200
ccggagcagg tggtggccat cgccagccac gatggcggca agcaggcgct ggagacggtc  1260
cagcggctgt tgccggtgct gtgccaggcc cacggcttga ccccccagca ggtggtggcc  1320
atcgccagca atggcggtgg caagcaggcg ctggagacgg tccagcggct gttgccggtg  1380
ctgtgccagg cccacggctt gacccccag caggtggtgg ccatcgccag ccacgatggc  1440
ggcaagcagg cgctggagac ggtccagcgg ctgttgccgg tgctgtgcca ggcccacggc  1500
ttgacccccc agcaggtggt ggccatcgcc agcaataatg tggcaagca ggcgctggag  1560
acggtccagc ggctgttgcc ggtgctgtgc caggcccacg gcttgacccc ggagcaggtg  1620
gtggccatcg ccagccacga tggcggcaag caggcgctgg agacggtcca gcggctgttg  1680
ccggtgctgt gccaggccca cggcttgacc ccccagcagg tggtggccat cgccagcaat  1740
aatggtggca agcaggcgct ggagacggtc agcggctgt tgccggtgct gtgccaggcc  1800
cacggcttga ccccggagca ggtggtggcc atcgccagcc acgatggcgg caagcaggcg  1860
ctggagacgt ccagcggct gttgccggtg ctgtgccagg cccacggctt gacccccag  1920
caggtggtgg ccatcgccag caataatggt ggcaagcagg cgctggagac ggtccagcgg  1980
ctgttgccgg tgctgtgcca ggcccacggc ttgacccctc agcaggtggt ggccatcgcc  2040
agcaatggcg gcggcaggcc ggcgctggag agcattgttg cccagttatc tcgccctgat  2100
ccggcgttgg ccgcgttgac caacgaccac ctcgtcgcct tggcctgcct cggcgggcgt  2160
cctgcgtgc atgcagtgaa aaagggattg ggggatccta tcagccgttc ccagctggtg  2220
aagtccgagc tggaggagaa gaaatccgag ttgaggcaca agctgaagta cgtgccccac  2280
gagtacatcg agctgatcga gatcgcccgg aacagcaccc aggaccgtat cctggagatg  2340
aaggtgatgg agttcttcat gaaggtgtac ggctacaggg gcaagcacct gggcggctcc  2400
aggaagccg acggcgccat ctacaccgtg ggctcccca tcgactacgg cgtgatcgtg  2460
gacaccaagg cctactccgg cggctacaac ctgcccatcg gccaggccga cgaaatgcag  2520
aggtacgtgg aggagaacca gaccaggaac aagcacatca ccccaacga gtggtggaag  2580
gtgtaccct ccagcgtgac cgagttcaag ttcctgttcg tgtccggcca cttcaagggc  2640
aactacaagg cccagctgac caggctgaac cacatcacca actgcaacgg cgccgtgctg  2700
tccgtggagg agctcctgat cggcggcgag atgatcaagg ccggcacct gaccctggag  2760
gaggtgagga ggaagttcaa caacggcgag atcaacttcg cggccgactg ataa          2814
```

| SEQ ID NO: 88 | moltype = DNA  length = 2832 |
|---|---|
| FEATURE | Location/Qualifiers |
| misc_feature | 1..2832 |
|  | note = Beta2M T03-TALEN -RIGHT |
| source | 1..2832 |
|  | mol_type = other DNA |
|  | organism = synthetic construct |

```
SEQUENCE: 88
atgggcgatc ctaaaaagaa acgtaaggtc atcgataagg agaccgccgc tgccaagttc   60
gagagacagc acatggacag catcgatatc gccgatctac gcacgctcgg ctacagccag  120
cagcaacagg aagatcaa accgaaggtt cgttcgacag tggcgcagca ccacgaggca  180
ctggtcggcc acgggtttac acacgcgcac atcgttgcgt taagccaaca cccggcagc  240
ttagggaccg tcgctgtcaa gtatcaggac atgatcgcag cgttgccaga ggcgacacac  300
gaagcgatcg ttggcgtcgg caaacagtgg tccggcgcac gcgctctgga ggccttgctc  360
acggtggcgg gagagttgag aggtccaccg ttacagttgg acacaggcca acttctcaag  420
attgcaaaac gtggcggcgt gaccgcagtg gaggcagtgc atgcatggcg caatgcactg  480
acgggtgcc cgctcaactt gaccccccag caggtggtgg ccatcgccag caataatggt  540
ggcaagcagg cgctggagac ggtccagcgg ctgttgccgg tgctgtgcca ggcccacggc  600
ttgacccccc agcaggtggt ggccatcgcc agcaataatg tggcaagca ggcgctggag  660
acggtccagc ggctgttgcc ggtgctgtgc caggcccacg gcttgacccc ggagcaggtg  720
gtggccatcg ccagcaatat tggtggcaag caggcgctgg agacggtcca ggcgctgttg  780
```

```
ccggtgctgt gccaggccca cggcttgacc ccccagcagg tggtggccat cgccagcaat    840
ggcggtggca agcaggcgct ggagacggtc cagcggctgt tgccggtgct gtgccaggcc    900
cacggcttga ccccggagca ggtggtggcc atcgccagca atattggtgg caagcaggcg    960
ctggagacgg tgcaggcgct gttgccggtg ctgtgccagg cccacggctt gaccccccag   1020
caggtggtgg ccatcgccag caataatggt ggcaagcagg cgctggagac ggtccagcgg   1080
ctgttgccgg tgctgtgcca ggcccacggc ttgaccccgg agcaggtggt ggccatcgcc   1140
agccacgatg gcggcaagca ggcgctggag acggtccagc ggctgttgcc ggtgctgtgc   1200
caggcccacg gcttgacccc ggagcaggtg gtggccatcg ccagccacga tggcggcaag   1260
caggcgctgg agacggtcca gcggctgttg ccggtgctgt gccaggccca cggcttgacc   1320
cccagcagg tggtggccat cgccagcaat ggcggtggca agcaggcgct ggagacggtc   1380
cagcggctgt tgccggtgct gtgccaggcc cacggcttga ccccggagca ggtggtggcc   1440
atcgccagcc acgatggcgg caagcaggcg ctggagacgg tccagcggct gttgccggtg   1500
ctgtgccagg cccacggctt gaccccgag caggtggtgg ccatcgccag ccacgatggc   1560
ggcaagcagg cgctggagac ggtccagcgg ctgttgccga tgctgtgcca ggcccacggc   1620
ttgaccccgg agcaggtggt ggccatcgcc agcaatattg gtggcaagca ggcgctggag   1680
acggtgcagg cgctgttgcc ggtgctgtgc caggcccacg gcttgacccc ccagcaggtg   1740
gtggccatcg ccagcaataa tggtggcaag caggcgctgg agacggtcca gcggctgttg   1800
ccggtgctgt gccaggccca cggcttgacc ccccagcagg tggtggccat cgccagcaat   1860
aatggtggca agcaggcgct ggagacggtc cagcggctgt tgccggtgct gtgccaggcc   1920
cacggcttga ccccggagca ggtggtggcc atcgccagcc acgatggcgg caagcaggcg   1980
ctggagacgg tccagcggct gttgccggtg ctgtgccagg cccacggctt gacccctcag   2040
caggtggtgg ccatcgccag caatggcggc aggccgg gtggagag cattgttgcc   2100
cagttatctc gccctgatcc ggcgttggcc gcgttgacca acgaccacct cgtcgccttg   2160
gcctgcctcg gcgggcgtcc tgcgctggat cagtgaaaa agggattggg ggatcctatc   2220
agccgttccc agctggtgaa gtccgagctg aggagaaga atccgagtt gaggcacaag   2280
ctgaagtacg tgccccacga gtacatgcga ctgatcgaca tcgccggaa cagcacccag   2340
gaccgtatcc tggagatgaa ggtgatgag ttcttcatga aggtgtacgg ctacaggggc   2400
aagcacctgg gcggctccag gaagcccgac ggcgccatct acaccgtggg ctcccccatc   2460
gactacggcc tgatcgtgga caccaaggcc tactccggcg ctacaacct gcccatcggc   2520
caggccgacg aaatgcagag gtacgtggag gagaaccaga ccaggaacaa gcacatcaac   2580
cccaacgagt ggtggaaggt gtaccctcc agcgtgaccg agttcaagtt cctgttcgtg   2640
tccggccact tcaagggcaa ctacaaggcc cagctgacca ggctgaacca catcaccaac   2700
tgcaacggcc ccgtgctgtc cgtggaggag ctcctgatcg gcggcgagat gatcaaggcc   2760
ggcacctga ccctggagga ggtgaggagg aagttcaaca cggcgagat caacttcgcg   2820
gccgactgat aa                                                      2832

SEQ ID NO: 89          moltype = AA   length = 526
FEATURE                Location/Qualifiers
REGION                 1..526
                       note = Chimeric B2M-UL18
source                 1..526
                       mol_type = protein
                       organism = synthetic construct
SEQUENCE: 89
MALPVTALLL PLALLLHAAR PSRSVALAVL ALLSLSGLEA IQRTPKIQVY SRHPAENGKS     60
NFLNCYVSGF HPSDIEVDLL KNGERIEKVE HSDLSFSKDW SFYLLYYTEF TPTEKDEYAC    120
RVNHVTLSQP KIVKWDRDMG GGGSGGGGSG GGGSGGGGSM TMWCLTLFVL WMLRVVGMHV    180
LRYGYTGIFD DTSHMTLTVV GIFDGQHFFT YHVNSSDKAS SRANGTISWM ANVSAAYPTY    240
LDGERAKGDL IFNQTEQNLL ELEIALGYRS QSVLTWTHEC NTTENGSFVA GYEGFGWDGE    300
TLMELKDNLT LWTGPNYEIS WLKQNKTYID GKIKNISEGD TTIQRNYLKG NCTQWSVIYS    360
GFQTPVTHPV VKGGVRNQND NRAEAFCTSY GFFPGEINIT FIHYGNKAPD DSEPQCNPLL    420
PTFDGTFHQG CYVAIFCNQN YTCRVTHGNW TVEIPISVTS PDDSSSGEVP DHPTANKRYN    480
TMTISSVLLA LLLCALLFAF LHYFTTLKQY LRNLAFAWRY RKVRSS                   526

SEQ ID NO: 90          moltype = AA   length = 310
FEATURE                Location/Qualifiers
REGION                 1..310
                       note = SP-MICAed
source                 1..310
                       mol_type = protein
                       organism = synthetic construct
SEQUENCE: 90
MGGVLLTQRT LLSLVLALLF PSMASMEPHS LRYNLTVLSW DGSVQSGFLT EVHLDGQPFL     60
RCDRQKCRAK PQGQWAEDVL GNKTWDRETR DLTGNGKDLR MTLAHIKDQK EGLHSLQEIR    120
VCEIHEDNST RSSQHFYYDG ELFLSQNLET KEWTMPQSSR AQTLAMNVRN FLKEDAMKTK    180
THYHAMHADC LQELRRYLKS GVVLRRTVPP MVNVTRSEAS EGNITVTCRA SGFYPWNITL    240
SWRQDGVSLS HDTQQWGDVL PDGNGTYQTW VATRICQGEE QRFTCYMEHS GNHSTHPVPS    300
GKVLVLQSHW                                                          310

SEQ ID NO: 91          moltype = AA   length = 313
FEATURE                Location/Qualifiers
REGION                 1..313
                       note = SP-MICBed
source                 1..313
                       mol_type = protein
                       organism = synthetic construct
SEQUENCE: 91
MGGVLLTQRT LLSLVLALLF PSMASMAEPH SLRYNLMVLS QDESVQSGFL AEGHLDGQPF     60
LRYDRQKRRA KPQGQWAEDV LGAKTWDTET EDLTENGQDL RRTLTHIKDQ KGGLHSLQEI    120
```

```
RVCEIHEDSS TRGSRHFYYD GELFLSQNLE TQESTVPQSS RAQTLAMNVT NFWKEDAMKT    180
KTHYRAMQAD CLQKLQRYLK SGVAIRRTVP PMVNVTCSEV SEGNITVTCR ASSFYPRNIT    240
LTWRQDGVSL SHNTQQWGDV LPDGNGTYQT WVATRIRQGE EQRFTCYMEH SGNHGTHPVP    300
SGKVLVLQSQ RTD                                                      313

SEQ ID NO: 92           moltype = AA   length = 209
FEATURE                 Location/Qualifiers
REGION                  1..209
                        note = SP-ULBP1ed
source                  1..209
                        mol_type = protein
                        organism = synthetic construct
SEQUENCE: 92
MGGVLLTQRT LLSLVLALLF PSMASMGWVD THCLCYDFII TPKSRPEPQW CEVQGLVDER     60
PPLHYDCVNH KAKAFASLGK KVNVTKTWEE QTETLRDVVD FLKGQLLDIQ VENLIPIEPL    120
TLQARMSCEH EAHGHGRGSW QFLFNGQKFL LFDSNNRKWT ALHPGAKKMT EKWEKNRDVT    180
MFFQKISLGD CKMWLEEFLM YWEQMLDPT                                     209

SEQ ID NO: 93           moltype = AA   length = 211
FEATURE                 Location/Qualifiers
REGION                  1..211
                        note = SP-ULBP2ed
source                  1..211
                        mol_type = protein
                        organism = synthetic construct
SEQUENCE: 93
MGGVLLTQRT LLSLVLALLF PSMASMGRAD PHSLCYDITV IPKFRPGPRW CAVQGQVDEK     60
TFLHYDCGNK TVTPVSPLGK KLNVTTAWKA QNPVLREVVD ILTEQLRDIQ LENYTPKEPL    120
TLQARMSCEQ KAEGHSSGSW QFSFDGQIFL LFDSEKRMWT TVHPGARKMK EKWENDKVVA    180
MSFHYFSMGD CIGWLEDFLM GMDSTLEPSA G                                  211

SEQ ID NO: 94           moltype = AA   length = 206
FEATURE                 Location/Qualifiers
REGION                  1..206
                        note = SP-ULBP3ed
source                  1..206
                        mol_type = protein
                        organism = synthetic construct
SEQUENCE: 94
MGGVLLTQRT LLSLVLALLF PSMASMDAHS LWYNFTIIHL PRHGQQWCEV QSQVDQKNFL     60
SYDCGSDKVL SMGHLEEQLY ATDAWGKQLE MLREVGQRLR LELADTELED FTPSGPLTLQ    120
VRMSCECEAD GYIRGSWQFS FDGRKFLLFD SNNRKWTVVH AGARRMKEKW EKDSGLTTFF    180
KMVSMRDCKS WLRDFLMHRK KRLEPT                                        206

SEQ ID NO: 95           moltype = AA   length = 221
FEATURE                 Location/Qualifiers
REGION                  1..221
                        note = SP-N2DL4ed
source                  1..221
                        mol_type = protein
                        organism = synthetic construct
SEQUENCE: 95
MGGVLLTQRT LLSLVLALLF PSMASMHSLC FNFTIKSLSR PGQPWCEAQV FLNKNLFLQY     60
NSDNNMVKPL GLLGKKVYAT STWGELTQTL GEVGRDLRML LCDIKPQIKT SDPSTLQVEM    120
FCQREAERCT GASWQPATNG EKSLLFDAMN MTWTVINHEA SKIKETWKKD RGLEKYFRKL    180
SKGDCDHWLR EFLGHWEAMP EPTVSPVNAS DIHWSSSSLP D                       221

SEQ ID NO: 96           moltype = AA   length = 224
FEATURE                 Location/Qualifiers
REGION                  1..224
                        note = SP-RET1Ged
source                  1..224
                        mol_type = protein
                        organism = synthetic construct
SEQUENCE: 96
MGGVLLTQRT LLSLVLALLF PSMASMGLAD PHSLCYDITV IPKFRPGPRW CAVQGQVDEK     60
TFLHYDCGSK TVTPVSPLGK KLNVTTAWKA QNPVLREVVD ILTEQLLDIQ LENYIPKEPL    120
TLQARMSCEQ KAEGHSSGSW QLSFDGQIFL LFDSENRMWT TVHPGARKMK EKWENDKDMT    180
MSFHYISMGD CTGWLEDFLM GMDSTLEPSA GAPPTMSSGT AQPR                    224

SEQ ID NO: 97           moltype = AA   length = 211
FEATURE                 Location/Qualifiers
REGION                  1..211
                        note = SP-RAETILed
source                  1..211
                        mol_type = protein
                        organism = synthetic construct
SEQUENCE: 97
MGGVLLTQRT LLSLVLALLF PSMASMRRDD PHSLCYDITV IPKFRPGPRW CAVQGQVDEK     60
```

```
TFLHYDCGNK TVTPVSPLGK KLNVTMAWKA QNPVLREVVD ILTEQLLDIQ LENYTPKEPL  120
TLQARMSCEQ KAEGHSSGSW QFSIDGQTFL LFDSEKRMWT TVHPGARKMK EKWENDKDVA  180
MSFHYISMGD CIGWLEDFLM GMDSTLEPSA G                                211
```